United States Patent
Hartley et al.

(10) Patent No.: US 6,270,969 B1
(45) Date of Patent: *Aug. 7, 2001

(54) RECOMBINATIONAL CLONING USING ENGINEERED RECOMBINATION SITES

(75) Inventors: James L. Hartley, Frederick; Michael A. Brasch, Gaithersburg, both of MD (US)

(73) Assignee: Invitrogen Corporation, Carlsbad, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/233,492

(22) Filed: Jan. 20, 1999

Related U.S. Application Data

(63) Continuation of application No. 08/663,002, filed on Jun. 7, 1996, now Pat. No. 5,888,732, which is a continuation-in-part of application No. 08/486,139, filed on Jun. 7, 1995, now abandoned.

(51) Int. Cl.[7] .............................. C12Q 1/68; C12N 15/63; C12N 15/87; C07H 21/04
(52) U.S. Cl. ........................ 435/6; 435/320.1; 435/462; 536/23.1; 536/24.1
(58) Field of Search ......................... 435/6, 320.1, 462; 536/23.1, 24.1

(56) References Cited

U.S. PATENT DOCUMENTS

| | | |
|---|---|---|
| 4,673,640 | 6/1987 | Backman . |
| 4,743,546 | 5/1988 | Backman et al. . |
| 4,959,317 | 9/1990 | Sauer . |
| 5,227,288 | 7/1993 | Blattner . |
| 5,286,632 | 2/1994 | Jones . |
| 5,354,668 | 10/1994 | Auerbach . |
| 5,434,066 | 7/1995 | Bebee et al. . |
| 5,470,727 | 11/1995 | Mascarenhas et al. . |
| 5,591,609 | 1/1997 | Auerbach . |
| 5,614,389 | 3/1997 | Auerbach . |
| 5,635,381 | 6/1997 | Hooykaas et al. . |
| 5,650,308 | 7/1997 | Baum . |
| 5,658,772 * | 8/1997 | Odell et al. ................. 435/172.3 |
| 5,677,170 | 10/1997 | Devine et al. . |
| 5,677,177 * | 10/1997 | Wahl et al. .................. 435/325 |
| 5,710,248 | 1/1998 | Grose . |
| 5,723,765 | 3/1998 | Oliver et al. . |
| 5,733,733 | 3/1998 | Auerbach . |
| 5,733,743 | 3/1998 | Johnson et al. . |
| 5,744,336 | 4/1998 | Hodges et al. . |
| 5,766,891 | 6/1998 | Shuman . |
| 5,776,449 | 7/1998 | Baum . |
| 5,830,707 * | 11/1998 | Bushman .................... 800/288 |
| 5,837,242 | 11/1998 | Holliger et al. ............. 424/136.1 |
| 5,843,772 | 12/1998 | Devine et al. . |
| 5,851,808 | 12/1998 | Elledge et al. . |
| 5,858,657 | 1/1999 | Winter et al. . |
| 5,871,907 | 2/1999 | Bushman . |
| 5,874,259 | 2/1999 | Szybalski . |
| 5,888,732 | 3/1999 | Hartley et al. . |
| 5,919,676 | 7/1999 | Graham et al. . |
| 5,928,914 | 7/1999 | Lebouch et al. . |
| 5,989,872 | 11/1999 | Luo et al. . |
| 6,010,884 | 1/2000 | Griffiths et al. ............. 435/69.7 |
| 6,143,557 | 11/2000 | Hartley et al. . |
| 6,171,861 | 1/2001 | Hartley et al. . |

FOREIGN PATENT DOCUMENTS

| | | |
|---|---|---|
| 2141412 | 2/1994 | (CA) . |
| 0 160 571 | 11/1985 | (EP) . |
| 0 300 422 | 1/1989 | (EP) . |
| 1 035 208 | 9/2000 | (EP) . |
| WO 91/02801 | 3/1991 | (WO) . |
| WO 91/16427 | 10/1991 | (WO) . |
| WO 92/20791 | 11/1992 | (WO) . |
| WO 93/15191 | 8/1993 | (WO) . |
| WO 93/19172 | 9/1993 | (WO) . |
| WO 94/09127 | 4/1994 | (WO) . |
| WO 94/17176 | 8/1994 | (WO) . |
| WO 95/00555 * | 1/1995 | (WO) ..................... 424/94.5 |
| WO 97/06265 | 2/1997 | (WO) . |
| WO 97/09436 | 3/1997 | (WO) . |
| WO 97/25446 | 7/1997 | (WO) . |
| WO 97/32481 | 9/1997 | (WO) . |
| WO 98/10086 | 3/1998 | (WO) . |
| WO 98/53056 | 11/1998 | (WO) . |
| WO 99/10488 | 3/1999 | (WO) . |
| WO 99/21977 | 5/1999 | (WO) . |
| WO 99/25851 | 5/1999 | (WO) . |
| WO 99/55851 | 11/1999 | (WO) . |
| WO 00/60091 | 10/2000 | (WO) . |
| WO 01/05961 | 1/2001 | (WO) . |
| WO 01/11058 | 2/2001 | (WO) . |

OTHER PUBLICATIONS

Lebreton et al. Mutainos that improve tha binding of yeast FLP recombinase to its substrate. Genetics vol. 118:393–400, Mar. 1988.*

(List continued on next page.)

Primary Examiner—Robert A. Schwartzman
Assistant Examiner—Williams Sandals
(74) Attorney, Agent, or Firm—Sterne, Kessler, Goldstein & Fox P.L.L.C.

(57) ABSTRACT

Recombinational cloning is provided by the use of nucleic acids, vectors and methods, in vitro and in vivo, for moving or exchanging segments of DNA molecules using engineered recombination sites and recombination proteins to provide chimeric DNA molecules that have the desired characteristic(s) and/or DNA segment(s).

130 Claims, 44 Drawing Sheets

OTHER PUBLICATIONS

Lorbach, E. et al., "Site–specific Recombination in Human Cells Catalyzed by Phage λ Integrase Mutants," *J. Mol. Biol.* 296:1175–1181 (Mar. 2000).

Zahra, D.G., et al., "Selectable in–vivo recombination to increase antibody library size—an improved phage display vector system," *Gene* 227:49–54 (1999).

Albert, H., et al., "Site–specific integration of DNA into wild–type and mutant lox sites placed in the plant genome," *Plant J.* 7:649–659 (Apr. 1995).

Dale, E.C., and Ow, D.W., "Mutations in the Cre/lox recombination site enhance the stability of recombination products: Applications for gene targeting in plants," *J. Cell. Biochem.* 16(*Suppl. F*):206, abstract No. Y 108 (1992).

Davies, J., and Riechmann, L., "An antibody VH domain with a lox–Cre site integrated into its coding region: bacterial recombination within a single polypeptide chain," *FEBS Letts.* 377:92–96 (Dec. 1995).

Hall, R.M., and Collins, C.M., "Mobile gene cassettes and integrons: capture and spread of genes by site–specific recombination," *Molec. Microbiol.* 15:593–600 (Feb. 1995).

Krafte, D.S., et al., "Stable Expression and Functional Characterization of a Human Cardiac Na$^+$ Channel Gene in Mammalian Cells," *J. Mol. Cell Cardiol.* 27:823–830 (Feb. 1995).

Lee, G., and Saito, I., "Role of nucleotide sequences of loxP spacer region in Cre–mediated recombination," *Gene* 216:55–65 (1998).

Simpson, J.C., et al., "Systematic subcellular localization of novel proteins identified by large–scale cDNA sequencing," *EMBO Rep.* 11:287–292 (2000).

Venkatesh, T.V., and Radding, C.M., "Ribosomal Protein S1 and NusA Protein Complexed to Recombination Protein β of Phage λ," *J. Bacteriol.* 175:1844–1846 (1993).

Dialog File 351 (Derwent World Patents Index), unverified English language abstract for WIPO/PCT Publication No. WO 98/53056 (Doc. No. AN4), WPI Accession No. 1999–000502/199901.

Dialog File 351 (Derwent World Patents Index), unverified English language abstract for WIPO/PCT Publication No. WO 99/25851 (Doc. No. AP4), WPI Accession No. 1999–347485/199929.

Sternberg, N., "Bacteriophage P1 cloning system for the isolation, amplification, and recovery of DNA fragments as large as 100 kilobase pairs," *Proc. Natl. Acad. Sci. USA* 87:103–107 (1990).

Reed, R.R., "Transposon–Mediated Site–Specific Recombination: A Defined in Vitro System," *Cell* 25:713–719 (1981).

Reed, R.R., and Grindley, N.D.F., "Transposon–Mediated Site–Specific Recombination in Vitro: DNA Cleavage and Protein–DNA Linkage at the Recombination Site," *Cell* 25:721–728 (1981).

Andrews B.J., et al., "The FLP Recombinase of the 2μ Circle DNA of Yeast: Interaction with Its Target Sequences," *Cell* 40:795–803 (1985).

Andrews, B.J., et al., "Interaction of the FLP Recombinase of the *Saccharomyces cerevisiae* 2 μm Plasmid with Mutated Target Sequences," *Mol. Cell. Biol.* 6:2482–2489 (1986).

Mizuuchi, K., and Mizuuchi, K., "Integrative Recombination of Bacteriophage λ: In Vitro Study of the Intermolecular Reaction," *Cold Spring Harb. Symp. Quant. Biol.* 43:1111–1114 (1979).

Bernard, P., "Positive Selection of Recombinant DNA by CcdB," *BioTechniques* 21:320–323 (Aug. 1996).

Jaffé, A., et al., "Effects of the ccd Function of the F Plasmid on Bacterial Growth," *J. Bacteriol.* 163:841–849 (1985).

Nash, H.A., "Integrative Recombination of Bacteriophage Lambda DNA In Vitro," *Proc. Natl. Acad. Sci. USA* 72:1072–1076 (1975).

Abremski, K., and Gottesman, S., "Purification of the Bacteriophage λ xis Gene Product Required for λ Excisive Recombination," *J. Biol. Chem.* 257:9658–9662 (1982).

Abremski, K., et al., "Studies on the Properties of P1 Site–specific Recombination: Evidence for Topologically Unlinked Products Following Recombination," *Cell* 32:1301–1311 (1983).

Abremski, K., et al., "Bacteriophage P1 Cre–loxP Site–specific Recombination: Site–specific DNA Topoisomerase Activity of the Cre Recombination Protein," *J. Biol. Chem.* 261:391–396 (1986).

Adams, D. E., et al., "Cre–lox Recombination in *Escherchia coli* Cells: Mechanistic Differences from the in Vitro Reaction," *J. Mol. Biol.* 226:661–673 (1992).

Anton, M. and Graham, F. L., "Site–Specific Recombination Mediated by an Adenovirus Vector Expressing the Cre Recombinase Protein: a Molecular Switch for Control of Gene Expression," *J. Virol.* 69:4600–4606 (Aug. 1995).

Araki, H., et al., "Site–specific Recombinase, R, Encoded by Yeast Plasmid pSR1," *J. Mol. Biol.* 225:25–37 (1992).

Argos, P., et al., "The integrase family of site–specific recombinases: regional similarities and global diversity," *EMBO J.* 5:433–440 (1986).

Atlung, T., et al., "A versatile method for integration of genes and gene fusions into the λ attachment site of *Escherichia coli*," *Gene* 107:11–17 (1991).

Ausubel, F. M., et al., "Mutagenesis by the Polymerase Chain Reaction," in *Current Protocols in Molecular Biology*, pp. 8.5.1–8.5.9, John Wiley & Sons, Inc., Boston, MA, (1995).

Balakrishnan, R., et al., "A gene cassette for adapting *Escherichia coli* strains as hosts for att–Int–mediated rearrangement and $P_L$ expression vectors," *Gene* 138:101–104 (Jan. 1994).

Bayley, C. C., et al., "Exchange of gene activity in transgenic plants catalyzed by the Cre–lox site–specific recombination system," *Plant Mol. Biol.* 18:353–361 (1992).

Black, L.W., "In vitro packaging into phage T4 particles and specific recirculization of phage lambda DNAs," *Gene* 46:97–101 (1986).

Bethke, B. and Sauer, B., "Segmental genomic replacement by Cre–mediated recombination: genotoxic stress activation of the p53 promoter in single–copy transformants," *Nucl. Acids Res.* 25:2828–2834 (Jul. 1997).

Bernard, P. and Couturier, M., "Cell Killing by the F Plasmid Ccdb Protein Involves Poisoning of Dna–topoisomerase II Complexes," *J. Mol. Biol.* 226:735–745 (1992).

Bernard, P., et al., "Positive–selection vector using the F plasmid ccdB killer gene," *Gene* 148:71–74 (Oct. 1994).

Betz, U. A. K., et al., "Bypass of lethality with mosaic mice generated by Cre–loxP–mediated recombination," *Curr. Biol.* 6:1307–1316 (Oct. 1996).

Bhandari, P and Gowrishankar, J., "An *Escherichia coli* host Strain Useful for Efficient Overproduction of Cloned Gene Products with Nacl as the Inducer," *J. Bacteriol.* 179:4403–4406 (Jul. 1997).

Bochner, B. R., et al., "Positive Selection for Loss of Tetracycline Resistance," *J. Bacteriol.* 143:926–933 (1980).

Boyd, A. C., "Turbo cloning: a fast, efficient method for cloning PCR products and other blunt–ended DNA fragments into plasmids," *Nucl. Acids Res.* 21:817–821 (1993).

Broach, J. R., et al., "Recombination within the Yeast Plasmid 2µ Circle is Site–Specific," *Cell* 29:227–234 (1982).

Brunelli, J. P. and Pall, M. L., "A Series of Yeast/*Escherichia coli* λ Expression Vectors Designed for Directional Cloning of cDNAs and cre/lox–Mediated Plasmid Excision," *Yeast* 9:1309–1318 (1993).

Brunelli, J.P., and Pall, M.L., "Lambda/Plasmid Vector Construction by In Vivo cre/lox–Mediated Recombination," *BioTechniques* 16:1061–1064 (Jun. 1994).

Buchholz, F., et al., "A simple assay to determine the functionality of Cre of FLP recombination targets in genomic manipulation constructs," *Nucl. Acids Res.* 24:3118–3119 (Aug. 1996).

Buchholz, F., et al., "Different thermostabilities of FLP and Cre recombinases: implications for applied site–specific recombination," *Nucl. Acids Res.* 24:4256–4262 (Nov. 1996).

Zhang, Y. et al., "A New logic for DNA engineering using recombination in *Escherichia coli,*" *Nat. Genet.* 20:123–128 (Oct. 1998).

Bushman, W., et al., "Control of Directionality in Lambda Site Specific Recombination," *Science* 230:906–911 (1985).

Campbell, A. M., "Chromosomal Insertion Sites for Phages and Plasmids," *J. Bacteriol.* 174:7495–7499 (1992).

Chapin, S.J., et al., "Differential Expression of Alternatively Spliced Forms of MAP4: a Repertoire of Structurally Different Microtubule–binding Domains," *Biochem.* 34:2289–2301 (Feb. 1995).

Craig, N.L. and Nash, H.A., "The Mechanism of Phage Lambda Site–specific Recombination: Site–specific Breakage of Dna by Int Topoisomerase," *Cell* 35:795–803 (1983).

Dale, E. C. and Ow, D. W., "Intra– and intermolecular site–specific recombination in plant cells mediated by bacteriophage P1 recombinase," *Gene* 91:79–85 (1990).

Dale, E. C. and Ow, D. W., "Gene transfer with subsequent removal of the selection gene from the host genome," *Proc. Natl. Acad. Sci. USA* 88:10558–10562 (1991).

Dang, D. T. and Perrimon, N., "Use of a Yeast Site–Specific Recombinase to Generate Embryonic Mosaics in Drosophila," *Develop. Genetics* 13:367–375 (1992).

Devine, S. E., and Boeke, J.D., "Efficient integration of artificial transposons into plasmid targets in vitro: a useful tool for DNA mapping, sequencing and genetic analysis," *Nucl. Acids Res.* 22:3765–3722 (Sep. 1994).

Diederich, L., et al., "New Cloning Vectors for Integration into the λ Attachment Site attB of the *Escherichia coli* Chromosome," *Plasmid* 28:14–24 (1992).

Dymecki, S. M., "A modular set of Flp, FRT and lacZ fusion vectors for manipulating genes by site–specific recombination," *Gene* 171:197–201 (Jun. 1996).

Elledge, S. J., et al., "λYES: A multifunctional cDNA expression vector for the isolation of genes by complementation of yeast and *Escherichia coli* mutations," *Proc. Natl. Acad. Sci. USA* 88:1731–1735 (1991).

Feil, R., et al., "Regulation of Cre Recombinase Activity by Mutated Estrogen Receptor Ligand–Binding Domains," *Biochem. Biophys. Res. Comm.* 237:752–757 (Aug. 1997).

Ferguson, J., et al., "Construction and characterization of three yeast–*Escherichia coli* shuttle vectors designed for rapid subcloning of yeast genes on small DNA fragments," *Gene* 16:191–197 (1981).

Fiering, S., et al., "An 'in–out' strategy using gene targeting and FLP recombinase for the functional dissection of complex DNA regulatory elements: Analysis of the β–globin locus control region," *Proc. Natl. Acad. Sci. USA* 90:8469–8473 (1993).

Filutowicz, M., et al., "Purification of the *Escherichia coli* integration host factor (IHF) in one chromatographic step," *Gene* 147:149–150 (Sep. 1994).

Fukushige, S. and Sauer, B., "Genomic targeting with a positive–selection lox integration vector allows highly reproducible gene expression in mammalian cells," *Proc. Natl. Acad. Sci. USA* 89:7905–7909 (1992).

Gage, P.J. et al., "A Cell–Free Recombination System for Site–Specific Integration of Multigenic Shuttle Plasmids into the Herpes Simplex Virus Type 1 Genome," *J. Virol.* 66:5509–5515 (1992).

Geoffroy, F., et al., "A new phage display system to construct multicombinatorial libraries of very large antibody repertoires," *Gene* 151:109–113 (Dec. 1994).

Golic, K. G. and Lindquist, S., "The FLP Recombinase of Yeast Catalyzes Site–Specific Recombination in the Drosophila Genome," *Cell* 59:499–509 (1989).

Gu, H. et al., "Deletion of a DNA polymerase beta gene segment in T cells using cell type–specific gene targeting," *Science* 265:103–106 (Ju. 1994).

Hardy, S., et al., "Construction of Adenovirus Vectors through Cre–lox Recombination," *J. Virol.* 71:1842–1849 (Mar. 1997).

Hasan, N., and Szybalski, W., "Control of cloned gene expression by promoter inversion in vivo: construction of improved vectors with a multiple cloning site and the $P_{tac}$ promoter," *Gene* 56:145–151 (1987).

Hasan, N., et al., "*Escherichia coli* genome targeting, I. Cre–lox–mediated in vitro generation of ori⁻plasmids and their in vivo chromosomal integration and retrieval," *Gene* 150:51–56 (Dec. 1994).

Hashimoto–Gotoh, T., et al., "Improved vector, pHSG664, for direct streptomycin–resistance selection: cDNA cloning with G:C–tailing procedure and subcloning of double–digested DNA fragments," *Gene* 41:125–128 (1986).

Hoekstra, M. F., et al., "Shuttle Mutagenesis: Bacterial Transposons for Genetic Manipulations in Yeast," *Meth. Enzymol.* 194:329–342 (1991).

Hoess, R. H., et al., "The role of the loxP spacer region in P1 site–specific recombination," *Nucl. Acids Res.* 14:2287–2300 (1986).

Hoess, R. H., and Abremski, K., "The Cre–lox Recombination System," in: *Nucleic Acids and Molecular Biology*, vol. 4, ed. by Eckstein, F. and D. M. J. Lilley, Springer–Verlag, Berlin, pp. 99–109 (1990).

Holt, C.L., and May, G.S., "A novel phage λ replacement Cre–lox vector that has automatic subcloning capabilities," *Gene* 133:95–97 (1993).

Kanaar, R., et al., "Gin–Mediated Recombination of Catenated and Knotted DNA Substrates: Implications for the Mechanism of Interaction Between Cis–Acting Sites," *Cell* 58:147–159 (1989).

Kilby, N. J., et al., "Site–specific recombinases: tools for genome engineering," *Trends in Genetics* 9:413–421 (1993).

Kim, S. et al., "Lambda Int protein bridges between higher order complexes at two distant chromosomal loci attL and attR," *Science 256:*198–263 (1992).

Kozak, M., "Comparison of Initiation of Protein Synthesis in Procaryotes, Eucaryotes, and Organelles," *Microbiol. Rev. 47:*1–45 (1983).

Kozak, M., "An analysis of 5'-noncoding sequences from 699 vertebrate messenger RNAs," *Nucl. Acids Res. 15:*8125–8132 (1987).

Kozak, M., "Structural features in eukaryotic mRNAs that modulate the initiation of translation," *J. Biol. Chem. 266:*19867–19870 (1991).

Kühn, R., et al., "Inducible Gene Targeting in Mice," *Science 269:*1427–1429 (Sep. 1995).

Lakso, M., et al., "Targeted oncogene activation by site–specific recombination in transgenic mice," *Proc. Natl. Acad. Sci. USA 89:*6232–6236 (1992).

Lander, E.S., "The New Genomics: Global Views of Biology," *Science 274:*536–539 (Oct. 1996).

Landy, A., "Mechanistic and structural complexity in the site–specific recombination pathways of Int and FLP," *Curr. Op. Genet. Develop. 3:*699–707 (1993).

Landy, A., "Dynamic, Structural, and Regulatory Aspects of λ Site–Specific Recombination," *Annu. Rev. Biochem. 58:*913–949 (1989).

Leong, J.M., et al., "Generation of single base–pair deletions, insertions, and substitutions by a site–specific recombination system," *Proc. Natl. Acad. Sci. USA 82:*6990–6994 (1985).

Lee, E. C., et al., "Genetic Analysis of *Escherichia coli* Integration Host Factor Interactions with Its Bacteriophage λ H' Recognition Site," *J. Bacteriol. 173:*609–617 (1991).

Liu, Q. et al., "The univector plasmid–fusion system, a method for rapid construction of recombinant DNA without restriction enzymes," *Curr. Biol. 8:*1300–1309 (Nov. 1998).

Luckow, V. A., et al., "Efficient Generation of Infectious Recombinant Baculoviruses by Site–Specific Transposon-–Mediated Insertion of Foreign Genes into a Baculovirus Genome Propagated in *Escherichia coli,*" *J. Virol. 67:*4566–4579 (1993).

Maeser, S., and Kahmann, R., "The Gin recombinase of phage Mu can catalyse site–specific recombination in plant protoplasts," *Mol. Gen. Genet. 230:*170–176 (1991).

Mahillon, J., et al., "IS231 and other *Bacillus thuringiensis* transposable elements: a review," *Genetica 93:*13–26 (Nov. 1994).

Matsuzaki, H., et al., "Chromosome Engineering in *Saccharomyces cerevisiae* by Using a Site–Specific Recombination System of a Yeast Plasmid," *J. Bacteriol. 172:*610–618 (1990).

McCarthy, JE and Brimacombe, R., "Prokaryotic translation: the interactive pathway leading to initiation," *Trends Genet. 10:*402–407 (Nov 1994).

Miki, T. et al., "Control of Segregation of Chromosomal Dna by Sex Factor F in *Escherichia coli.* Mutants of Dna Gyrase Subunit a Suppress letd (ccdb) Product Growth Inhibition," *J. Mol. Biol. 225:*39–52 (1992).

Mizuuchi, M. and Mizuuchi, K., "The extent of DNA sequence required for a functional bacterial attachment site of phage lambda," *Nucl. Acids Res. 13:*1193–1208 (1985).

Mozo, T. and Hooykaas, P. J. J., "Design of a novel system for the construction of vectors for Agrobacterium–mediated plant transformation," *Mol. Gen. Genet 236:*1–7 (1992).

Mullins, L.J., et al., "Efficient Cre–lox linerisation of BACs: applications to physical mapping and generation of transgenic animals," *Nucl. Acids Res. 25:*2539–2540 (Jun. 1997).

Nagaraja, R. and Weisberg, R. A., "Specificity Determinants in the Attachment Sites of Bacteriophages HK022 and λ," *J. Bacteriol. 172:*6540–6550 (1990).

Nash, H.A. and Robertson, CA, "Purification and Properties of the *Escherichia coli* Protein Factor Required for λ Integrative Recombination," *J. Biol. Chem. 256:*9246–9253 (1981).

Nash, H. A., "Purification and Properties of the Bacteriophage Lambda Int Protein," *Meth. Enzymol. 100:*210–216 (1983).

Nash, H. A., et al., "Role of homology in site–specific recombination of bacteriophage λ: Evidence against joining of cohesive ends," *Proc. Natl. Acad. Sci. USA 84:*4049–4053 (1987).

Nash, H.A., "Bending and supercoiling of DNA at the attachment site of bacteriophage Λ," *Trends Biochem. Sci 15:*222–227 (1990).

Numrych, T. E., et al., "A comparison of the effects of single–base and triple–base changes in the integrase arm-–type binding sites on the site–specific recombination of bacteriophage lambda," *Nucl. Acids Res. 18:*3953–3959 (1990).

Numrych, T.E., et al., "Characterization of the bacteriophage lambda excisionase (Xis) protein: the C–terminus is required for Xis–integrase cooperativity but not for DNA binding," *EMBO J. 11:*3797–3806 (1992).

Nunes–Düby, S.E., et al., "Half–att Site Substrates Reveal the Homology Independence and Minimal Protein Requirements for Productive Synapsis in λ Excisive Recombination," *Cell 59:*197–206 (1989).

Nunes–Düby, S.E., et al., "Similarities and differences among 105 members of the Int family of site–specific recombinases," *Nucl. Acids Res. 26:*391–406 (Jan. 1998).

Oberto, J., et al., "A segment of the phage HK022 chromosome is a mosaic of other lambdoid chromosomes," *Nucl. Acids Res. 22:*354–356 (Feb. 1994).

Orban, P. C., et al., "Tissue– and site–specific DNA recombination in transgenic mice," *Proc. Natl. Acad. Sci. USA 89:*6861–6865 (1992).

Padgett, K. A. and Sorge, J.A., "Creating seamless junctions independent of restriction sites in PCR cloning," *Gene 168:*31–35 (Feb. 1996).

Palazzolo, M. J., et al., "Phage lambda cDNA cloning vectors for subtractive hybridization, fusion–protein synthesis and Cre–loxP automatic plasmid subcloning," *Gene 88:*25–36 (1990).

Pan, G., et al., "Ligation of Synthetic Activated DNA Substrates by Site–specific Recombinases and Topoisomerase I," *J. Biol. Chem. 268:*3683–3689 (1993).

Parks, R.J., and Graham, F.L., "A Helper–Dependent System for Adenovirus Vector Production Helps Define a Lower Limit for Efficient DNA Packaging," *J. Virol. 71:*3293–3298 (Apr. 1997).

Peakman, T. C., et al., "Highly efficient generation of recombinant baculoviruses by enzymatically mediated site–specific in vitro recombination," *Nucl. Acids Res. 20:*495–500 (1992).

Peredelchuk, M.Y., and Bennett, G.N., "A method for construction of *E. coli* strains with multiple DNA insertions in the chromosome," *Gene 187:*231–238 (Mar. 1997).

Pichel, J. G., et al., "Timing of SV40 oncogene activation by site–specific recombination determines subsequent tumor progression during murine lens development," *Gene* 8:3333–3342 (1993).

Pierce, J. C., et al., "A positive selection vector for cloning high molecular weight DNA by the bacteriophage P1 system: Improved cloning efficacy," *Proc. Natl Acad. Sci. USA* 89:2056–2060 (1992).

Podhajska, A. J., et al., "Control of cloned gene expression by promoter inversion in vivo: construction of the heat-–pulse–activated att–nutL–p–att–N module," *Gene* 40:163–168 (1985).

Pósfai, G., et al., "In vivo excision and amplification of large segments of the *Escherichia coli* genome," *Nucl. Acids Res.* 22:2392–2398 (Jun. 1994).

Prasad, P. V., et al., "Substrate Recognition by the 2 $\mu$m Circle Site–Specific Recombinase: Effect of Mutations within the Symmetry Elements of the Minimal Substrate," *Mol. Cell. Biol.* 6:4329–4334 (1986).

Qian, X., et al., "Reactions between Half– and Full–FLP Recombination Target Sites: A Model System for Analyzing Early Steps in FLP Protein–Mediated Site–Specific Recombination," *J. Biol. Chem.* 267:7794–7805 (1992).

Richet, E., et al., "The Interaction of Recombination Proteins with Supercoiled DNA: Defining the Role of Supercoiling in Lambda Integrative Recombination," *Cell* 46:1011–1021 (1986).

Richet, E., et al., "Synapsis of Attachment Sites during Lambda Integrative Recombination Involves Capture of a Naked DNA by a Protein–DNA Complex," *Cell* 52:9–17 (1988).

Sadowski, P., "Site–Specific Recombinases: Changing Partners and Doing the Twist," *J. Bacteriol.* 165:341–347 (1986).

Sadowski, P.D., "The Flp Recombinase of the 2–microns Plasmid of *Saccharomyces cerevisiae*," *Prog. Nucl. Acid Res. Mol. Biol.* 51:53–91 (1995).

Sauer, B., et al., "Site–specific insertion of DNA into a pseudorabies virus vector," *Proc. Natl. Acad. Sci. USA* 84:9108–9112 (1987).

Sauer, B., "Functional Expression of the cre–lox Site–Specific Recombination System in the Yeast *Saccharomyces cerevisiae*," *Mol. Cell. Biol.* 7:2087–2096 (1987).

Sauer, B. and Henderson, N., "The cyclization of linear DNA in *Escherichia coli* by site–specific recombination," *Gene* 70:331–341 (1988).

Sauer, B. and Henderson, N., "Cre–stimulated recombination at loxP–containing DNA sequences placed into the mammalian genome," *Nucl. Acids Res.* 17:147–161 (1989).

Sauer, B., "Manipulation of Transgenes by Site–Specific Recombination: Use of Cre Recombinase," *Meth. Enzymol.* 225:890–900 (1993).

Sauer, B., "Site–specific recombination: developments and applications," *Curr. Op. Biotechnol.* 5:521–527 (Oct. 1994).

Sauer, B., "Multiplex Cre/lox recombination permits selective site–specific DNA targeting to both a natural and an engineered site in the yeast genome," *Nucl. Acids Res.* 24:4608–4613 (Dec. 1996).

Sauer, B., "Inducible Gene Targeting in Mice Using the Cre/lox system," *Methods* 14:381–392 (Apr. 1998).

Schindelhauer, D., and Cooke, H.J., "Efficient combination of large DNA in vitro: in gel site specific recombination (IGSSR) of PAC fragments containing $\alpha$ satellite DNA and the human HPRT gene locus," *Nucl. Acids Res.* 25:2241–2243 (Jun. 1997).

Schlake, T., and Bode, J., "Use of Mutated FLP Recognition Target (FRT) Sites for the Exchange of Expression Cassettes at Defined Chromosomal Loci," *Biochemistry* 33:12746–12751 (Nov. 1994).

Segall, A. M. and Nash, H. A., "Synaptic intermediates in bacteriophage lambda site–specific recombination: integrase can align pairs of attachment sites," *EMBO J.* 12:4567–4576 (1993).

Segall, A.M., and Nash, H.A., "Architectural flexibility in lambda site–specific recombination: three alternate conformations channel the attL site into three distinct pathways," *Gene to Cells* 1:453–463 (May 1996).

Sheffield, P. et al., "Overcoming Expression and Purification Problems of RhoGDI Using a Family of "Parallel" Expression Vectors," *Prot. Expr. Purif.* 15:34–39 (Feb. 1999).

Sizemore, C., et al., "Quantitative analysis of Tn10 Tet repressor binding to a complete set of tet operator mutants," *Nucl. Acids Res.* 18:2875–2880 (1990).

Smith, A. J. H., et al., "A site–directed chromosomal translocation induced in embryonic stem cells by Cre–loxP recombination," *Nat. Gen.* 9:376–385 (Apr. 1995).

Snaith, M.R., et al., "Multiple cloning sites carrying loxP and FRT recognition sites for the Cre and Flp site–specific recombinases," *Gene* 166:173–174 (Dec. 1995).

Spengler, S.J., et al., "The Stereostructure of Knots and Catenanes Produced by Phage $\lambda$ Integrative Recombination: Implications for Mechanism and DNA Structure," *Cell* 42:325–334 (1985).

Thompson, J. F., et al., "Mutations in an Integration Host Factor–Binding Site: Effect on Lambda Site–Specific Recombination and Regulatory Implications," *J. Bacteriol.* 168:1343–1351 (1986).

Thompson, J.F., et al., "Helical–repeat dependence of integrative recombination of bacteriophage $\lambda$: Role of the P1 and H1 protein binding sites," *Proc. Natl. Acad. Sci. USA* 85:6323–6327 (1988).

Tsurushita, N., et al., "Phage display vectors for in vivo recombination of immunoglobulin heavy and light chain genes to make large combinatorial libraries," *Gene* 172:59–63 (Jun. 1996).

Vanin, E.F., et al., "Development of High–Titer Retroviral Producer Cell Lines by Using Cre–Mediated Recombination," *J. Virol.* 71:7820–7826 (Oct. 1997).

Waterhouse, P., et al., "Combinatorial infection and in vivo recombination: a strategy for making large phage antibody repertoires," *Nucl. Acids Res.* 21:2265–2266 (1993).

Weisberg, R. A., and Landy, A., "Site–specific Recombination in Phage Lambda," in: "Lambda II," Hendrix, R. W. et al., eds., Cold Spring Harbor Laboratory Press, Cold Spring Harbor, N. Y., pp. 211–250 (1983).

Wierzbicki, A., et al., "A Mutational Analysis of the Bacteriophage P1 Recombinase Cre," *J. Mol. Biol.* 195:785–794 (1987).

Winoto, A., et al., "Directional Control of Site–specific Recombination by Bacteriophage $\lambda$," *J. Mol. Biol.* 192:677–680 (1986).

Yang, W., and Mizuuchi, K., "Site–specific recombination in plane view," *Structure* 5:1401–1406 (Nov. 1997).

Abremski, K., and Hoess, R., "Bacteriophage P1 Site–specific Recombination—Purification and PRoperties of the Cre Recombinase Protein," *J. Biol. Chem.* 259:1509–1514 (1984).

Bloch, C.A., et al., "Purification of *Escherichia coli* Chromosomal Segments without Cloning," *Biochem. Biophys. Res. Comm.* 223:104–111 (1996).

Bubeck, P., et al., "Rapid cloning by homologous recombination in vivo," *Nucl. Acids Res.* 21:3601–3602 (1993).

Chatterjee, P.K., and Coren, J.S., "Isolating large nested deletions in bacterial and P1 artificial chromosomes by in vivo P1 packaging of products o Cre–catalysed recombination between the endogenous and a transposed loxP site," *Nucl. Acids Res.* 25:2205–2212 (1997).

Degryse, E., "In vivo intermolecular recombination in *Escherichia coli*:application to plasmid constructions," *Gene* 170:45–50 (1996).

Guo, F., et al., "Asymmetric DNA bending in the Cre–loxP site–specific recombination synapse," *Proc. Natl. Acad. Sci. USA* 96:7143–7148 (1999).

Lafontaine, D., and Tollervey, D., "One–step PCR mediated strategy for the construction of conditionally expressed and epitope tagged yeast proteins," *Nucl. Acids Res.* 24:2469–2472 (1996).

Medberry, S.L., et al., "Intra–chromosomal rearrangements generated by Cre–lox site–specific recombination," *Nucl. Acids Res.* 23:485–490 (1995).

Oliner, J.D., et al., "In vivo cloning of PCR products in *E. coli*," *Nucl. Acids Res.* 21:5192–5197 (1993).

Osborne, B.I., et al., "A system for insertional mutagenesis and chromosomal rearrangement using the Ds transposon and Cre–lox," *Plant J.* 7:687–701 (1995).

Senecoff, J.F., et al., "DNA Recognition by the FLP Recombinase of the Yeast $2\mu$ Plasmid—A Mutational Analysis of the FLP Binding Site," *J. Mol. Biol.* 201:405–421 (1988).

Storck, T., et al., "Rapid construction in yeast of complex targeting vectors for gene manipulation in the mouse," *Nucl. Acids Res.* 24:4594–4596 (1996).

Strathmann, M., et al., "Transposon–facilitated DNA sequencing," *Proc. Natl. Acad. Sci. USA* 88:1247–1250 (1991).

Thorpe, H.M., and Smith, M.C.M., "In vitro site–specific integration of bacteriophage DNA catalyzed by a recombinase of the resolvase/invertase family," *Proc. Natl. Acad. Sci. USA* 96:5505–5510 (May 1998).

Wild, J., et al., "A broad–host–range in vivo pop–out and amplification system for generating large quantities of 50– to 100–kb genomic fragments for direct DNA sequencing," *Gene* 179:181–188 (1996).

Wild, J., et al., "Targeting and retrofitting pre–existing libraries of transposon insertions with FRT and oriV elements for in–vivo generation of large quantities of any genomic fragment," *Gene* 223:55–66 (1998).

Yoon, Y.G., et al., "Cre/loxP–mediated in vivo excision of large segments from yeast genome and their amplification based on the 2 $\mu$m plasmid–derived system," *Gene* 223:67–76 (1998).

York, D., et al., "Simple and efficient generation in vitro of nested deletions and inversions: Tn5 intramolecular transposition," *Nucl. Acids Res.* 26:1927–1933 (1998).

Zhu, X.–D., et al., "Homology Requirements for Ligation and Strand Exchange by the FLP Recombinase," *J. Biol. Chem.* 270:11646–11653 (1995).

Ausubel, F.M., et al., "Maps of Plasmids pBR322 and pUC19," in *Current Protocols in Molecular Biology*, John Wiley & Sons, Inc., Boston, MA, (1995).

Hoogenboom, H.R., et al., "Multi–subunit proteins on the surface of filamentous phage: methodologies for displaying antibody (Fab) heavy and light chains," *Nucl. Acids Res.* 19:4133–4137 (1991).

Yanisch–Perron, C., et al., "Improved M13 phage cloning vectors and host strains: nucleotide sequences of the M13mp18 and pUC19 vectors," *Gene* 33:103–119 (1985).

Wasserman, S.A., et al., "The helical repeat of double–stranded DNA varies as a function of catenation and supercoiling," *Nature* 334:448–450 (1988).

Babineau, D. et al., "The FLP Protein of the 2–micro Plasmid of Yeast," *J. Biol. Chem.* 260:12313–12391 (1985).

Cox, M.M., "The FLP protein of the yeast 2–$\mu$m plasmid: Expression of a eukaryotic genetic recombination system in *Escherichia coli*," *Proc. Natl. Acad. Sci. USA* 80:4223–4227 (1983).

Francia, M.V., et al., "Gene Integration in the *Escherichia coli* Chromosome Mediated by Tn21 Integrase (Int21)," *J. Bacteriol.* 178:894–898 (Feb. 1996).

Glasgow, A.C., et al., "DNA–binding Properties of the Hin Recombinase," *J. Biol. Chem.* 264:10072–10082 (1989).

Hoess, R.H., et al., "P1 site–specific recombination: Nucleotide sequence of the recombining sites," *Proc. Natl. Acad. Sci. USA* 79:3398–3402 (1982).

Hoess, R.H., et al., "Mechanism of Strand Cleavage and Exchange in the Cre–lox Site–specific Recombination System," *J. Mol. Biol.* 181:351–362 (1985).

Hoess, R., et al., "Formation of small circular DNA molecules via an in vitro site–specific recombination system," *Gene* 40:325–329 (1985).

Sternberg, N., et al., "Site–specific Recombination and Its Role in the Life Cycle of Bacteriophage P1," *Cold Spring Harbor Symp. Quant. Biol.* 45:297–309 (1981).

Sternberg, N., et al., "Bacteriophage P1 cre Gene and its Regulatory Region," *J. Mol. Biol.* 187:197–212 (1986).

Wang, G., et al., "pDUAL: A transposon–based cosmid cloning vector for generating nested deletions and DNA sequencing templates in vivo," *Proc. Natl. Acad. Sci. USA* 90:7874–7878 (1993).

\* cited by examiner

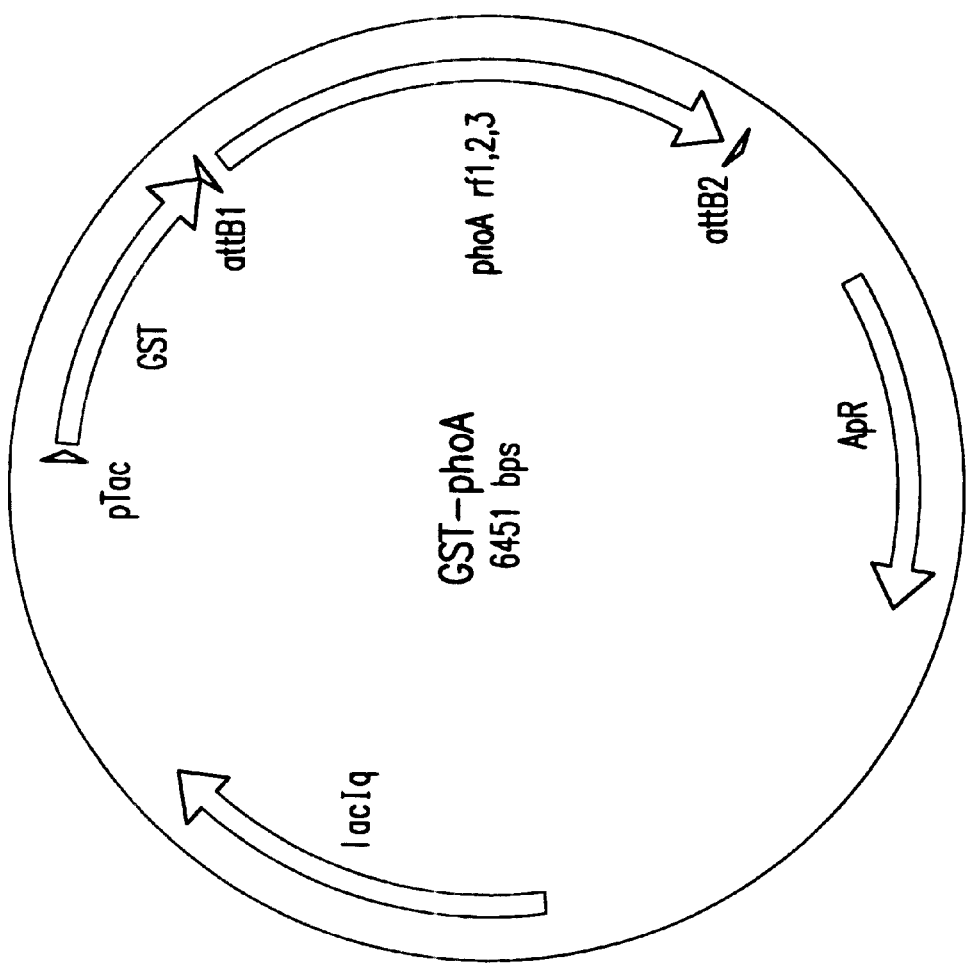

SEQUENCE LISTING (1) GENERAL INFORMATION:

(iii) NUMBER OF SEQUENCES: 35

(2) INFORMATION FOR SEQ ID NO:1:

(i) SEQUENCE CHARACTERISTICS:
        (A) LENGTH: 25 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:1:

RKYCWGCTTT YKTRTACNAA STSGB                                         25

(2) INFORMATION FOR SEQ ID NO:2:

(i) SEQUENCE CHARACTERISTICS:
        (A) LENGTH: 25 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:2:

AGCCWGCTTT YKTRTACNAA CTSGB                                         25

(2) INFORMATION FOR SEQ ID NO:3:

(i) SEQUENCE CHARACTERISTICS:
        (A) LENGTH: 25 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:3:

GTTCAGCTTT CKTRTACNAA CTSGB                                         25

(2) INFORMATION FOR SEQ ID NO:4:

(i) SEQUENCE CHARACTERISTICS:
        (A) LENGTH: 25 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:4:

AGCCWGCTTT CKTRTACNAA GTSGB                                         25

(2) INFORMATION FOR SEQ ID NO:5:

(i) SEQUENCE CHARACTERISTICS:
        (A) LENGTH: 25 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:5:

```
GTTCAGCTTT YKTRTACNAA GTSGB                                          25

(2) INFORMATION FOR SEQ ID NO:6:

(i) SEQUENCE CHARACTERISTICS:
        (A) LENGTH: 25 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:6:

AGCCTGCTTT TTTGTACAAA CTTGT                                          25

(2) INFORMATION FOR SEQ ID NO:7:

(i) SEQUENCE CHARACTERISTICS:
        (A) LENGTH: 25 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:7:

AGCCTGCTTT CTTGTACAAA CTTGT                                          25

(2) INFORMATION FOR SEQ ID NO:8:

(i) SEQUENCE CHARACTERISTICS:
        (A) LENGTH: 25 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:8:

ACCCAGCTTT CTTGTACAAA CTTGT                                          25

(2) INFORMATION FOR SEQ ID NO:9:

(i) SEQUENCE CHARACTERISTICS:
        (A) LENGTH: 25 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:9:

GTTCAGCTTT TTTGTACAAA CTTGT                                          25

(2) INFORMATION FOR SEQ ID NO:10:

(i) SEQUENCE CHARACTERISTICS:
        (A) LENGTH: 25 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:10:

GTTCAGCTTT CTTGTACAAA CTTGT                                          25
```

(2) INFORMATION FOR SEQ ID NO:11:

(i) SEQUENCE CHARACTERISTICS:
        (A) LENGTH: 25 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:11:

GTTCAGCTTT CTTGTACAAA GTTGG                                     25

(2) INFORMATION FOR SEQ ID NO:12:

(i) SEQUENCE CHARACTERISTICS:
        (A) LENGTH: 25 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:12:

AGCCTGCTTT TTTGTACAAA GTTGG                                     25

(2) INFORMATION FOR SEQ ID NO:13:

(i) SEQUENCE CHARACTERISTICS:
        (A) LENGTH: 25 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:13:

AGCCTGCTTT CTTGTACAAA GTTGG                                     25

(2) INFORMATION FOR SEQ ID NO:14:

(i) SEQUENCE CHARACTERISTICS:
        (A) LENGTH: 25 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:14:

ACCCAGCTTT CTTGTACAAA GTTGG                                     25

(2) INFORMATION FOR SEQ ID NO:15:

(i) SEQUENCE CHARACTERISTICS:
        (A) LENGTH: 25 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:15:

GTTCAGCTTT TTTGTACAAA GTTGG                                     25

(2) INFORMATION FOR SEQ ID NO:16:

(i) SEQUENCE CHARACTERISTICS:
        (A) LENGTH: 25 base pairs

```
            (B) TYPE: nucleic acid
            (C) STRANDEDNESS: both
            (D) TOPOLOGY: both (ii) MOLECULE TYPE: cDNA (xi) SEQUENCE DESCRIPTION: SEQ ID NO:16:

GTTCAGCTTT CTTGTACAAA GTTGG                                              25

(2) INFORMATION FOR SEQ ID NO:17:

(i) SEQUENCE CHARACTERISTICS:
            (A) LENGTH: 39 base pairs
            (B) TYPE: nucleic acid
            (C) STRANDEDNESS: both
            (D) TOPOLOGY: both (ii) MOLECULE TYPE: cDNA (xi) SEQUENCE DESCRIPTION: SEQ ID NO:17:

CCACCACAAA CGCGTCCATG GAATTACACT TTAATTTAG                                39

(2) INFORMATION FOR SEQ ID NO:18:

(i) SEQUENCE CHARACTERISTICS:
            (A) LENGTH: 39 base pairs
            (B) TYPE: nucleic acid
            (C) STRANDEDNESS: both
            (D) TOPOLOGY: both (ii) MOLECULE TYPE: cDNA (xi) SEQUENCE DESCRIPTION: SEQ ID NO:18:

CCACCACAAG TCGACGCATG CCGACAGCCT TCCAAATGT                                39

(2) INFORMATION FOR SEQ ID NO:19:

(i) SEQUENCE CHARACTERISTICS:
            (A) LENGTH: 46 base pairs
            (B) TYPE: nucleic acid
            (C) STRANDEDNESS: both
            (D) TOPOLOGY: both (ii) MOLECULE TYPE: cDNA (xi) SEQUENCE DESCRIPTION: SEQ ID NO:19:

GGCCGATTAC GATATCCCAA CGACCGAAAA CCTGTATTTT CAGGGT                        46

(2) INFORMATION FOR SEQ ID NO:20:

(i) SEQUENCE CHARACTERISTICS:
            (A) LENGTH: 30 base pairs
            (B) TYPE: nucleic acid
            (C) STRANDEDNESS: both
            (D) TOPOLOGY: both (ii) MOLECULE TYPE: cDNA (xi) SEQUENCE DESCRIPTION: SEQ ID NO:20:

CAGGTTTTCG GTCGTTGGGA TATCGTAATC                                         30

(2) INFORMATION FOR SEQ ID NO:21:

(i) SEQUENCE CHARACTERISTICS:
            (A) LENGTH: 47 base pairs
            (B) TYPE: nucleic acid
            (C) STRANDEDNESS: both
            (D) TOPOLOGY: both
```

(ii) MOLECULE TYPE: cDNA (xi) SEQUENCE DESCRIPTION: SEQ ID NO:21:

GGCCAGATTA CGATATCCCA ACGACCGAAA ACCTGTATTT TCAGGGT                47

(2) INFORMATION FOR SEQ ID NO:22:

(i) SEQUENCE CHARACTERISTICS:
        (A) LENGTH: 31 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:22:

CAGGTTTTCG GTCGTTGGGA TATCGTAATC T                                 31

(2) INFORMATION FOR SEQ ID NO:23:

(i) SEQUENCE CHARACTERISTICS:
        (A) LENGTH: 48 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:23:

GGCCAAGATT ACGATATCCC AACGACCGAA AACCTGTATT TTCAGGGT               48

(2) INFORMATION FOR SEQ ID NO:24:

(i) SEQUENCE CHARACTERISTICS:
        (A) LENGTH: 32 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:24:

CAGGTTTTCG GTCGTTGGGA TATCGTAATC TT                                32

(2) INFORMATION FOR SEQ ID NO:25:

(i) SEQUENCE CHARACTERISTICS:
        (A) LENGTH: 15 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:25:

ACCGTTTACG TGGAC                                                   15

(2) INFORMATION FOR SEQ ID NO:26:

(i) SEQUENCE CHARACTERISTICS:
        (A) LENGTH: 31 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:26:

```
TCGAGTCCAC GTAAACGGTT CCCACTTATT A                                              31
```

(2) INFORMATION FOR SEQ ID NO:27:

(i) SEQUENCE CHARACTERISTICS:
        (A) LENGTH: 39 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:27:

```
UAUUUUCAGG GUAUGGAGAA AAAAAUCACU GGAUAUACC                                      39
```

(2) INFORMATION FOR SEQ ID NO:28:

(i) SEQUENCE CHARACTERISTICS:
        (A) LENGTH: 33 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:28:

```
UCCCACUUAU UACGCCCCGC CCUGCCACUC AUC                                            33
```

(2) INFORMATION FOR SEQ ID NO:29:

(i) SEQUENCE CHARACTERISTICS:
        (A) LENGTH: 33 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:29:

```
UAUUUUCAGG GUAUGCCUGU UCUGGAAAAC CGG                                            33
```

(2) INFORMATION FOR SEQ ID NO:30:

(i) SEQUENCE CHARACTERISTICS:
        (A) LENGTH: 34 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:30:

```
UCCCACUUAU UAUUUCAGCC CCAGGGCGGC UUUC                                           34
```

(2) INFORMATION FOR SEQ ID NO:31:

(i) SEQUENCE CHARACTERISTICS:
        (A) LENGTH: 25 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:31:

```
AGCCTGCTTT TTTATACTAA CTTGA                                                     25
```

(2) INFORMATION FOR SEQ ID NO:32:

```
        (i) SEQUENCE CHARACTERISTICS:
            (A) LENGTH: 25 base pairs
            (B) TYPE: nucleic acid
            (C) STRANDEDNESS: both
            (D) TOPOLOGY: both (ii) MOLECULE TYPE: cDNA (xi) SEQUENCE DESCRIPTION: SEQ ID NO:32:

TCAAGTTAGT ATAAAAAAGC AGGCT                                                     25

(2) INFORMATION FOR SEQ ID NO:33:

(i) SEQUENCE CHARACTERISTICS:
            (A) LENGTH: 25 base pairs
            (B) TYPE: nucleic acid
            (C) STRANDEDNESS: both
            (D) TOPOLOGY: both (ii) MOLECULE TYPE: cDNA (xi) SEQUENCE DESCRIPTION: SEQ ID NO:33:

ACAAGTTTGT ACAAAAAAGC AGGCT                                                     25

(2) INFORMATION FOR SEQ ID NO:34:

(i) SEQUENCE CHARACTERISTICS:
            (A) LENGTH: 25 base pairs
            (B) TYPE: nucleic acid
            (C) STRANDEDNESS: both
            (D) TOPOLOGY: both (ii) MOLECULE TYPE: cDNA (xi) SEQUENCE DESCRIPTION: SEQ ID NO:34:

ACAAGTTTGT ACAAGAAAGC AGGCT                                                     25

(2) INFORMATION FOR SEQ ID NO:35:

(i) SEQUENCE CHARACTERISTICS:
            (A) LENGTH: 25 base pairs
            (B) TYPE: nucleic acid
            (C) STRANDEDNESS: both
            (D) TOPOLOGY: both (ii) MOLECULE TYPE: cDNA (xi) SEQUENCE DESCRIPTION: SEQ ID NO:35:

ACCACTTTGT ACAAGAAAGC TGGGT                                                     25
```

RECOMBINATIONAL CLONING USING ENGINEERED RECOMBINATION SITES

CROSS-REFERENCE TO RELATED APPLICATIONS

The present application is a continuation of U.S. application Ser. No. 08/663,002, filed Jun. 7, 1996 now U.S. Pat. No. 5,888,732, which is a continuation-in-part of U.S. application Ser. No. 08/486,139, filed Jun. 7, 1995 now abandoned, which applications are entirely incorporated herein by reference.

BACKGROUND OF THE INVENTION

1. Field of the Invention

The present invention relates to recombinant DNA technology. DNA and vectors having engineered recombination sites are provided for use in a recombinational cloning method that enables efficient and specific recombination of DNA segments using recombination proteins. The DNAs, vectors and methods are useful for a variety of DNA exchanges, such as subcloning of DNA, in vitro or in vivo.

2. Related Art

Site specific recombinases. Site specific recombinases are enzymes that are present in some viruses and bacteria and have been characterized to have both endonuclease and ligase properties. These recombinases (along with associated proteins in some cases) recognize specific sequences of bases in DNA and exchange the DNA segments flanking those segments. The recombinases and associated proteins are collectively referred to as "recombination proteins" (see, e.g.,, Landy, A., *Current Opinion in Biotechnology* 3:699–707 (1993)).

Numerous recombination systems from various organisms have been described. See, e.g., Hoess et al., *Nucleic Acids Research* 14(6):2287 (1986); Abremski et al., *J. Biol. Chem.* 261(1):391 (1986); Campbell, *J. Bacteriol.* 174(23): 7495 (1992); Qian et al., *J. Biol. Chem.* 267(11):7794 (1992); Araki et al., *J Mol. Biol.* 225(1):25 (1992); Maeser and Kahnmann (1991) *Mol. Gen. Genet.* 230:170–176).

Many of these belong to the integrase family of recombinases (Argos et al. *EMBO J.* 5:433–440 (1986)). Perhaps the best studied of these are the Integrase/att system from bacteriophage λ (Landy, A. *Current Opinions in Genetics and Devel.* 3:699–707 (1993)), the Cre/loxP system from bacteriophage P1 (Hoess and Abremski (1990) In *Nucleic Acids and Molecular Biology*, vol. 4. Eds.: Eckstein and Lilley, Berlin-Heidelberg: Springer-Verlag; pp. 90–109), and the FLP/FRT system from the Saccharomyces cerevisiae 2μ circle plasmid (Broach et al. *Cell* 29:227–234 (1982)).

Backman (U.S. Pat. No. 4,673,640) discloses the in vivo use of λ recombinase to recombine a protein producing DNA segment by enzymatic site-specific recombination using wild-type recombination sites attB and attP.

Hasan and Szybalski (*Gene* 56:145–151 (1987)) discloses the use of λ Int recombinase in vivo for intramolecular recombination between wild type attP and attB sites which flank a promoter. Because the orientations of these sites are inverted relative to each other, this causes an irreversible flipping of the promoter region relative to the gene of interest.

Palazzolo et al. *Gene* 88:25–36 (1990), discloses phage lambda vectors having bacteriophage λ arms that contain restriction sites positioned outside a cloned DNA sequence and between wild-type loxP sites. Infection of *E. coli* cells that express the Cre recombinase with these phage vectors results in recombination between the loxP sites and the in vivo excision of the plasmid replicon, including the cloned cDNA.

Pósfai et al. (*Nucl. Acids Res.* 22:2392–2398 (1994)) discloses a method for inserting into genomic DNA partial expression vectors having a selectable marker, flanked by two wild-type FRT recognition sequences. FLP site-specific recombinase as present in the cells is used to integrate the vectors into the genome at predetermined sites. Under conditions where the replicon is functional, this cloned genomic DNA can be amplified.

Bebee et al. (U.S. Pat. No. 5,434,066) discloses the use of site-specific recombinases such as Cre for DNA containing two loxP sites is used for in vivo recombination between the sites.

Boyd (*Nucl. Acids Res.* 21:817–821 (1993)) discloses a method to facilitate the cloning of blunt-ended DNA using conditions that encourage intermolecular ligation to a dephosphorylated vector that contains a wild-type loxP site acted upon by a Cre site-specific recombinase present in *E. coli* host cells.

Waterhouse et al. (PCT No. 93/19172 and *Nucleic Acids Res.* 21 (9):2265 (1993)) disclose an in vivo method where light and heavy chains of a particular antibody were cloned in different phage vectors between loxP and loxP 511 sites and used to transfect new *E. coli* cells. Cre, acting in the host cells on the two parental molecules (one plasmid, one phage), produced four products in equilibrium: two different cointegrates (produced by recombination at either loxP or loxP 511 sites), and two daughter molecules, one of which was the desired product.

In contrast to the other related art, Schlake & Bode (*Biochemistry* 33:12746–12751 (1994)) discloses an in vivo method to exchange expression cassettes at defined chromosomal locations, each flanked by a wild type and a spacer-mutated FRT recombination site. A double-reciprocal crossover was mediated in cultured mammalian cells by using this FLP/FRT system for site-specific recombination.

Transposases. The family of enzymes, the transposases, has also been used to transfer genetic information between replicons. Transposons are structurally variable, being described as simple or compound, but typically encode the recombinase gene flanked by DNA sequences organized in inverted orientations. Integration of transposons can be random or highly specific. Representatives such as Tn7, which are highly site-specific, have been applied to the in vivo movement of DNA segments between replicons (Lucklow et al., *J. Virol.* 67:4566–4579 (1993)).

Devine and Boeke *Nucl. Acids Res.* 22:3765–3772 (1994), discloses the construction of artificial transposons for the insertion of DNA segments, in vitro, into recipient DNA molecules. The system makes use of the integrase of yeast TY1 virus-like particles. The DNA segment of interest is cloned, using standard methods, between the ends of the transposon-like element TY1. In the presence of the TY1 integrase, the resulting element integrates randomly into a second target DNA molecule.

DNA cloning. The cloning of DNA segments currently occurs as a daily routine in many research labs and as a prerequisite step in many genetic analyses. The purpose of these clonings is various, however, two general purposes can be considered: (1) the initial cloning of DNA from large DNA or RNA segments (chromosomes, YACs, PCR fragments, mRNA, etc.), done in a relative handful of known vectors such as pUC, pGem, pBlueScript, and (2) the subcloning of these DNA segments into specialized vectors for functional analysis. A great deal of time and effort is expended both in the initial cloning of DNA segments and in the transfer of DNA segments from the initial cloning vectors to the more specialized vectors. This transfer is called subcloning.

The basic methods for cloning have been known for many years and have changed little during that time. A typical cloning protocol is as follows:

(1) digest the DNA of interest with one or two restriction enzymes;
(2) gel purify the DNA segment of interest when known;
(3) prepare the vector by cutting with appropriate restriction enzymes, treating with alkaline phosphatase, gel purify etc., as appropriate;
(4) ligate the DNA segment to vector, with appropriate controls to estimate background of uncut and self-ligated vector;
(5) introduce the resulting vector into an E. coli host cell;
(6) pick selected colonies and grow small cultures overnight;
(7) make DNA minipreps; and
(8) analyze the isolated plasmid on agarose gels (often after diagnostic restriction enzyme digestions) or by PCR.

The specialized vectors used for subcloning DNA segments are functionally diverse. These include but are not limited to: vectors for expressing genes in various organisms; for regulating gene expression; for providing tags to aid in protein purification or to allow tracking of proteins in cells; for modifying the cloned DNA segment (e.g., generating deletions); for the synthesis of probes (e.g., riboprobes); for the preparation of templates for DNA sequencing; for the identification of protein coding regions; for the fusion of various protein-coding regions; to provide large amounts of the DNA of interest, etc. It is common that a particular investigation will involve subcloning the DNA segment of interest into several different specialized vectors.

As known in the art, simple subclonings can be done in one day (e.g., the DNA segment is not large and the restriction sites are compatible with those of the subcloning vector). However, many other subclonings can take several weeks, especially those involving unknown sequences, long fragments, toxic genes, unsuitable placement of restriction sites, high backgrounds, impure enzymes, etc. Subcloning DNA fragments is thus often viewed as a chore to be done as few times as possible.

Several methods for facilitating the cloning of DNA segments have been described, e.g., as in the following references.

Ferguson, J., et al. *Gene* 16:191 (1981), discloses a family of vectors for subcloning fragments of yeast DNA. The vectors encode kanamycin resistance. Clones of longer yeast DNA segments can be partially digested and ligated into the subcloning vectors. If the original cloning vector conveys resistance to ampicillin, no purification is necessary prior to transformation, since the selection will be for kanamycin.

Hashimoto-Gotoh, T., et al. *Gene* 41:125 (1986), discloses a subcloning vector with unique cloning sites within a streptomycin sensitivity gene; in a streptomycin-resistant host, only plasmids with inserts or deletions in the dominant sensitivity gene will survive streptomycin selection.

Accordingly, traditional subcloning methods, using restriction enzymes and ligase, are time consuming and relatively unreliable. Considerable labor is expended, and if two or more days later the desired subclone can not be found among the candidate plasmids, the entire process must then be repeated with alternative conditions attempted. Although site specific recombinases have been used to recombine DNA in vivo, the successful use of such enzymes in vitro was expected to suffer from several problems. For example, the site specificities and efficiencies were expected to differ in vitro; topologically-linked products were expected; and the topology of the DNA substrates and recombination proteins was expected to differ significantly in vitro (see, e.g., Adams et al, *J. Mol. Biol.* 226:661–73 (1992)). Reactions that could go on for many hours in vivo were expected to occur in significantly less time in vitro before the enzymes became inactive. Multiple DNA recombination products were expected in the biological host used, resulting in unsatisfactory reliability, specificity or efficiency of subcloning. In vitro recombination reactions were not expected to be sufficiently efficient to yield the desired levels of product.

Accordingly, there is a long felt need to provide an alternative subcloning system that provides advantages over the known use of restriction enzymes and ligases.

SUMMARY OF THE INVENTION

The present invention provides nucleic acid, vectors and methods for obtaining chimeric nucleic acid using recombination proteins and engineered recombination sites, in vitro or in vivo. These methods are highly specific, rapid, and less labor intensive than what is disclosed or suggested in the related background art. The improved specificity, speed and yields of the present invention facilitates DNA or RNA subcloning, regulation or exchange useful for any related purpose. Such purposes include in vitro recombination of DNA segments and in vitro or in vivo insertion or modification of transcribed, replicated, isolated or genomic DNA or RNA.

The present invention relates to nucleic acids, vectors and methods for moving or exchanging segments of DNA using at least one engineered recombination site and at least one recombination protein to provide chimeric DNA molecules which have the desired characteristic(s) and/or DNA segment(s). Generally, one or more parent DNA molecules are recombined to give one or more daughter molecules, at least one of which is the desired Product DNA segment or vector. The invention thus relates to DNA, RNA, vectors and methods to effect the exchange and/or to select for one or more desired products.

One embodiment of the present invention relates to a method of making chimeric DNA, which comprises (a) combining in vitro or in vivo
  (i) an Insert Donor DNA molecule, comprising a desired DNA segment flanked by a first recombination site and a second recombination site, wherein the first and second recombination sites do not recombine with each other;
  (ii) a Vector Donor DNA molecule containing a third recombination site and a fourth recombination site, wherein the third and fourth recombination sites do not recombine with each other; and
  (iii) one or more site specific recombination proteins capable of recombining the first and third recombinational sites and/or the second and fourth recombinational sites;

thereby allowing recombination to occur, so as to produce at least one Cointegrate DNA molecule, at least one desired Product DNA molecule which comprises said desired DNA segment, and optionally a Byproduct DNA molecule; and then, optionally, (b) selecting for the Product or Byproduct DNA molecule.

Another embodiment of the present invention relates to a kit comprising a carrier or receptacle being compartmentalized to receive and hold therein at least one container, wherein a first container contains a DNA molecule comprising a vector having at least two recombination sites flanking a cloning site or a Selectable marker, as described herein. The kit optionally further comprises:

(i) a second container containing a Vector Donor plasmid comprising a subcloning vector and/or a Selectable marker of which one or both are flanked by one or more engineered recombination sites; and/or (ii) a third container containing at least one recombination protein which recognizes and is capable of recombining at least one of said recombination sites.

Other embodiments include DNA and vectors useful in the methods of the present invention. In particular, Vector Donor molecules are provided in one embodiment, wherein DNA segments within the Vector Donor are separated either by, (i) in a circular Vector Donor, at least two recombination sites, or (ii) in a linear Vector Donor, at least one recombination site, where the recombination sites are preferably engineered to enhance specificity or efficiency of recombination.

One Vector Donor embodiment comprises a first DNA segment and a second DNA segment, the first or second segment comprising a Selectable marker. A second Vector Donor embodiment comprises a first DNA segment and a second DNA segment, the first or second DNA segment comprising a toxic gene. A third Vector Donor embodiment comprises a first DNA segment and a second DNA segment, the first or second DNA segment comprising an inactive fragment of at least one Selectable marker, wherein the inactive fragment of the Selectable marker is capable of reconstituting a functional Selectable marker when recombined across the first or second recombination site with another inactive fragment of at least one Selectable marker.

The present recombinational cloning method possesses several advantages over previous in vivo methods. Since single molecules of recombination products can be introduced into a biological host, propagation of the desired Product DNA in the absence of other DNA molecules (e.g., starting molecules, intermediates, and by-products) is more readily realized. Reaction conditions can be freely adjusted in vitro to optimize enzyme activities. DNA molecules can be incompatible with the desired biological host (e.g., YACs, genomic DNA, etc.), can be used. Recombination proteins from diverse sources can be employed, together or sequentially.

Other embodiments will be evident to those of ordinary skill in the art from the teachings contained herein in combination with what is known to the art.

BRIEF DESCRIPTION OF THE FIGURES

FIG. 8J depicts a vector diagram of GST-phoA.

DETAILED DESCRIPTION OF THE PREFERRED EMBODIMENTS

It is unexpectedly discovered in the present invention that subcloning reactions can be provided using recombinational cloning. Recombination cloning according to the present invention uses DNAs, vectors and methods, in vitro and in vivo, for moving or exchanging segments of DNA molecules using engineered recombination sites and recombination proteins. These methods provide chimeric DNA molecules that have the desired characteristic(s) and/or DNA segment(s).

The present invention thus provides nucleic acid, vectors and methods for obtaining chimeric nucleic acid using recombination proteins and engineered recombination sites, in vitro or in vivo. These methods are highly specific, rapid, and less labor intensive than what is disclosed or suggested in the related background art. The improved specificity, speed and yields of the present invention facilitates DNA or RNA subcloning, regulation or exchange useful for any related purpose. Such purposes include in vitro recombination of DNA segments and in vitro or in vivo insertion or modification of transcribed, replicated, isolated or genomic DNA or RNA.

Definitions

In the description that follows, a number of terms used in recombinant DNA technology are utilized extensively. In order to provide a clear and consistent understanding of the specification and claims, including the scope to be given such terms, the following definitions are provided.

Byproduct: is a daughter molecule (a new clone produced after the second recombination event during the recombinational cloning process) lacking the DNA which is desired to be subcloned.

Cointegrate: is at least one recombination intermediate DNA molecule of the present invention that contains both parental (starting) DNA molecules. It will usually be circular. In some embodiments it can be linear.

Host: is any prokaryotic or eukaryotic organism that can be a recipient of the recombinational cloning Product. A "host," as the term is used herein, includes prokaryotic or eukaryotic organisms that can be genetically engineered. For examples of such hosts, see Maniatis et al., *Molecular Cloning: A Laboratory Manual*, Cold Spring Harbor Laboratory, Cold Spring Harbor, N.Y. (1982).

Insert: is the desired DNA segment (segment A of FIG. 1) which one wishes to manipulate by the method of the present invention. The insert can have one or more genes.

Insert Donor: is one of the two parental DNA molecules of the present invention which carries the Insert. The Insert Donor DNA molecule comprises the Insert flanked on both sides with recombination signals. The Insert Donor can be linear or circular. In one embodiment of the invention, the Insert Donor is a circular DNA molecule and further comprises a cloning vector sequence outside of the recombination signals (see FIG. 1).

Figure 1:
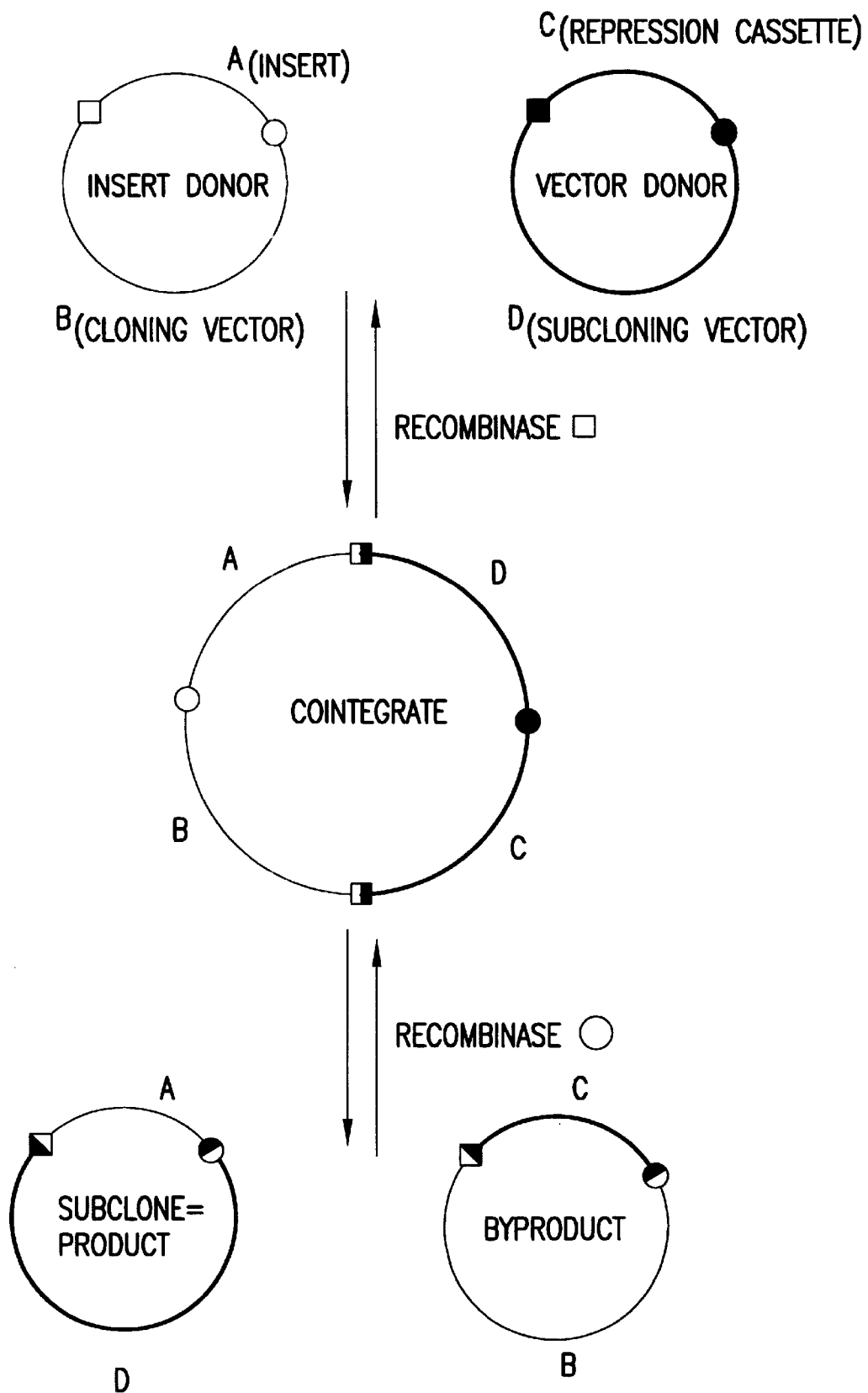
FIG. 1 depicts one general method of the present invention, wherein the starting (parent) DNA molecules can be circular or linear. The goal is to exchange the new subcloning vector D for the original cloning vector B. It is desirable in one embodiment to select for AD and against all the other molecules, including the Cointegrate. The square and circle are sites of recombination: e.g., loxP sites, att sites, etc. For example, segment D can contain expression signals, new drug markers, new origins of replication, or specialized functions for mapping or sequencing DNA.

Product: is one or both the desired daughter molecules comprising the A and D or B and C sequences which are produced after the second recombination event during the recombinational cloning process (see FIG. 1). The Product contains the DNA which was to be cloned or subcloned.

Promoter: is a DNA sequence generally described as the 5'-region of a gene, located proximal to the start codon. The transcription of an adjacent DNA segment is initiated at the promoter region. A repressible promoter's rate of transcription decreases in response to a repressing agent. An inducible promoter's rate of transcription increases in response to an inducing agent. A constitutive promoter's rate of transcription is not specifically regulated, though it can vary under the influence of general metabolic conditions.

Recognition sequence: Recognition sequences are particular DNA sequences which a protein, DNA, or RNA molecule (e.g., restriction endonuclease, a modification methylase, or a recombinase) recognizes and binds. For example, the recognition sequence for Cre recombinase is loxP which is a 34 base pair sequence comprised of two 13 base pair inverted repeats (serving as the recombinase binding sites) flanking an 8 base pair core sequence. See FIG. 1 of Sauer, B., *Current Opinion in Biotechnology* 5:521–527 (1994). Other examples of recognition sequences are the attB, attP, attL, and attR sequences which are recognized by the recombinase enzyme λ Integrase. attB is an approximately 25 base pair sequence containing two 9 base pair core-type Int binding sites and a 7 base pair overlap region. attP is an approximately 240 base pair sequence containing core-type Int binding sites and arm-type Int binding sites as well as sites for auxiliary proteins IHF, FIS, and Xis. See Landy, *Current Opinion in Biotechnology* 3:699–707 (1993). Such sites are also engineered according to the present invention to enhance methods and products.

Recombinase: is an enzyme which catalyzes the exchange of DNA segments at specific recombination sites.

Recombinational Cloning: is a method described herein, whereby segments of DNA molecules are exchanged, inserted, replaced, substituted or modified, in vitro or in vivo.

Recombination proteins: include excisive or integrative proteins, enzymes, co-factors or associated proteins that are involved in recombination reactions involving one or more recombination sites. See, Landy (1994), infra.

Repression cassette: is a DNA segment that contains a repressor of a Selectable marker present in the subcloning vector.

Selectable marker: is a DNA segment that allows one to select for or against a molecule or a cell that contains it, often under particular conditions. These markers can encode an activity, such as, but not limited to, production of RNA, peptide, or protein, or can provide a binding site for RNA, peptides, proteins, inorganic and organic compounds or compositions and the like. Examples of Selectable markers include but are not limited to: (1) DNA segments that encode products which provide resistance against otherwise toxic compounds (e.g., antibiotics); (2) DNA segments that encode products which are otherwise lacking in the recipient cell (e.g., tRNA genes, auxotrophic markers); (3) DNA segments that encode products which suppress the activity of a gene product; (4) DNA segments that encode products which can be readily identified (e.g., phenotypic markers such as β-galactosidase, green fluorescent protein (GFP), and cell surface proteins); (5) DNA segments that bind products which are otherwise detrimental to cell survival and/or function; (6) DNA segments that otherwise inhibit the activity of any of the DNA segments described in Nos. 1–5 above (e.g., antisense oligonucleotides); (7) DNA segments that bind products that modify a substrate (e.g. restriction endonucleases); (8) DNA segments that can be used to isolate a desired molecule (e.g. specific protein binding sites); (9) DNA segments that encode a specific nucleotide sequence which can be otherwise non-functional (e.g., for PCR amplification of subpopulations of molecules); and/or (10) DNA segments, which when absent, directly or indirectly confer sensitivity to particular compounds.

Selection scheme: is any method which allows selection, enrichment, or identification of a desired Product or Product(s) from a mixture containing the Insert Donor, Vector Donor, and/or any intermediates, (e.g. a Cointegrate) Byproducts. The selection schemes of one preferred embodiment have at least two components that are either linked or unlinked during recombinational cloning. One component is a Selectable marker. The other component controls the expression in vitro or in vivo of the Selectable marker, or survival of the cell harboring the plasmid carrying the Selectable marker. Generally, this controlling element will be a repressor or inducer of the Selectable marker, but other means for controlling expression of the Selectable marker can be used. Whether a repressor or activator is used will depend on whether the marker is for a positive or negative selection, and the exact arrangement of the various DNA segments, as will be readily apparent to those skilled in the art A. preferred requirement is that the selection scheme results in selection of or enrichment for only one or more desired Products. As defined herein to select for a DNA molecule includes (a) selecting or enriching for the presence of the desired DNA molecule, and (b) selecting or enriching against the presence of DNA molecules that are not the desired DNA molecule.

In one embodiment, the selection schemes (which can be carried out reversed) will take one of three forms, which will be discussed in terms of FIG. 1. The first, exemplified herein with a Selectable marker and a repressor therefor, selects for molecules having segment D and lacking segment C. The second selects against molecules having segment C and for molecules having segment D. Possible embodiments of the second form would have a DNA segment carrying a gene toxic to cells into which the in vitro reaction products are to be introduced. A toxic gene can be a DNA that is expressed as a toxic gene product (a toxic protein or RNA), or can be toxic in and of itself. (In the latter case, the toxic gene is understood to carry its classical definition of "heritable trait".)

Examples of such toxic gene products are well known in the art, and include, but are not limited to, restriction endonucleases (e.g., DpnI) and genes that kill hosts in the absence of a suppressing function, e.g., kicB. A toxic gene can alternatively be selectable in vitro, e.g., a restriction site.

In the second form, segment D carries a Selectable marker. The toxic gene would eliminate transformants harboring the Vector Donor, Cointegrate, and Byproduct molecules, while the Selectable marker can be used to select for cells containing the Product and against cells harboring only the Insert Donor.

The third form selects for cells that have both segments A and D in cis on the same molecule, but not for cells that have both segments in trans on different molecules. This could be embodied by a Selectable marker that is split into two inactive fragments, one each on segments A and D.

The fragments are so arranged relative to the recombination sites that when the segments are brought together by the recombination event, they reconstitute a functional Selectable marker. For example, the recombinational event can link a promoter with a structural gene, can link two fragments of a structural gene, or can link genes that encode a heterodimeric gene product needed for survival, or can link portions of a replicon.

Site-specific recombinase: is a type of recombinase which typically has at least the following four activities: (1) recognition of one or two specific DNA sequences; (2) cleavage of said DNA sequence or sequences; (3) DNA topoisomerase activity involved in strand exchange; and (4) DNA ligase activity to reseal the cleaved strands of DNA. See Sauer, B., *Current Opinions in Biotechnology* 5:521–527 (1994). Conservative site-specific recombination is distinguished from homologous recombination and transposition by a high degree of specificity for both partners. The strand exchange mechanism involves the cleavage and rejoining of specific DNA sequences in the absence of DNA synthesis (Landy, A. (1989) *Ann. Rev. Biochem.* 58:913–949).

Subcloning vector: is a cloning vector comprising a circular or linear DNA molecule which includes an appropriate replicon. In the present invention, the subcloning vector (segment D in FIG. 1) can also contain functional and/or regulatory elements that are desired to be incorporated into the final product to act upon or with the cloned DNA Insert (segment A in FIG. 1). The subcloning vector can also contain a Selectable marker (contained in segment C in FIG. 1).

Vector: is a DNA that provides a useful biological or biochemical property to an Insert. Examples include plasmids, phages, and other DNA sequences which are able to replicate or be replicated in vitro or in a host cell, or to convey a desired DNA segment to a desired location within a host cell. A Vector can have one or more restriction endonuclease recognition sites at which the DNA sequences can be cut in a determinable fashion without loss of an essential biological function of the vector, and into which a DNA fragment can be spliced in order to bring about its replication and cloning. Vectors can further provide primer sites, e.g., for PCR, transcriptional and/or translational initiation and/or regulation sites, recombinational signals, replicons, Selectable markers, etc. Clearly, methods of inserting a desired DNA fragment which do not require the use of homologous recombination or restriction enzymes (such as, but not limited to, UDG cloning of PCR fragments (U.S. Pat. No. 5,334,575, entirely incorporated herein by reference), TA Cloning® brand PCR cloning (Invitrogen Corp., Carlsbad, Calif. also known as direct ligation cloning and the like) can also be applied to clone a fragment of DNA into a cloning vector to be used according to the present invention. The cloning vector can further contain a Selectable marker suitable for use in the identification of cells transformed with the cloning vector.

Vector Donor: is one of the two parental DNA molecules of the present invention which carries the DNA segments encoding the DNA vector which is to become part of the desired Product. The Vector Donor comprises a subcloning vector D (or it can be called the cloning vector if the Insert Donor does not already contain a cloning vector) and a segment C flanked by recombination sites (see FIG. 1). Segments C and/or D can contain elements that contribute to selection for the desired Product daughter molecule, as described above for selection schemes. The recombination signals can be the same or different, and can be acted upon by the same or different recombinases. In addition, the Vector Donor can be linear or circular.

Description

One general scheme for an in vitro or in vivo method of the invention is shown in FIG. 1, where the Insert Donor and the Vector Donor can be either circular or linear DNA, but is shown as circular. Vector D is exchanged for the original cloning vector A. It is desirable to select for the daughter vector containing elements A and D and against other molecules, including one or more Cointegrate(s). The square and circle are different sets of recombination sites (e.g., lox sites or att sites). Segment A or D can contain at least one Selection Marker, expression signals, origins of replication, or specialized functions for detecting, selecting, expressing, mapping or sequencing DNA, where D is used in this example.

Examples of desired DNA segments that can be part of Element A or D include, but are not limited to, PCR products, large DNA segments, genomic clones or fragments, cDNA clones, functional elements, etc., and genes or partial genes, which encode useful nucleic acids or proteins. Moreover, the recombinational cloning of the present invention can be used to make ex vivo and in vivo gene transfer vehicles for protein expression and/or gene therapy.

In FIG. 1, the scheme provides the desired Product as containing vectors D and A, as follows. The Insert Donor (containing A and B) is first recombined at the square recombination sites by recombination proteins, with the Vector Donor (containing C and D), to form a Co-integrate having each of A-D-C-B. Next, recombination occurs at the circle recombination sites to form Product DNA (A and D) and Byproduct DNA (C and B). However, if desired, two or more different Co-integrates can be formed to generate two or more Products.

In one embodiment of the present in vitro or in vivo recombinational cloning method, a method for selecting at least one desired Product DNA is provided. This can be understood by consideration of the map of plasmid pEZC726 depicted in FIG. 2. The two exemplary recombination sites are attP and loxP. On one segment defined by these sites is a kanamycin resistance gene whose promoter has been replaced by the tetOP operator/promoter from transposon Tn10. In the absence of tet repressor protein, *E. coli* RNA polymerase transcribes the kanamycin resistance gene from the tetOP. If tet repressor is present, it binds to tetOP and blocks transcription of the kanamycin resistance gene. The other segment of pEZC726 has the tet repressor gene expressed by a constitutive promoter. Thus cells transformed by pEZC726 are resistant to chloramphenicol, because of the chloramphenicol acetyl transferase gene on the same segment as tetR, but are sensitive to kanamycin. The recombination reactions result in separation of the tetR gene from the regulated kanamycin resistance gene. This separation results in kanamycin resistance in cells receiving the desired recombination Product.

Two different sets of plasmids were constructed to demonstrate the in vitro method. One set, for use with Cre recombinase only (cloning vector 602 and subcloning vector 629 (FIG. 3)) contained loxP and loxP 511 sites. A second set, for use with Cre and integrase (cloning vector 705 and subcloning vector 726 (FIG. 2)) contained loxP and att sites. The efficiency of production of the desired daughter plasmid was about 60 fold higher using both enzymes than using Cre alone. Nineteen of twenty four colonies from the Cre-only reaction contained the desired product, while thirty eight of thirty eight colonies from the integrase plus Cre reaction contained the desired product plasmid.

Other Selection Schemes

A variety of selection schemes can be used that are known in the art as they can suit a particular purpose for which the recombinational cloning is carried out. Depending upon individual preferences and needs, a number of different types of selection schemes can be used in the recombinational cloning method of the present invention. The skilled artisan can take advantage of the availability of the many DNA segments or methods for making them and the different methods of selection that are routinely used in the art. Such DNA segments include but are not limited to those which encodes an activity such as, but not limited to, production of RNA, peptide, or protein, or providing a binding site for such RNA, peptide, or protein. Examples of DNA molecules used in devising a selection scheme are given above, under the definition of "selection scheme".

Additional examples include but are not limited to:

(i) Generation of new primer sites for PCR (e.g., juxtaposition of two DNA sequences that were not previously juxtaposed);

(ii) Inclusion of a DNA sequence acted upon by a restriction endonuclease or other DNA modifying enzyme, chemical, ribozyme, etc.;

(iii) Inclusion of a DNA sequence recognized by a DNA binding protein, RNA, DNA, chemical, etc.) (e.g., for use as an affinity tag for selecting for or excluding from a population) (Davis, *Nucl. Acids Res.* 24:702–706 (1996); *J. Virol.* 69: 8027–8034 (1995));

(iv) In vitro selection of RNA ligands for the ribosomal L22 protein associated with Epstein-Barr virus-expressed RNA by using randomized and cDNA-derived RNA libraries;

(vi) The positioning of functional elements whose activity requires a specific orientation or juxtaposition (e.g., (a) a recombination site which reacts poorly in trans, but when placed in cis, in the presence of the appropriate proteins, results in recombination that destroys certain populations of molecules; (e.g., reconstitution of a promoter sequence that allows in vitro RNA synthesis). The RNA can be used directly, or can be reverse transcribed to obtain the desired DNA construct;

(vii) Selection of the desired product by size (e.g. fractionation) or other physical property of the molecule(s); and (viii) Inclusion of a DNA sequence required for a specific modification (e.g., methylation) that allows its identification.

After formation of the Product and Byproduct in the method of the present invention, the selection step can be carried out either in vitro or in vivo depending upon the particular selection scheme which has been optionally devised in the particular recombinational cloning procedure.

For example, an in vitro method of selection can be devised for the Insert Donor and Vector Donor DNA molecules. Such scheme can involve engineering a rare restriction site in the starting circular vectors in such a way that after the recombination events the rare cutting sites end up in the Byproduct Hence, when the restriction enzyme which binds and cuts at the rare restriction site is added to the reaction mixture in vitro, all of the DNA molecules carrying the rare cutting site, i.e., the starting DNA molecules, the Cointegrate, and the Byproduct, will be cut and rendered nonreplicable in the intended host cell. For example, cutting sites in segments B and C (see FIG. 1) can be used to select against all molecules except the Product. Alternatively, only a cutting site in C is needed if one is able to select for segment D, e.g., by a drug resistance gene not found on B.

Similarly, an in vitro selection method can be devised when dealing with linear DNA molecules. DNA sequences complementary to a PCR primer sequence can be so engineered that they are transferred, through the recombinational cloning method, only to the Product molecule. After the reactions are completed, the appropriate primers are added to the reaction solution and the sample is subjected to PCR Hence, all or part of the Product molecule is amplified.

Other in vivo selection schemes can be used with a variety of *E. coli* cell lines. One is to put a repressor gene on one segment of the subcloning plasmid, and a drug marker controlled by that repressor on the other segment of the same plasmid. Another is to put a killer gene on segment C of the subcloning plasmid (FIG. 1). Of course a way must exist for growing such a plasmid, ie., there must exist circumstances under which the killer gene will not kill. There are a number of these genes known which require particular strains of *E. coli*. One such scheme is to use the restriction enzyme DpnI, which will not cleave unless its recognition sequence GATC is methylated. Many popular common *E. Coli* strains methylate GATC sequences, but there are mutants in which cloned DpnI can be expressed without harm.

Of course analogous selection schemes can be devised for other host organisms. For example, the tet repressor/operator of Tn10 has been adapted to control gene expression in eukaryotes (Gossen, M., and Bujard, H., *Proc. Natl. Acad. Sci. USA* 89:5547–5551 (1992)). Thus the same control of drug resistance by the tet repressor exemplified herein can be applied to select for Product in eukaryotic cells.

Recombination Proteins

In the present invention, the exchange of DNA segments is achieved by the use of recombination proteins, including recombinases and associated co-factors and proteins. Various recombination proteins are described in the art. Examples of such recombinases include:

Cre: A protein from bacteriophage P1 (Abremski and Hoess, *J. Biol. Chem.* 259(3):1509–1514 (1984)) catalyzes the exchange (i.e., causes recombination) between 34 bp DNA sequences called loxP (locus of crossover) sites (See Hoess et al., *Nucl. Acids Res.* 14(5):2287 (1986)). Cre is available commercially (Novagen, Catalog No. 69247-1). Recombination mediated by Cre is freely reversible. From thermodynamic considerations it is not surprising that Cre-mediated integration (recombination between two molecules to form one molecule) is much less efficient than Cre-mediated excision (recombination between two loxP sites in the same molecule to form two daughter molecules). Cre works in simple buffers with either magnesium or spermidine as a cofactor, as is well known in the art. The DNA substrates can be either linear or supercoiled. A number of mutant loxP sites have been described (Hoess et al., supra). One of these, loxP 511, recombines with another loxP 511 site, but will not recombine with a loxP site.

Integrase: A protein from bacteriophage lambda that mediates the integration of the lambda genome into the *E. coli* chromosome. The bacteriophage λ Int recombinational proteins promote irreversible recombination between its substrate att sites as part of the formation or induction of a lysogenic state. Reversibility of the recombination reactions results from two independent pathways for integrative and excisive recombination. Each pathway uses a unique, but overlapping, set of the 15 protein binding sites that comprise att site DNAs. Cooperative and competitive interactions involving four proteins (Int, Xis, IHF and FIS) determine the direction of recombination.

Integrative recombination involves the Int and IHF proteins and sites attP (240 bp) and attB (25 bp). Recombination results in the formation of two new sites: attL and attR. Excisive recombination requires Int, IHF, and Xis, and sites attL and attR to generate attP and attB. Under certain conditions, FIS stimulates excisive recombination. In addition to these normal reactions, it should be appreciated that attP and attB, when placed on the same molecule, can promote excisive recombination to generate two excision products, one with attL and one with attR. Similarly, intermolecular recombination between molecules containing attL and attR, in the presence of Int, IHF and Xis, can result in integrative recombination and the generation attP and attB. Hence, by flanking DNA segments with appropriate combinations of engineered att sites, in the presence of the appropriate recombination proteins, one can direct excisive or integrative recombination, as reverse reactions of each other.

Each of the att sites contains a 15 bp core sequence; individual sequence elements of functional significance lie within, outside, and across the boundaries of this common core (Landy, A., *Ann. Rev. Biochem.* 58:913 (1989)). Efficient recombination between the various att sites requires that the sequence of the central common region be identical between the recombining partners, however, the exact sequence is now found to be modifiable. Consequently, derivatives of the att site with changes within the core are now discovered to recombine as least as efficiently as the native core sequences.

Integrase acts to recombine the attP site on bacteriophage lambda (about 240 bp) with the attB site on the *E. coli* genome (about 25 bp) (Weisberg, R. A. and Landy, A. in *Lambda II,* p. 211 (1983), Cold Spring Harbor Laboratory)), to produce the integrated lambda genome flanked by attL (about 100 bp) and attR (about 160 bp) sites. In the absence of Xis (see below), this reaction is essentially irreversible. The integration reaction mediated by integrase and IHF works in vitro, with simple buffer containing spermidine. Integrase can be obtained as described by Nash, H. A., *Methods of Enzymology* 100:210–216 (1983). IHF can be obtained as described by Filutowicz, M., et al., *Gene* 147:149–150 (1994).

In the presence of the λ protein Xis (excise) integrase catalyzes the reaction of attR and attL to form attP and attB, i.e., it promotes the reverse of the reaction described above. This reaction can also be applied in the present invention.

Other Recombination Systems. Numerous recombination systems from various organisms can also be used, based on the teaching and guidance provided herein. See, e.g., Hoess et al., *Nucleic Acids Research* 14(6):2287 (1986); Abremski et al., *J. Biol. Chem.*261(1):391 (1986); Campbell, *J. Bacteriol.* 174(23):7495 (1992); Qian et al., *J. Biol. Chem.* 267(11):7794 (1992); Araki et al., *J. Mol. Biol.* 225(1):25 (1992)). Many of these belong to the integrase family of recombinases (Argos et al. *EMBO J.* 5:433–440 (1986)). Perhaps the best studied of these are the Integrase/att system from bacteriophage λ (Landy, A. (1993) *Current Opinions in Genetics and Devel.* 3:699–707), the Cre/loxP system from bacteriophage P1 (Hoess and Abremski (1990) In *Nucleic Acids and Molecular Biology*, vol. 4. Eds.: Eckstein and Lilley, Berlin-Heidelberg: Springer-Verlag; pp. 90–109), and the FLP/FRT system from the Saccharomyces cerevisiae 2μ circle plasmid (Broach et al. *Cell* 29:227–234 (1982)).

Members of a second family of site-specific recombinases, the resolvase family (e.g., γδ, Tn3 resolvase, Hin, Gin, and Cin) are also known. Members of this highly related family of recombinases are typically constrained to intramolecular reactions (e.g., inversions and excisions) and can require host-encoded encoded factors. Mutants have been isolated that relieve some of the requirements for host factors (Maeser and Kahnmann (1991) *Mol. Gen. Genet.* 230:170–176), as well as some of the constraints of intramolecular recombination.

Other site-specific recombinases similar to λ Int and similar to P1 Cre can be substituted for Int and Cre. Such recombinases are known. In many cases the purification of such other recombinases has been described in the art. In cases when they are not known, cell extracts can be used or the enzymes can be partially purified using procedures described for Cre and Int.

While Cre and Int are described in detail for reasons of example, many related recombinase systems exist and their application to the described invention is also provided according to the present invention. The integrase family of site-specific recombinases can be used to provide alternative recombination proteins and recombination sites for the present invention, as site-specific recombination proteins encoded by bacteriophage lambda, phi 80, P22, P2, 186, P4 and P1. This group of proteins exhibits an unexpectedly large diversity of sequences. Despite this diversity, all of the recombinases can be aligned in their C-terminal halves.

A 40-residue region near the C terminus is particularly well conserved in all the proteins and is homologous to a region near the C terminus of the yeast 2 mu plasmid Flp protein. Three positions are perfectly conserved within this family: histidine, arginine and tyrosine are found at respective alignment positions 396, 399 and 433 within the well-conserved C-terminal region. These residues contribute to the active site of this family of recombinases, and suggest that tyrosine-433 forms a transient covalent linkage to DNA during strand cleavage and rejoining. See, e.g., Argos, P. et al., *EMBO J.* 5:433–40 (1986).

Alternatively, IS231 and other Bacillus thuringiensis transposable elements could be used as recombination proteins and recombination sites. Bacillus thuringiensis is an entomopathogenic bacterium whose toxicity is due to the presence in the sporangia of delta-endotoxin crystals active against agricultural pests and vectors of human and animal diseases. Most of the genes coding for these toxin proteins are plasmid-borne and are generally structurally associated with insertion sequences (IS231, IS232, IS240, ISBT1 and ISBT2) and transposons (Tn4430 and Tn5401). Several of these mobile elements have been shown to be active and participate in the crystal gene mobility, thereby contributing to the variation of bacterial toxicity.

Structural analysis of the iso-IS231 elements indicates that they are related to IS1151 from *Clostridium perfringens* and distantly related to IS4 and IS186 from *Escherichia coli*. Like the other IS4 family members, they contain a conserved transposase-integrase motif found in other IS families and retroviruses.

Moreover, functional data gathered from IS231A in *Escherichia coli* indicate a non-replicative mode of transposition, with a preference for specific targets. Similar results were also obtained in *Bacillus subtilis* and *B. thuringiensis*. See, e.g., Mahillon, J. et al., *Genetica* 93:13–26 (1994); Campbell, *J. Bacteriol.* 7495–7499 (1992).

The amount of recombinase which is added to drive the recombination reaction can be determined by using known assays. Specifically, titration assay is used to determine the appropriate amount of a purified recombinase enzyme, or the appropriate amount of an extract.

Engineered Recombination Sites. The above recombinases and corresponding recombinase sites are suitable for use in recombination cloning according to the present invention. However, wild-type recombination sites contain sequences that reduce the efficiency or specificity of recombination reactions as applied in methods of the present invention. For example, multiple stop codons in attB, attR, attP, attL and loxP recombination sites occur in multiple reading frames on both strands, so recombination efficiencies are reducted, e.g., where the coding sequence must cross the recombination sites, (only one reading frame is available on each strand of loxP and attB sites) or impossible (in attP, attR or attL).

Accordingly, the present invention also provides engineered recombination sites that overcome these problems. For example, att sites can be engineered to have one or multiple mutations to enhance specificity or efficiency of the recombination reaction and the properties of Product DNAs (e.g. att1, att2, and att3 sites); to decrease reverse reaction (e.g., removing P1 and H1 from attB). The testing of these mutants determines which mutants yield sufficient recombinational activity to be suitable for recombination subcloning according to the present invention.

Mutations can therefore be introduced into recombination sites for enhancing site specific recombination. Such mutations include, but are not limited to: recombination sites without translation stop codons that allow fusion proteins to be encoded; recombination sites recognized by the same proteins but differing in base sequence such that they react largely or exclusively with their homologous partners allow multiple reactions to be contemplated. Which particular reactions take place can be specified by which particular partners are present in the reaction mixture. For example, a tripartite protein fusion could be accomplished with parental plasmids containing recombination sites attR1 and attR2; attL1 and attL3; and/or attR3 and attL2.

There are well known procedures for introducing specific mutations into nucleic acid sequences. A number of these are described in Ausubel, F. M. et al., *Current Protocols in Molecular Biology*, Wiley Interscience, New York (1989–1996). Mutations can be designed into oligonucleotides, which can be used to modify existing cloned sequences, or in amplification reactions. Random mutagenesis can also be employed if appropriate selection methods are available to isolate the desired mutant DNA or RNA. The presence of the desired mutations can be confirmed by sequencing the nucleic acid by well known methods.

The following non-limiting methods can be used to engineer a core region of a given recombination site to provide mutated sites suitable for use in the present invention:

1. By recombination of two parental DNA sequences by site-specific (e.g. attL and attR to give attB) or other (e.g. homologous) recombination mechanisms. The DNA parental DNA segments containing one or more base alterations resulting in the final core sequence;
2. By mutation or mutagenesis (site-specific, PCR, random, spontaneous, etc) directly of the desired core sequence;
3. By mutagenesis (site-specific, PCR, random, spontanteous, etc) of parental DNA sequences, which are recombined to generate a desired core sequence; and
4. By reverse transcription of an RNA encoding the desired core sequence.

The functionality of the mutant recombination sites can be demonstrated in ways that depend on the particular characteristic that is desired. For example, the lack of translation stop codons in a recombination site can be demonstrated by expressing the appropriate fusion proteins. Specificity of recombination between homologous partners can be demonstrated by introducing the appropriate molecules into in vitro reactions, and assaying for recombination products as described herein or known in the art. Other desired mutations in recombination sites might include the presence or absence of restriction sites, translation or transcription start signals, protein binding sites, and other known functionalities of nucleic acid base sequences. Genetic selection schemes for particular functional attributes in the recombination sites can be used according to known method steps. For example, the modification of sites to provide (from a pair of sites that do not interact) partners that do interact could be achieved by requiring deletion, via recombination between the sites, of a DNA sequence encoding a toxic substance. Similarly, selection for sites that remove translation stop sequences, the presence or absence of protein binding sites, etc., can be easily devised by those skilled in the art.

Accordingly, the present invention provides a nucleic acid molecule, comprising at least one DNA segment having at least two engineered recombination sites flanking a Selectable marker and/or a desired DNA segment, wherein at least one of said recombination sites comprises a core region having at least one engineered mutation that enhances recombination in vitro in the formation of a Cointegrate DNA or a Product DNA.

The nucleic acid molecule can have at least one mutation that confers at least one enhancement of said recombination, said enhancement selected from the group consisting of substantially (i) favoring excisive integration; (ii) favoring excisive recombination; (ii) relieving the requirement for host factors; (iii) increasing the efficiency of said Cointegrate DNA or Product DNA formation; and (iv) increasing the specificity of said Cointegrate DNA or Product DNA formation.

The nucleic acid molecule preferably comprises at least one recombination site derived from attB, attP, attL or attR. More preferably the att site is selected from att1, att2, or att3, as described herein.

In a preferred embodiment, the core region comprises a DNA sequence selected from the group consisting of:
(a) RKYCWGCTTTYKTRTACNAASTSGB(m-att) (SEQ ID NO:1);
(b) AGCCWGCTTTYKTRTACNAACTSGB (m-attB) (SEQ ID NO:2);
(c) GTTCAGCTTTCKTRTACNAACTSGB (m-attR) (SEQ ID NO:3);
(d) AGCCWGCTTTCKTRTACNAAGTSGB (m-attL) (SEQ ID NO:4);
(e) GTTCAGCTTTYKTRTACNAAGTSGB(m-attP1) (SEQ ID NO:5);

or a corresponding or complementary DNA or RNA sequence, wherein R=A or G; K=G or T/U; Y=C or T/U; W=A or T/U; N=A or C or G or T/U; S=C or G; and B=C or G or T/U, as presented in 37 C.F.R. §1.822, which is entirely incorporated herein by reference, wherein the core region does not contain a stop codon in one or more reading frames.

The core region also preferably comprises a DNA sequence selected from the group consisting of:
(a) AGCCTGCTTTTTTGTACAAACTTGT(attB1)(SEQ ID NO:6);
(b) AGCCTGCTTTCTTGTACAAACTTGT(attB2)(SEQ ID NO:7);
(c) ACCCAGCTTTCTTGTACAAACTTGT(attB3)(SEQ ID NO:8);
(d) GTTCAGCTTTTTTGTACAAACTTGT(attR1)(SEQ ID NO:9);
(e) GTTCAGCTTTCTTGTACAAACTTGT(attR2) (SEQID NO:10);
(f) GTTCAGCTTTCTTGTACAAAGTTGG (attR3) (SEQ ID NO:11);
(g) AGCCTGCTTTTTTGTACAAAGTTGG (attL1) (SEQ ID NO:12);
(h) AGCCTGCTTTCTTGTACAAAGTTGG (attL2) (SEQ ID NO:13);
(i) ACCCAGCTTTCTTGTACAAAGTTGG (attL3) (SEQ ID NO:14);
(j) GTTCAGCTTTTTTGTACAAAGTTGG(attP1)(SEQ ID NO:15);
(k) GTTCAGCTTTCTTGTACAAAGTTGG (attP2,P3) (SEQ ID NO:16); or a corresponding or complementary DNA or RNA sequence.

The present invention thus also provides a method for making a nucleic acid molecule, comprising providing a nucleic acid molecule having at least one engineered recombination site comprising at least one DNA sequence having at least 80–99% homology (or any range or value therein) to at least one of SEQ ID NOS:1–16, or any suitable recombination site, or which hybridizes under stringent conditions thereto, as known in the art.

Clearly, there are various types and permutations of such well-known in vitro and in vivo selection methods, each of which are not described herein for the sake of brevity. However, such variations and permutations are contemplated and considered to be the different embodiments of the present invention.

It is important to note that as a result of the preferred embodiment being in vitro recombination reactions, non-biological molecules such as PCR products can be manipulated via the present recombinational cloning method. In one example, it is possible to clone linear molecules into circular vectors.

There are a number of applications for the present invention. These uses include, but are not limited to, changing vectors, apposing promoters with genes, constructing genes for fusion proteins, changing copy number, changing replicons, cloning into phages, and cloning, e.g., PCR products (with an attB site at one end and a loxP site at the other end), genomic DNAs, and cDNAs.

The following examples are intended to further illustrate certain preferred embodiments of the invention and are not intended to be limiting in nature.

EXAMPLES

The present recombinational cloning method accomplishes the exchange of nucleic acid segments to render something useful to the user, such as a change of cloning vectors. These segments must be flanked on both sides by recombination signals that are in the proper orientation with respect to one another. In the examples below the two parental nucleic acid molecules (e.g., plasmids) are called the Insert Donor and the Vector Donor. The Insert Donor contains a segment that will become joined to a new vector contributed by the Vector Donor. The recombination intermediate(s) that contain(s) both starting molecules is called the Cointegrate(s). The second recombination event produces two daughter molecules, called the Product (the desired new clone) and the Byproduct.

Buffers

Various known buffers can be used in the reactions of the present invention. For restriction enzymes, it is advisable to use the buffers recommended by the manufacturer. Alternative buffers can be readily found in the literature or can be devised by those of ordinary skill in the art.

Examples 1–3.

One exemplary buffer for lambda integrase is comprised of 50 mM Tris-HCl, at pH 7.5–7.8, 70 mM KCl, 5 mM spermidine, 0.5 mM EDTA, and 0.25 mg/ml bovine serum albumin, and optionally, 10% glycerol.

One preferred buffer for P1 Cre recombinase is comprised of 50 mM Tris-HCl at pH 7.5, 33 mM NaCl, 5 mM spermidine, and 0.5 mg/ml bovine serum albumin.

The buffer for other site-specific recombinases which are similar to lambda Int and P1 Cre are either known in the art or can be determined empirically by the skilled artisans, particularly in light of the above-described buffers.

Example 1
Recombinational Cloning Using Cre and Cre & Int

Two pairs of plasmids were constructed to do the in vitro recombinational cloning method in two different ways. One pair, pEZC705 and pEZC726 (FIG. 2A), was constructed with loxP and att sites, to be used with Cre and λ integrase. The other pair, pEZC602 and pEZC629 (FIG. 3A), contained the loxP (wild type) site for Cre, and a second mutant lox site, loxP 511, which differs from loxP in one base (out of 34 total). The minimum requirement for recombinational cloning of the present invention is two recombination sites in each plasmid, in general X and Y, and X' and Y'. Recombinational cloning takes place if either or both types of site can recombine to form a Cointegrate (e.g. X and X'), and if either or both (but necessarily a site different from the type forming the Cointegrate) can recombine to excise the Product and Byproduct plasmids from the Cointegrate (e.g. Y and Y'). It is important that the recombination sites on the same plasmid do not recombine. It was found that the present recombinational cloning could be done with Cre alone.

Cre-Only

Two plasmids were constructed to demonstrate this conception (see FIG. 3A). pEZC629 was the Vector Donor plasmid. It contained a constitutive drug marker (chloramphenicol resistance), an origin of replication, loxP and loxP 511 sites, a conditional drug marker (kanamycin resistance whose expression is controlled by the operator/promoter of the tetracycline resistance operon of transposon Tn10), and a constitutively expressed gene for the tet repressor protein, tetR. E. coli cells containing pEZC629 were resistant to chloramphenicol at 30 μg/ml, but sensitive to kanamycin at 100 μg/ml. pEZC602 was the Insert Donor plasmid, which contained a different drug marker (ampicillin resistance), an origin, and loxP and loxP 511 sites flanking a multiple cloning site.

This experiment was comprised of two parts as follows:

Part I: About 75 ng each of pEZC602 and pEZC629 were mixed in a total volume of 30 μl of Cre buffer (50 mM Tris-HCl pH 7.5, 33 mM NaCl, 5 mM spermidine-HCl, 500 μg/ml bovine serum albumin). Two 10 μl aliquots were transferred to new tubes. One tube received 0.5 μl of Cre protein (approx. 4 units per μl; partially purified according to Abremski and Hoess, J. Biol. Chem. 259:1509 (1984)). Both tubes were incubated at 37° C. for 30 minutes, then 70° C. for 10 minutes. Aliquots of each reaction were diluted and transformed into DH5α. Following expression, aliquots were plated on 30 μg/ml chloramphenicol; 100 μg/ml ampicillin plus 200 μg/ml methicillin; or 100 μg/ml kanamycin. Results: See Table 1. The reaction without Cre gave $1.11 \times 10^6$ ampicillin resistant colonies (from the Insert Donor plasmid pEZC602); $7.8 \times 10^5$ chloramphenicol resistant colonies (from the Vector Donor plasmid pEZC629); and 140 kanamycin resistant colonies (background). The reaction with added Cre gave $7.5 \times 10^5$ ampicillin resistant colonies (from the Insert Donor plasmid pEZC602); $6.1 \times 10^5$ chloramphenicol resistant colonies (from the Vector Donor plasmid pEZC629); and 760 kanamycin resistant colonies (mixture of background colonies and colonies from the recombinational cloning Product plasmid). Analysis: Because the number of colonies on the kanamycin plates was much higher in the presence of Cre, many or most of them were predicted to contain the desired Product plasmid.

TABLE 1

| Enzyme | Ampicillin | Chloramphenicol | Kanamycin | Efficiency |
|---|---|---|---|---|
| None | $1.1 \times 10^6$ | $7.8 \times 10^5$ | 140 | $140/7.8 \times 10^5 = 0.02\%$ |
| Cre | $7.5 \times 10^5$ | $6.1 \times 10^5$ | 760 | $760/6.1 \times 10^5 = 0.12\%$ |

Part II: Twenty four colonies from the "+Cre" kanamycin plates were picked and inoculated into medium containing 100 μg/ml kanamycin. Minipreps were done, and the miniprep DNAs, uncut or cut with SmaI or HindIII, were electrophoresed. Results: 19 of the 24 minipreps showed supercoiled plasmid of the size predicted for the Product plasmid. All 19 showed the predicted SmaI and HindIII restriction fragments. Analysis: The Cre only scheme was demonstrated. Specifically, it was determined to have yielded about 70% (19 of 24) Product clones. The efficiency was about 0.1% (760 kanamycin resistant clones resulted from $6.1 \times 10^5$ chloramphenicol resistant colonies).

Cre Plus Integrase

Figure 2A:
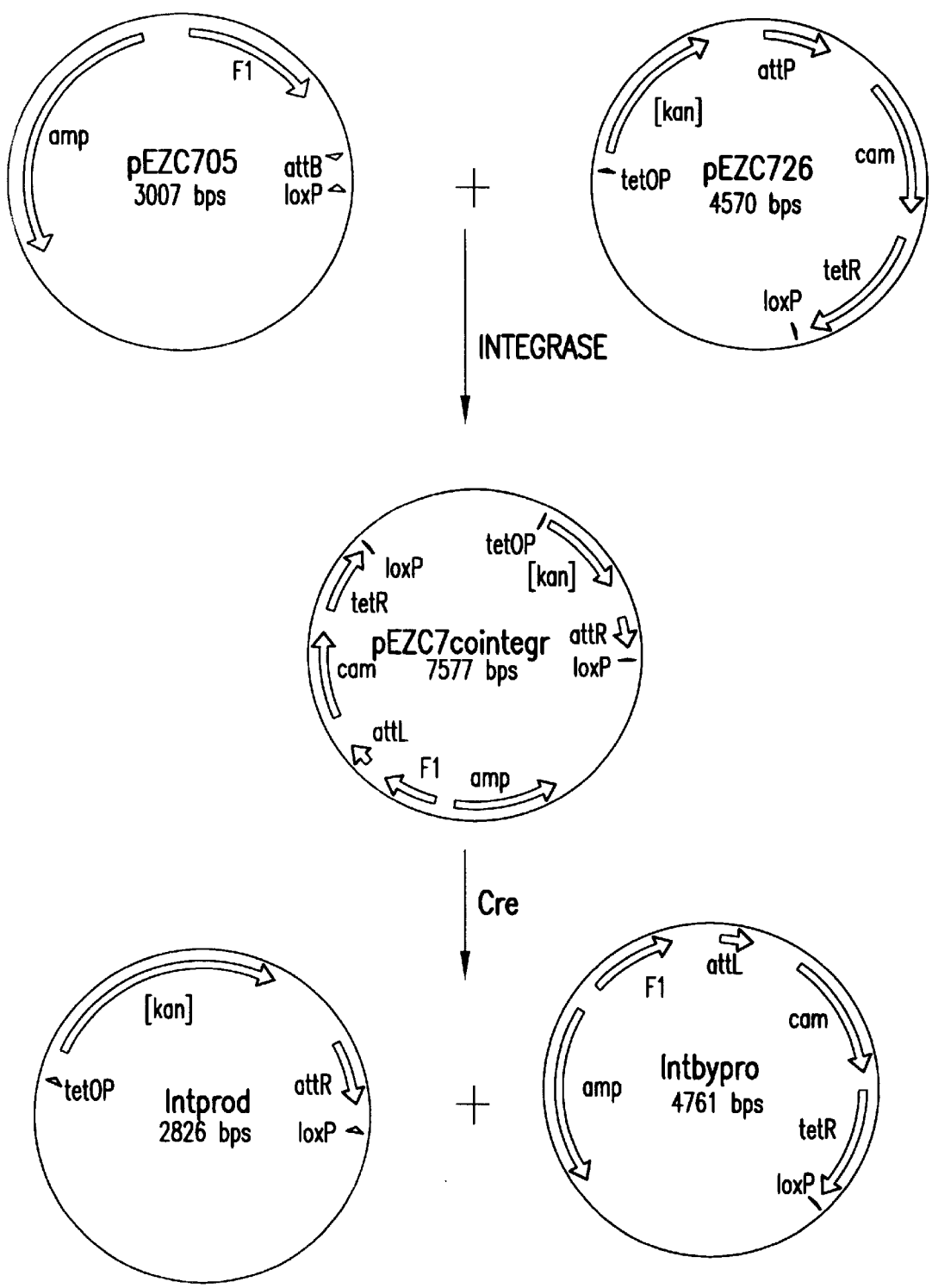
FIG. 2A depicts an in vitro method of recombining an Insert Donor plasmid (here, pEZC705) with a Vector Donor plasmid (here, pEZC726), and obtaining Product DNA and Byproduct daughter molecules. The two recombination sites are attP and loxP on the Vector Donor. On one segment defined by these sites is a kanamycin resistance gene whose promoter has been replaced by the tetOP operator/promoter from transposon Tn10. See Sizemore et al., *Nucl. Acids Res.* 18(10):2875 (1990). In the absence of tet repressor protein, *E. coli* RNA polymerase transcribes the kanamycin resistance gene from the tetOP. If tet repressor is present, it binds to tetOP and blocks transcription of the kanamycin resistance gene. The other segment of pEZC726 has the tet repressor gene expressed by a constitutive promoter. Thus cells transformed by pEZC726 are resistant to chloramphenicol, because of the chloramphenicol acetyl transferase gene on the same segment as tetR, but are sensitive to kanamycin. The recombinase-mediated reactions result in separation of the tetR gene from the regulated kanamycin resistance gene. This separation results in kanamycin resistance in cells receiving only the desired recombination products. The first recombination reaction is driven by the addition of the recombinase called Integrase. The second recombination reaction is driven by adding the recombinase Cre to the Cointegrate (here, pEZC7 Cointegrate).
Figure 2B:
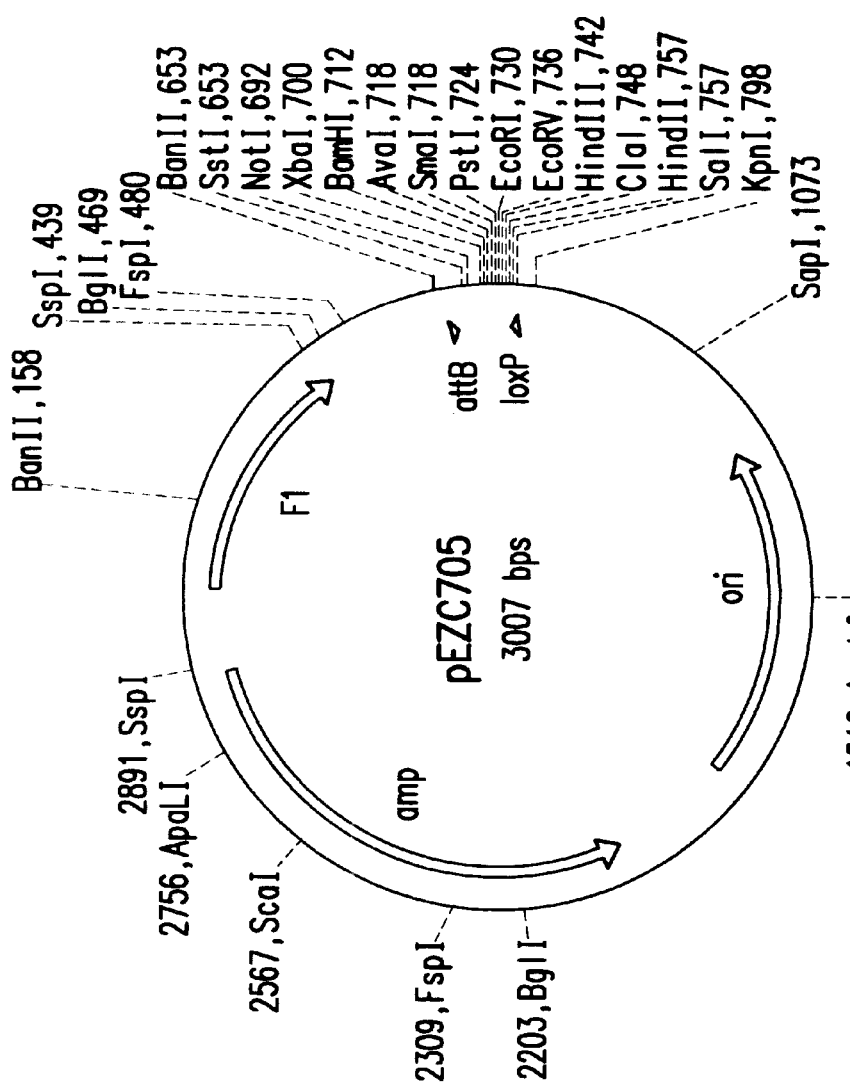
FIG. 2B depicts a restriction map of pEZC705.
Figure 2C:
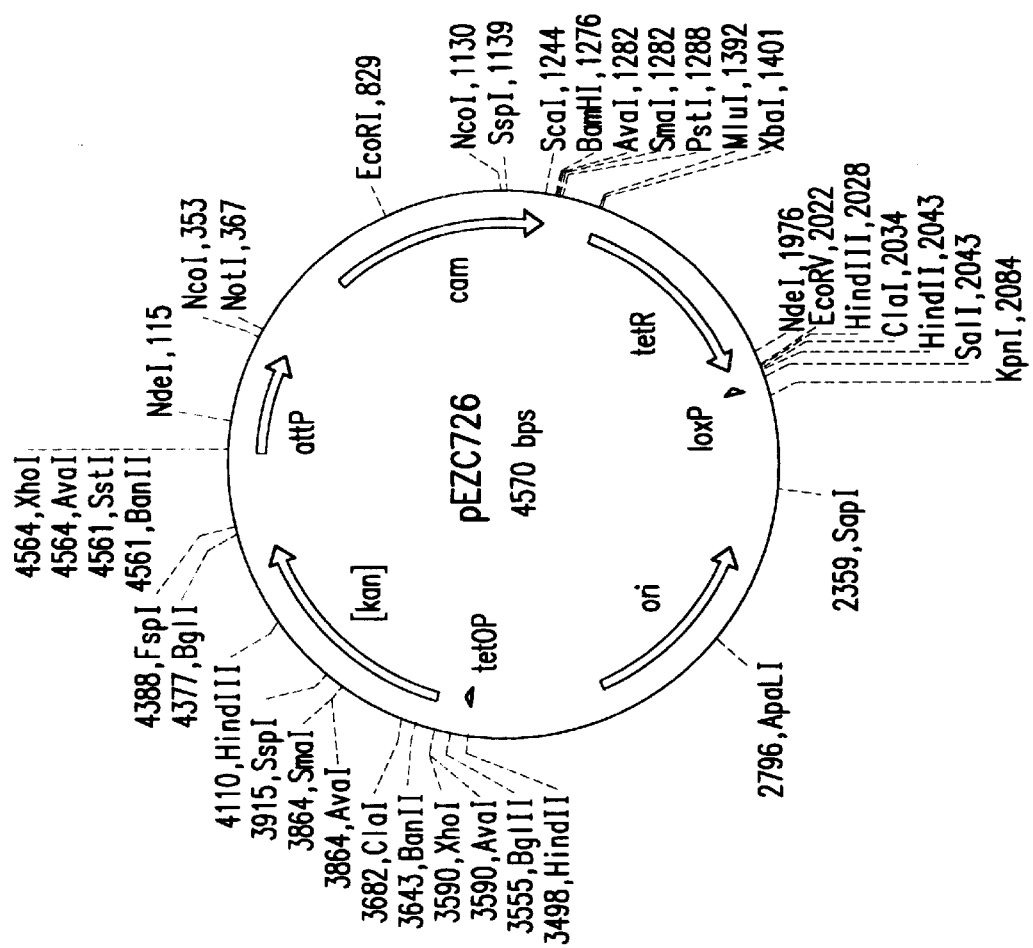
FIG. 2C depicts a restriction map of pEZC726.
Figure 2D:
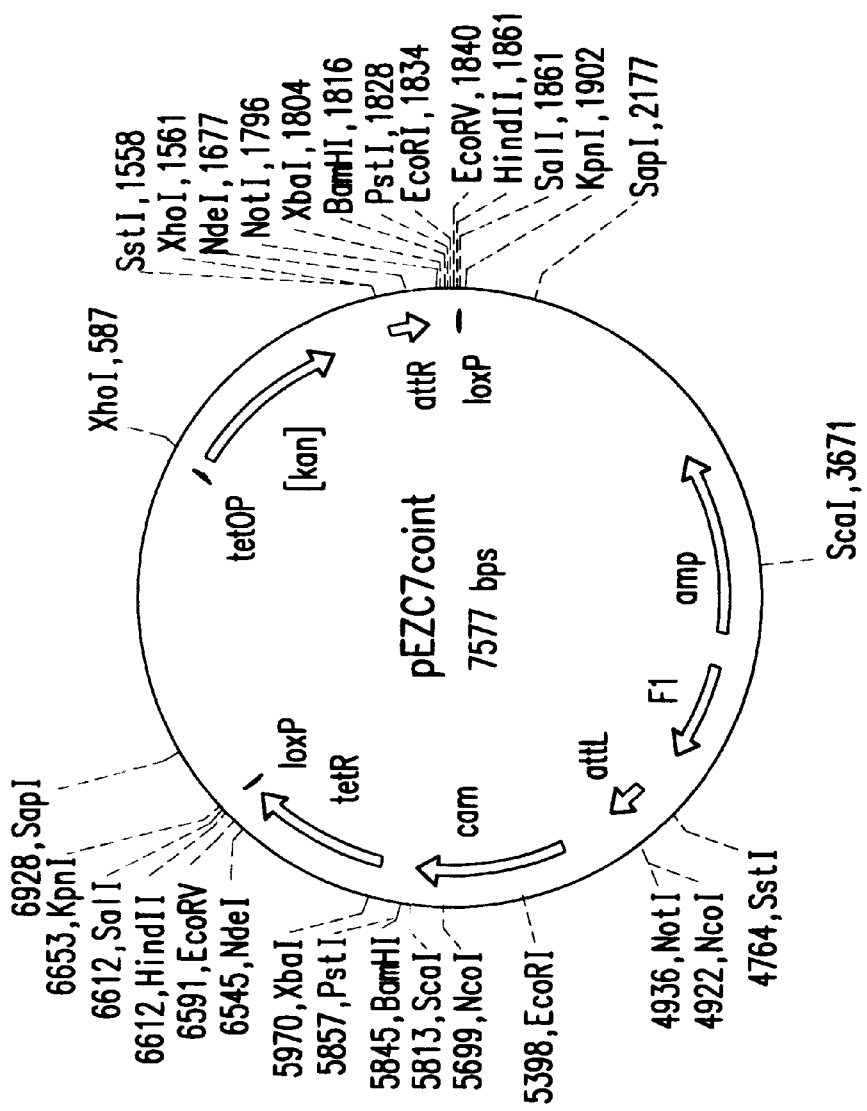
FIG. 2D depicts a restriction map of pEZC7 Cointegrate.
Figure 2E:
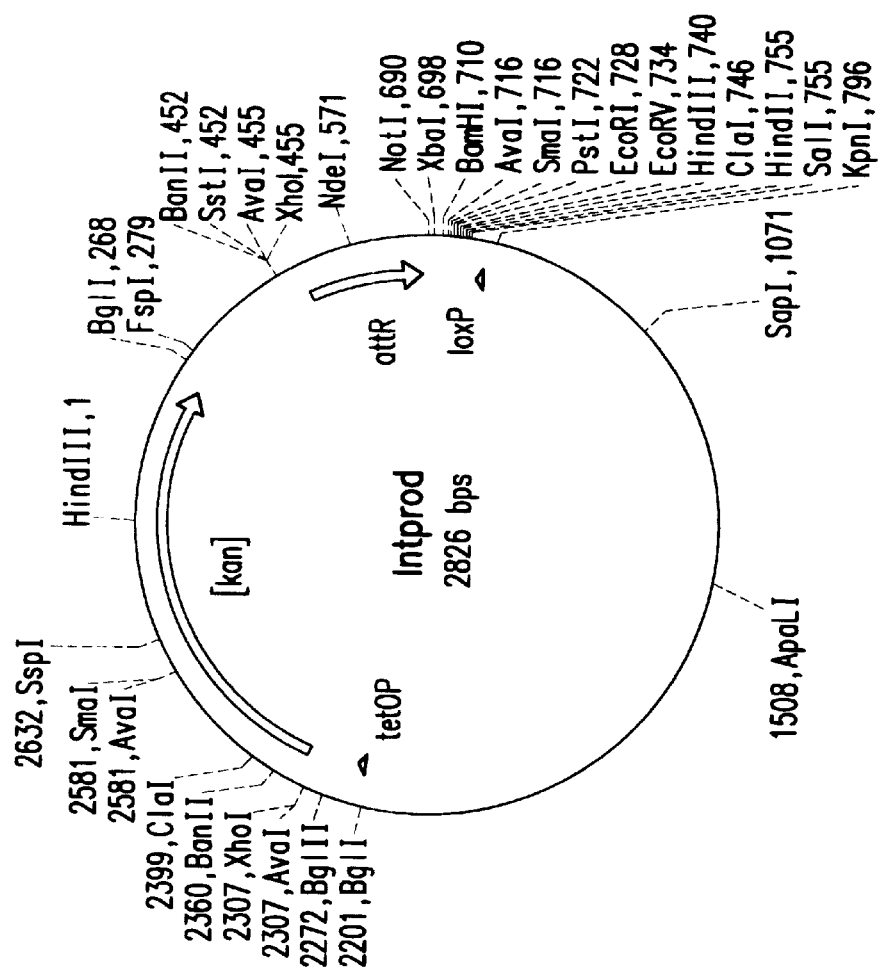
FIG. 2E depicts a restriction map of Intprod.
Figure 2F:
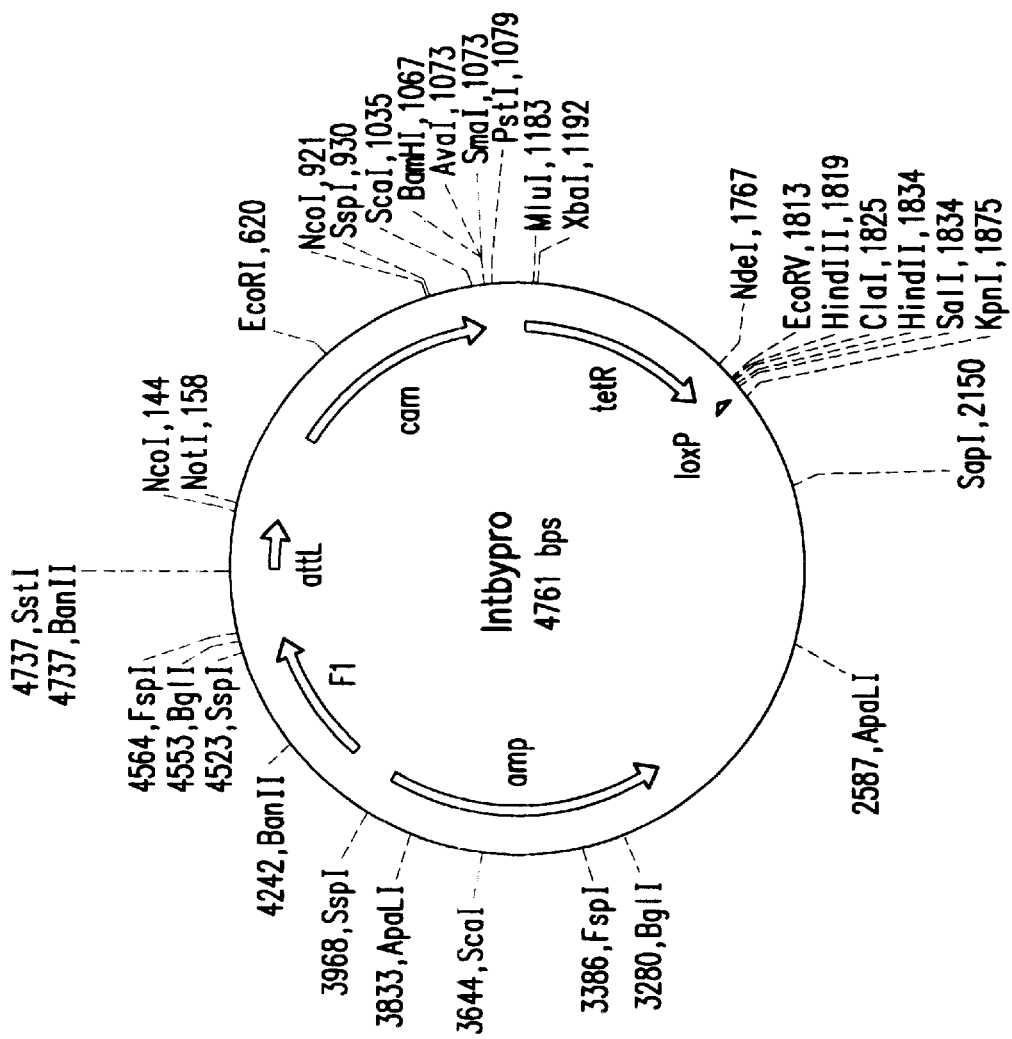
FIG. 2F depicts a restriction map of Intbypro.
Figure 3A:
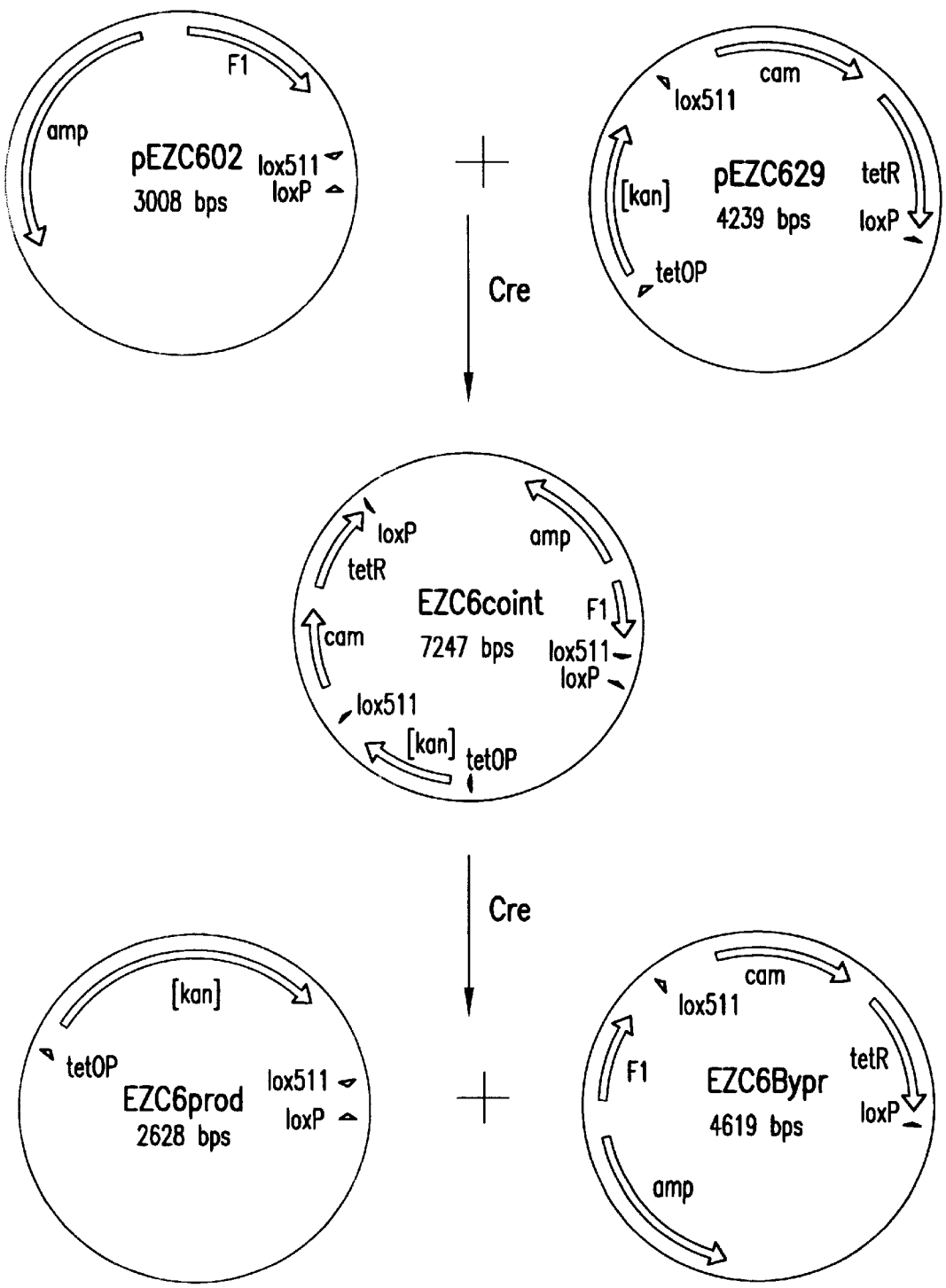
FIG. 3A depicts an in vitro method of recombining an Insert Donor plasmid (here, pEZC602) with a Vector Donor plasmid (here, pEZC629), and obtaining Product (here, EZC6prod) and Byproduct (here, EZC6Bypr) daughter molecules. The two recombination sites are loxP and loxP 511. One segment of pEZC629 defined by these sites is a kanamycin resistance gene whose promoter has been replaced by the tetOP operator/promoter from transposon Tn10. In the absence of tet repressor protein, *E. coli* RNA polymerase transcribes the kanamycin resistance gene from the tetOP. If tet repressor is present, it binds to tetOP and blocks transcription of the kanamycin resistance gene. The other segment of pEZC629 has the tet repressor gene expressed by a constitutive promoter. Thus cells transformed by pEZC629 are resistant to chloramphenicol, because of the chloramphenicol acetyl transferase gene on the same segment as tetR, but are sensitive to kanamycin. The reactions result in separation of the tetR gene from the regulated kanamycin resistance gene. This separation results in kanamycin resistance in cells receiving the desired recombination product. The first and the second recombination events are driven by the addition of the same recombinase, Cre.
Figure 3B:
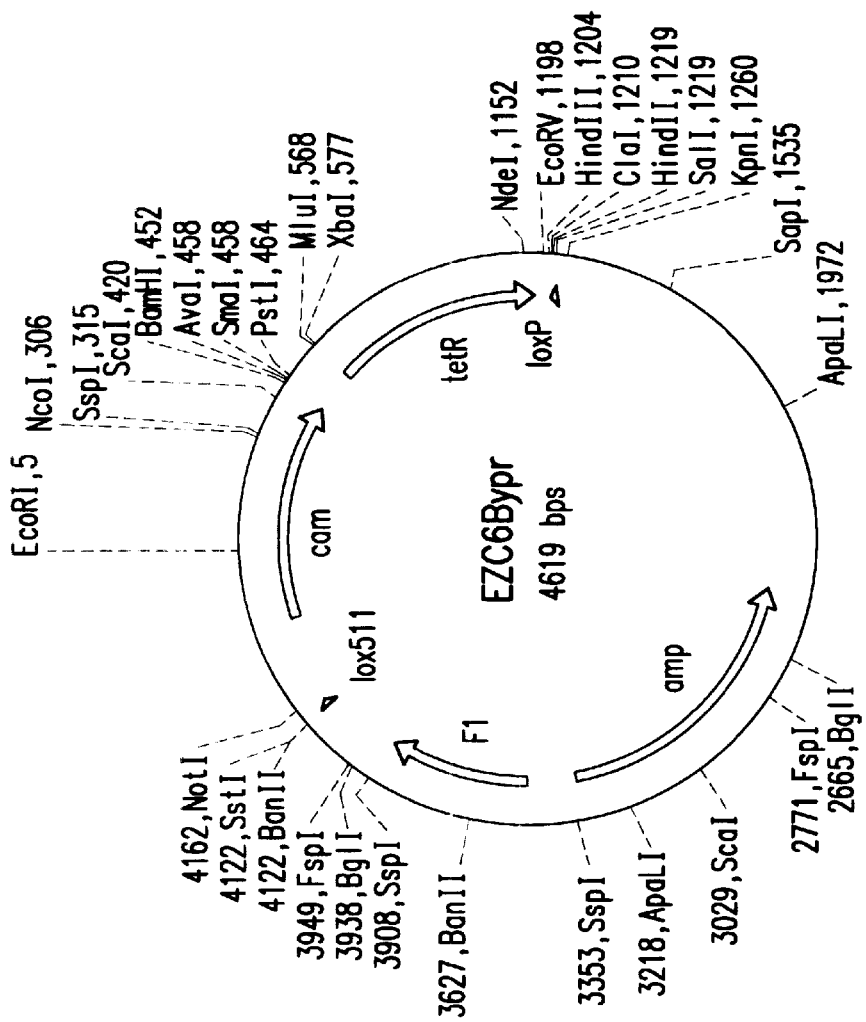
FIG. 3B depicts a restriction map of EZC6Bypr.
Figure 3C:
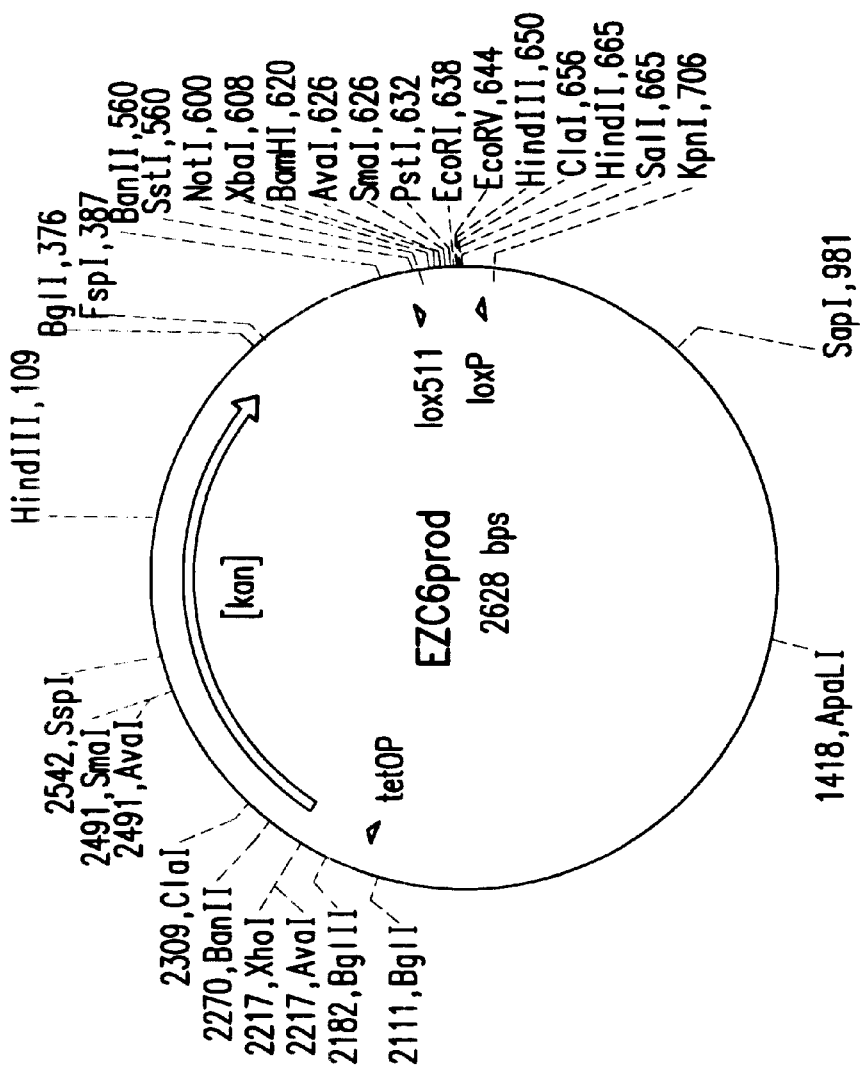
FIG. 3C depicts a restriction map of EZC6prod.
Figure 3D:
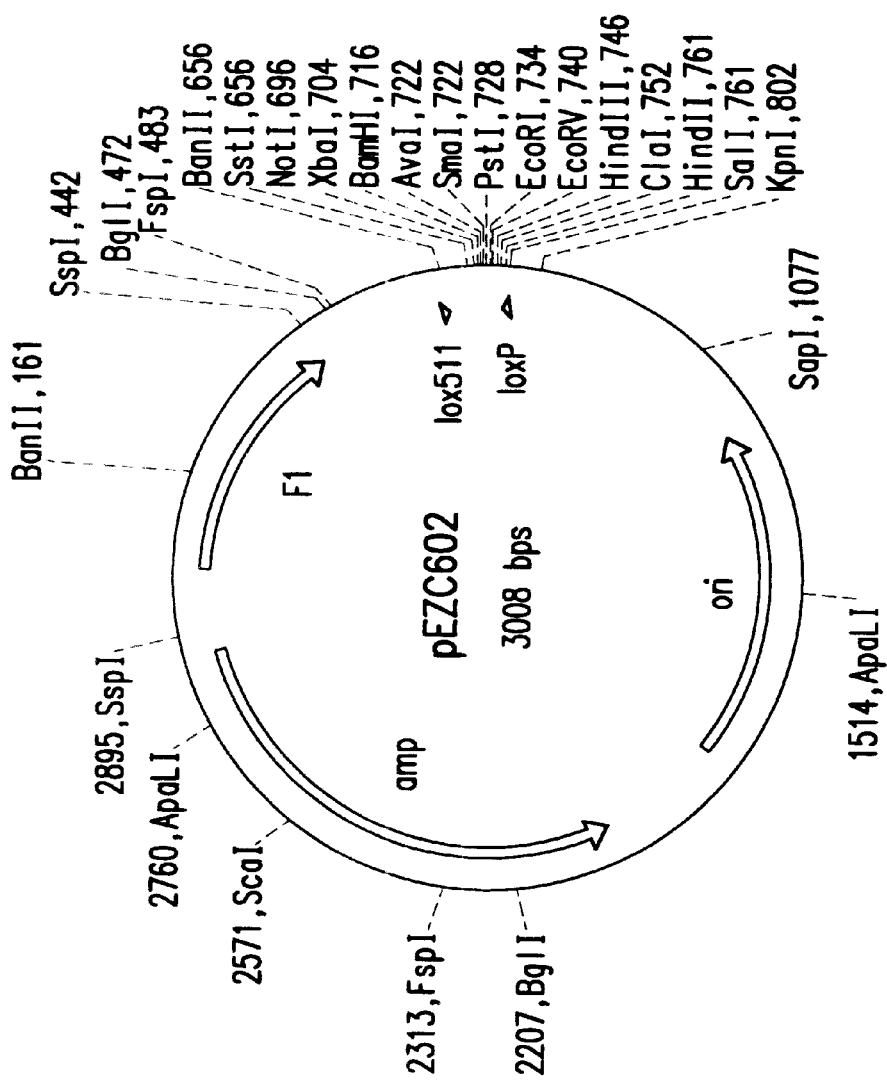
FIG. 3D depicts a restriction map of pEZC602.
Figure 3E:
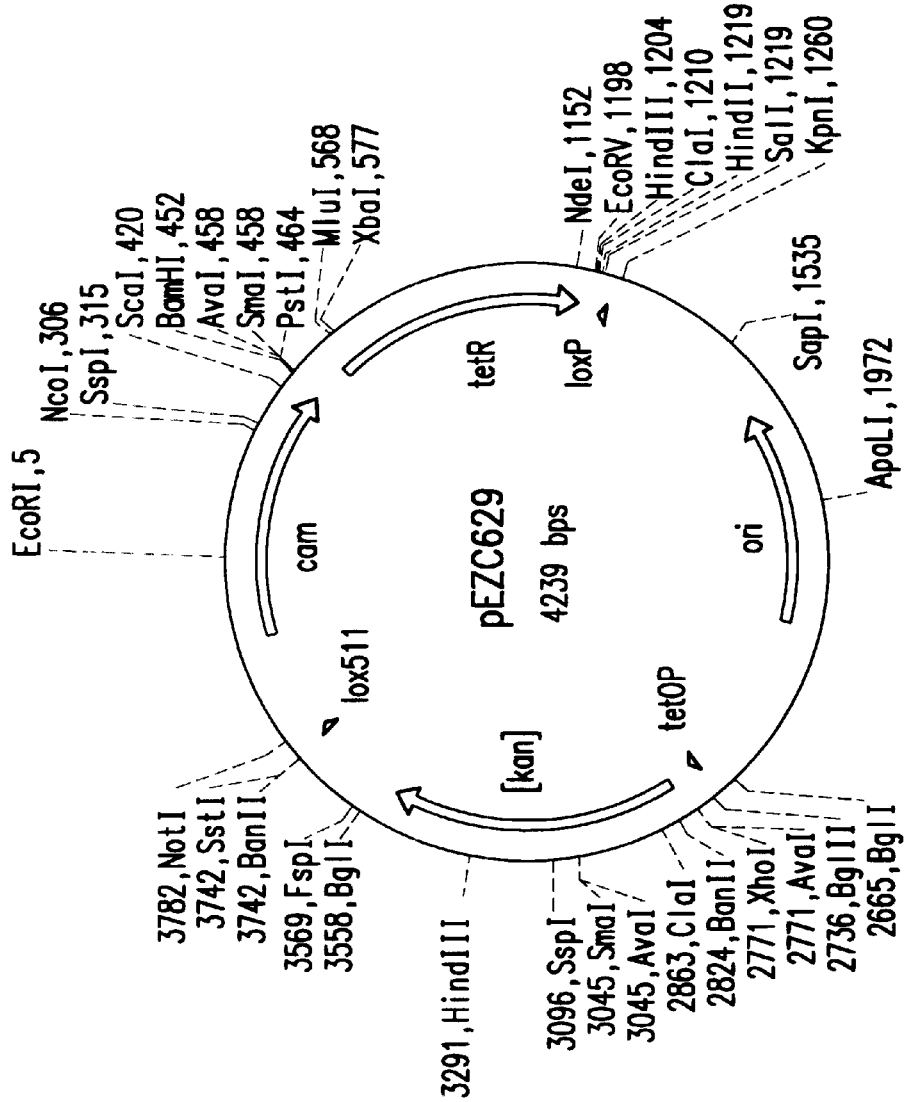
FIG. 3E depicts a restriction map of pEZC629.
Figure 3F:
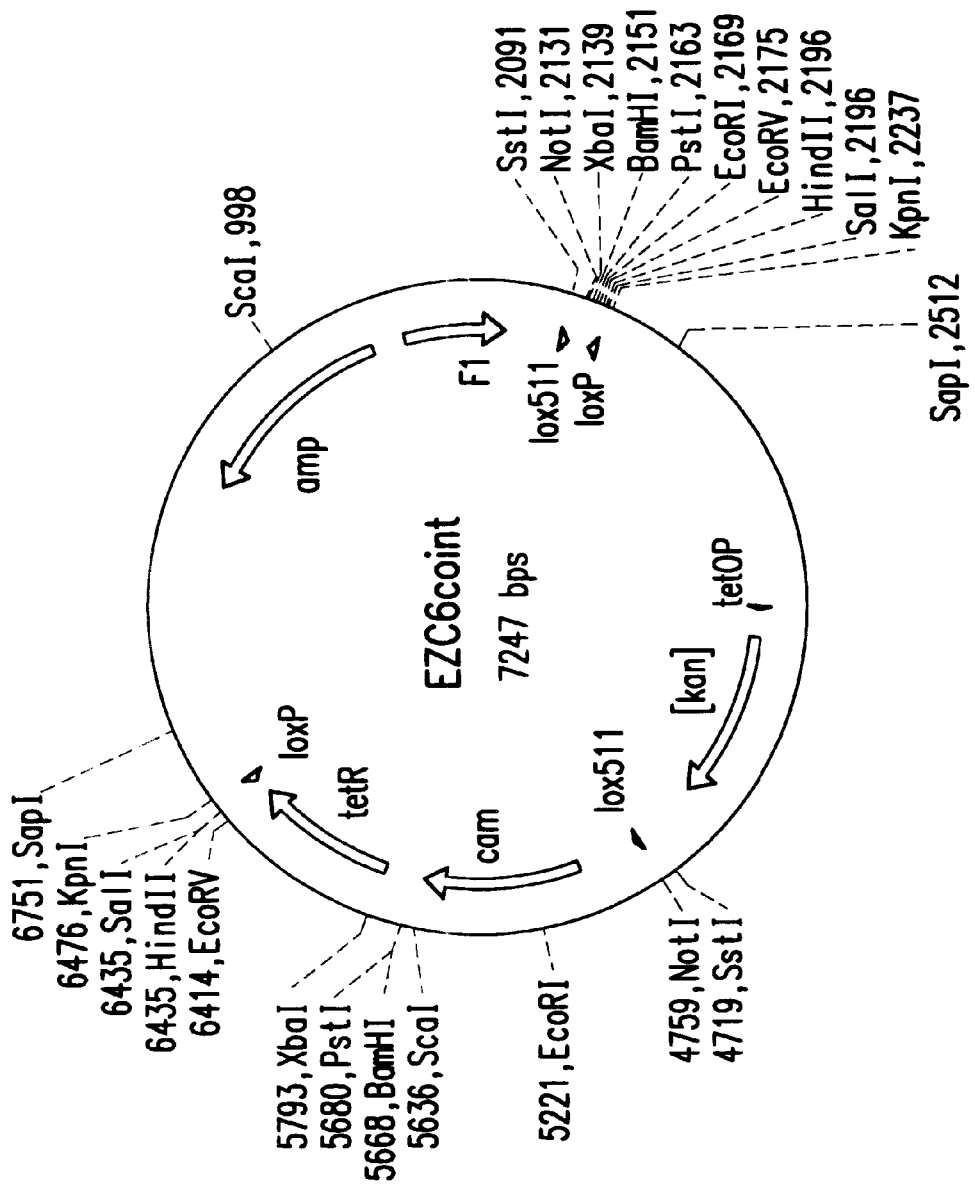
FIG. 3F depicts a restriction map of EZC6coint.

The plasmids used to demonstrate this method are exactly analogous to those used above, except that pEZC726, the Vector Donor plasmid, contained an attP site in place of loxP 511, and pEZC705, the Insert Donor plasmid, contained an attB site in place of loxP 511 (FIG. 2A).

This experiment was comprised of three parts as follows:

Part I: About 500 ng of pEZC705 (the Insert Donor plasmid) was cut with ScaI, which linearized the plasmid within the ampicillin resistance gene. (This was done because the λ integrase reaction has been historically done with the attB plasmid in a linear state (H. Nash, personal communication). However, it was found later that the integrase reaction proceeds well with both plasmids supercoiled.) Then, the linear plasmid was ethanol precipitated and dissolved in 20 μl of λ integrase buffer (50 mM Tris-HCl, about pH 7.8, 70 mM KCl, 5 mM spermidine-HCl, 0.5 mM EDTA, 250 μg/ml bovine serum albumin). Also, about 500 ng of the Vector Donor plasmid pEZC726 was ethanol precipitated and dissolved in 20 μl λ integrase buffer. Just before use, μ integrase (2 μl, 393 μg/ml) was thawed and diluted by adding 18 μl cold μ integrase buffer. One μl IHF (integration host factor, 2.4 mg/ml, an accessory protein) was diluted into 150 μl cold λ integrase buffer. Aliquots (2 μl) of each DNA were mixed with λ integrase buffer, with or without 1 μl each λ integrase and IHF, in a total of 10 μl. The mixture was incubated at 25° C. for 45 minutes, then at 70° C. for 10 minutes. Half of each reaction was applied to an agarose gel. Results: In the presence of integrase and IHF, about 5% of the total DNA was converted to a linear Cointegrate form. Analysis: Activity of integrase and IHF was confirmed.

Part II: Three microliters of each reaction (i.e., with or without integrase and IHF) were diluted into 27 μl of Cre buffer (above), then each reaction was split into two 10 μl aliquots (four altogether). To two of these reactions, 0.5 μl of Cre protein (above) were added, and all reactions were incubated at 37° C. for 30 minutes, then at 70° C. for 10 minutes. TE buffer (90 μl; TE: 10 mM Tris-HCl, pH 7.5, 1 mM EDTA) was added to each reaction, and 1 μl each was transformed into E. coli DH5α. The transformation mixtures were plated on 100 μg/ml ampicillin plus 200 μg/ml methicillin; 30 μg/ml chloramphenicol; or 100 μg/ml kanamycin. Results: See Table 2.

TABLE 2

| Enzyme | Ampicillin | Chloramphenicol | Kanamycin | Efficiency |
|---|---|---|---|---|
| None | 990 | 20000 | 4 | $4/2 \times 10^4 = 0.02\%$ |
| Cre only | 280 | 3640 | 0 | 0 |
| Integrase* only | 1040 | 27000 | 9 | $9/2.7 \times 10^4 = 0.03\%$ |
| Integrase* + Cre | 110 | 1110 | 76 | $76/1.1 \times 10^3 = 6.9\%$ |

*Integrase reactions also contained IHF.

Analysis: The Cre protein impaired transformation. When adjusted for this effect, the number of kanamycin resistant colonies, compared to the control reactions, increased more than 100 fold when both Cre and Integrase were used. This suggests a specificity of greater than 99%.

Part III: 38 colonies were picked from the Integrase plus Cre plates, miniprep DNAs were made and cut with HindIII to give diagnostic mapping information. Result: All 38 had precisely the expected fragment sizes. Analysis: The Cre plus μ integrase method was observed to have much higher specificity than Cre-alone. Conclusion: The Cre plus λ integrase method was demonstrated. Efficiency and specificity were much higher than for Cre only.

Figure 4A:
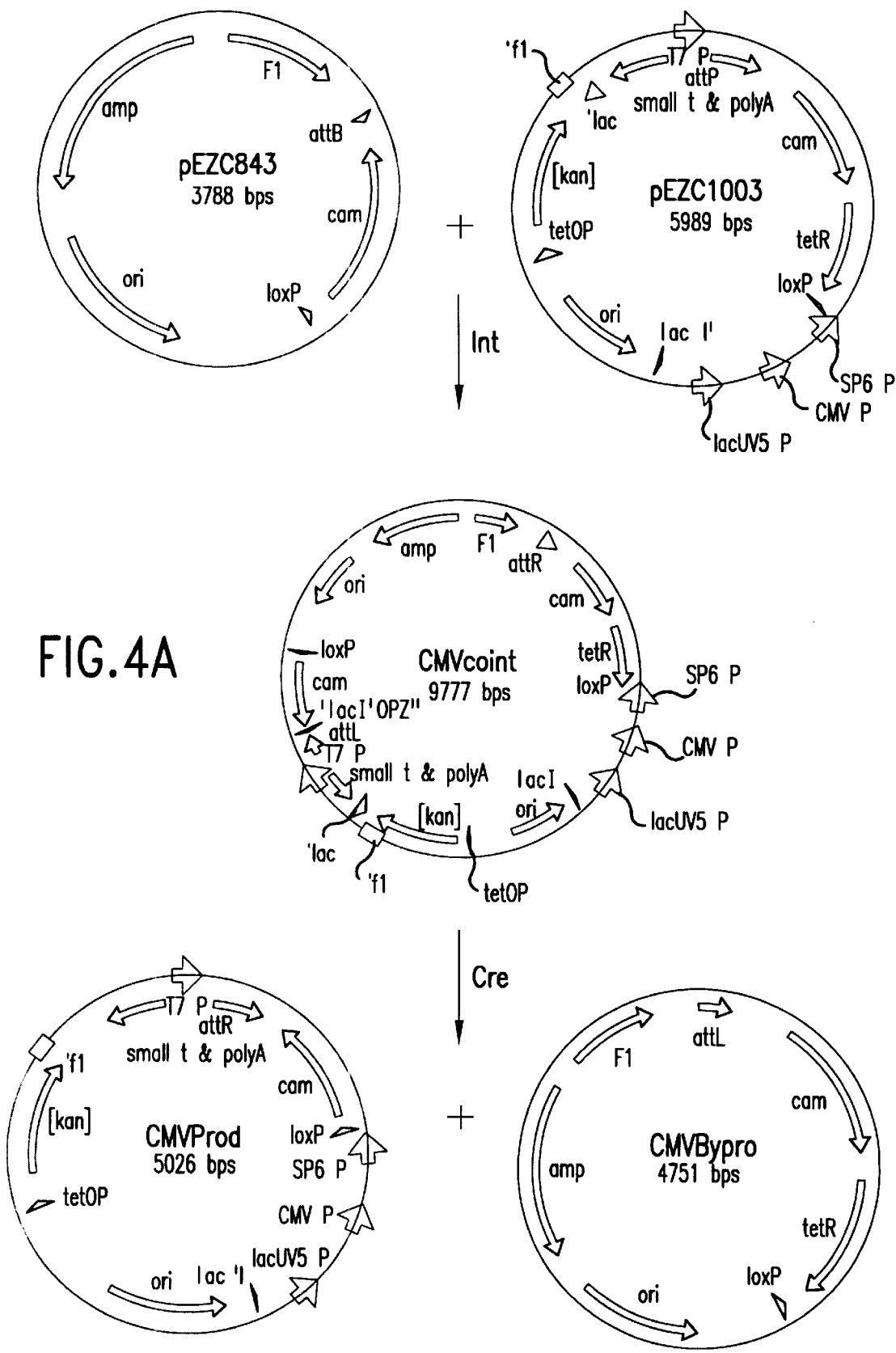
FIG. 4A depicts an application of the in vitro method of recombinational cloning to subclone the chloramphenicol acetyl transferase gene into a vector for expression in eukaryotic cells. The Insert Donor plasmid, pEZC843, is comprised of the chloramphenicol acetyl transferase gene of *E. coli*, cloned between loxP and attB sites such that the loxP site is positioned at the 5'-end of the gene. The Vector Donor plasmid, pEZC1003, contains the cytomegalovirus eukaryotic promoter apposed to a loxP site. The supercoiled plasmids were combined with lambda Integrase and Cre recombinase in vitro. After incubation, competent E. coli cells were transformed with the recombinational reaction solution. Aliquots of transformations were spread on agar plates containing kanamycin to select for the Product molecule (here CMVProd).

Example 2
Using in Vitro Recombinational Cloning to Subclone the Chloramphenicol Acetyl Transferase Gene into a Vector for Expression in Eukaryotic Cells (FIG. 4A)

Figure 4B:
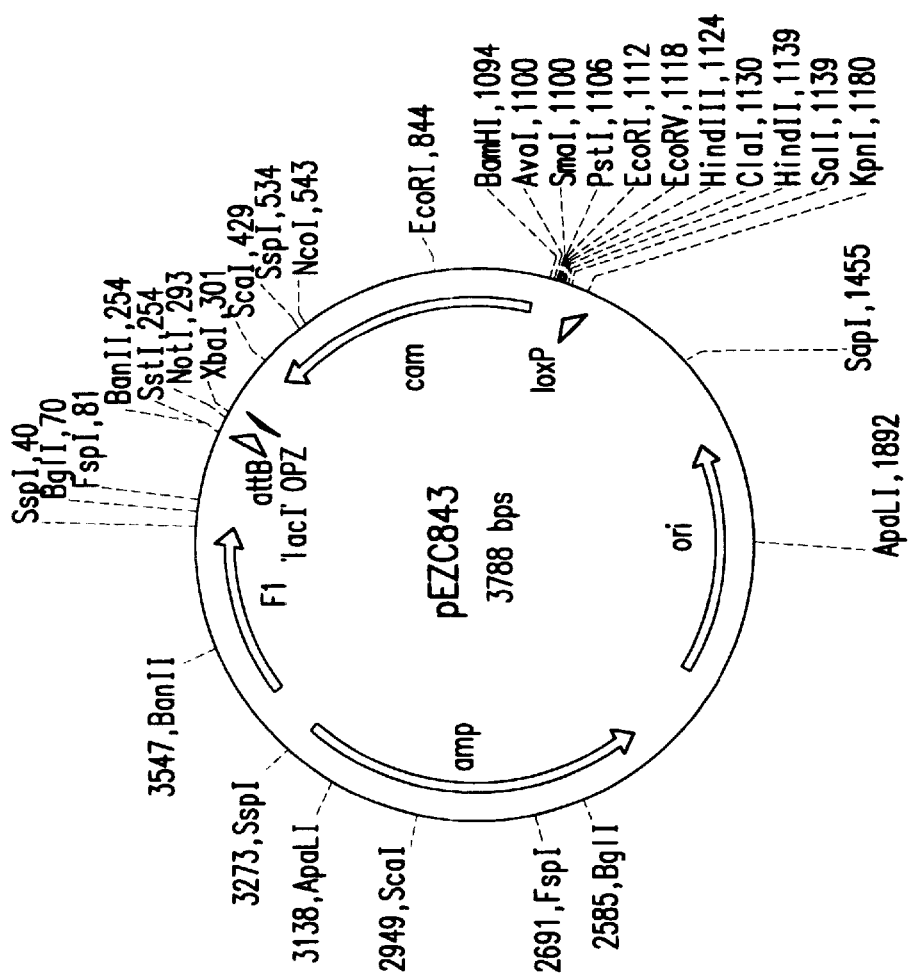
FIG. 4B depicts a restriction map of pEZC843.
Figure 4C:
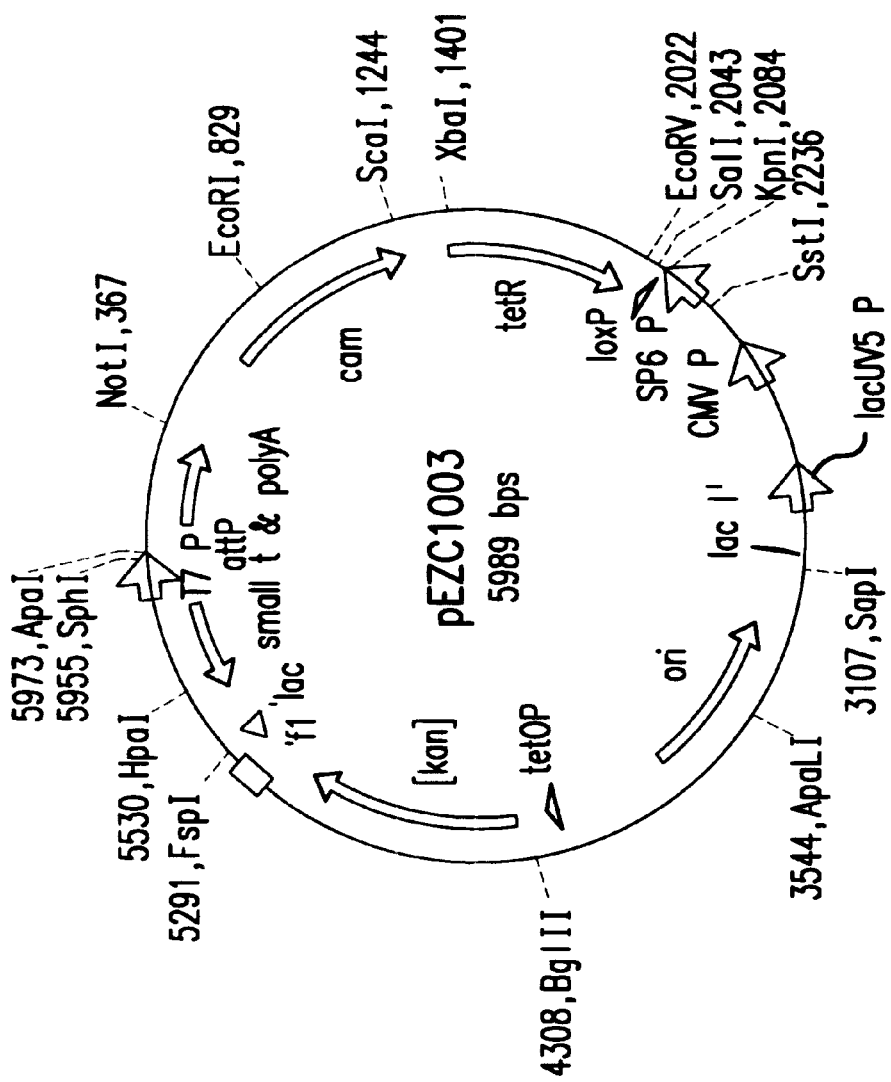
FIG. 4C depicts a restriction map of pEZC1003.
Figure 4D:
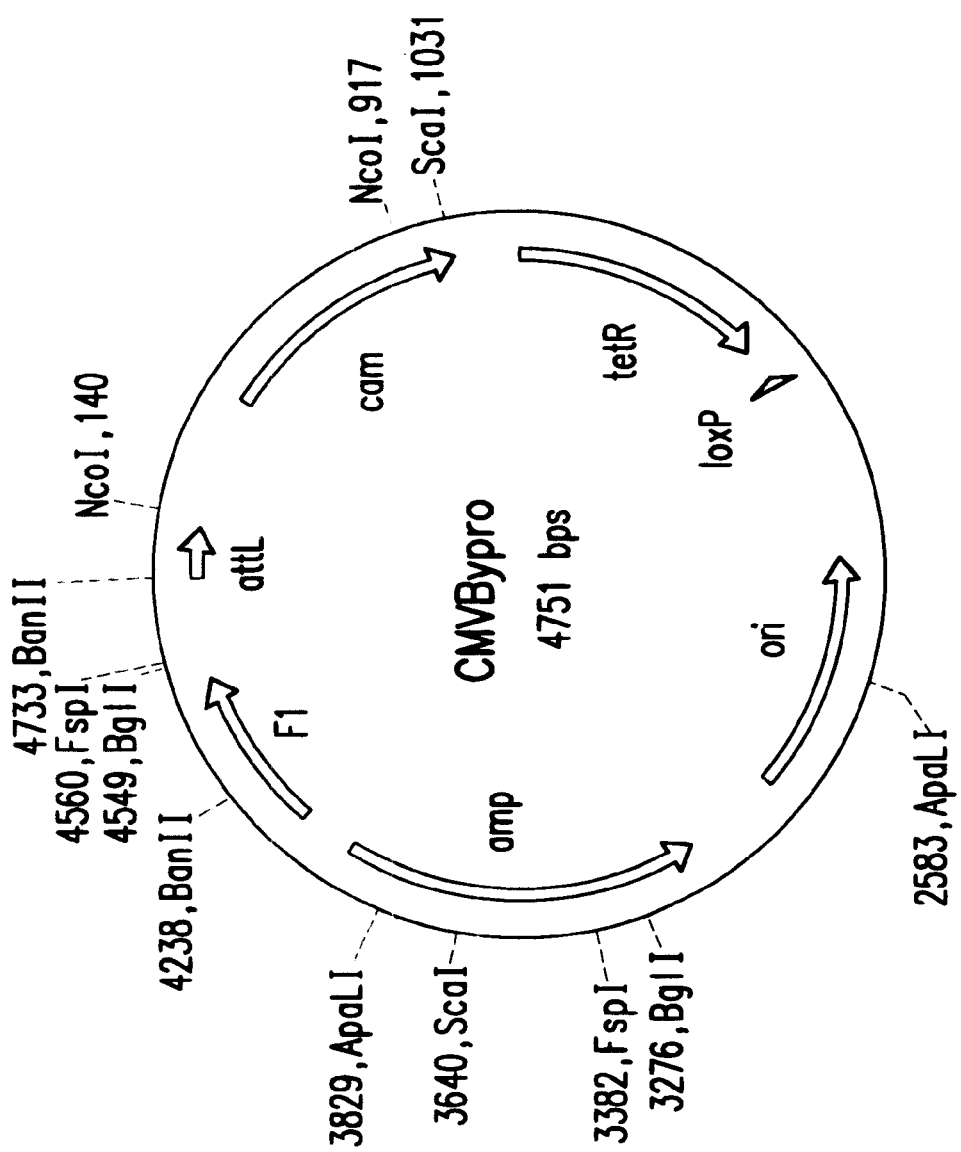
FIG. 4D depicts a restriction map of CMVBypro.
Figure 4E:
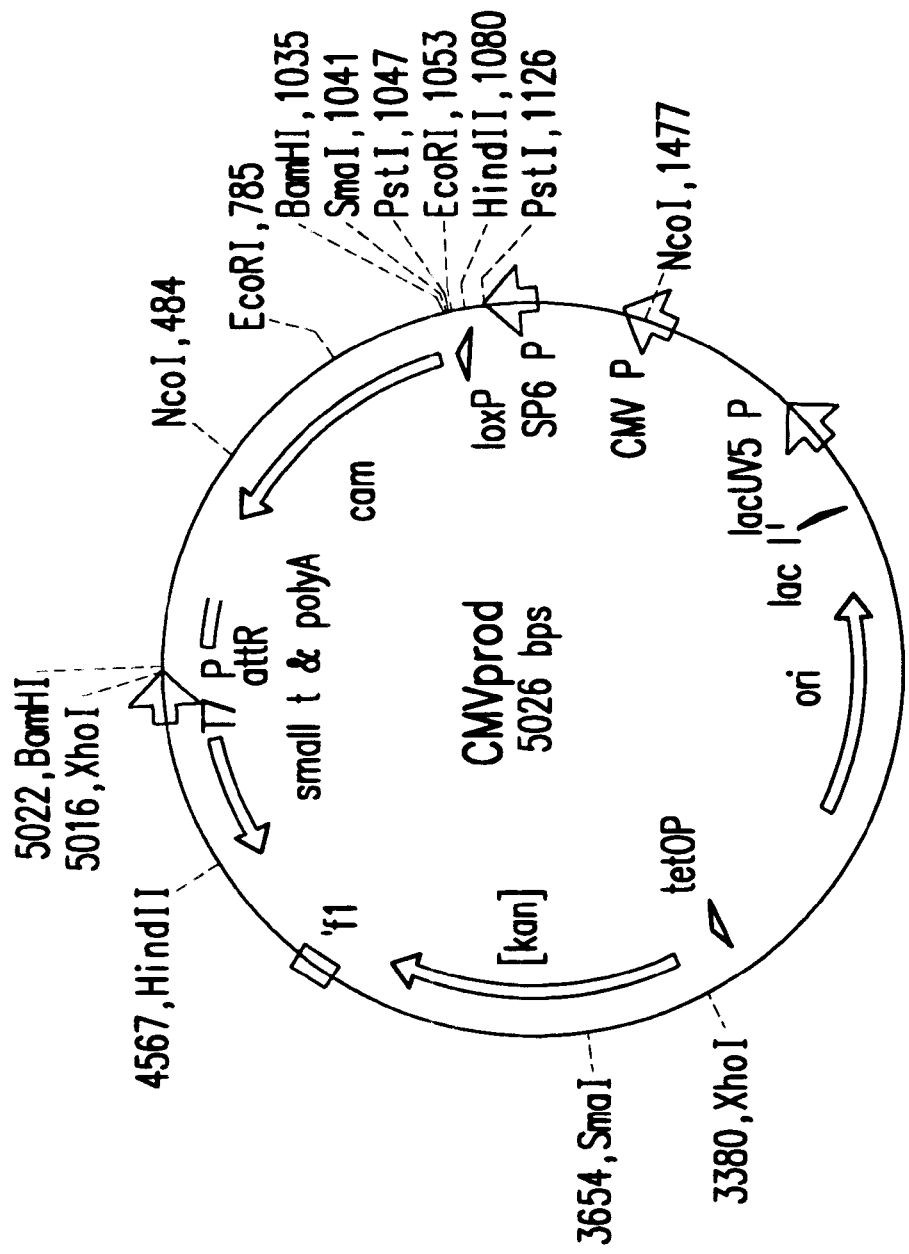
FIG. 4E depicts a restriction map of CMVProd.
Figure 4F:
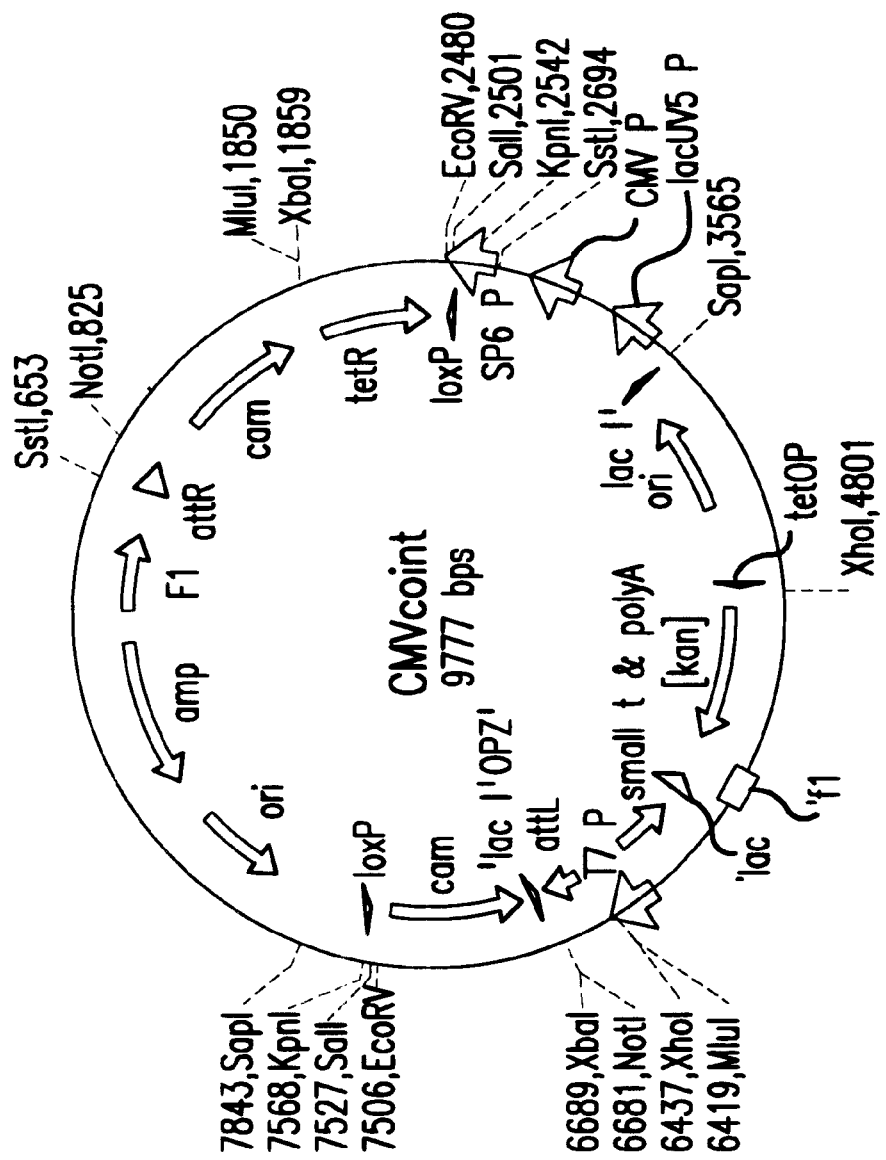
FIG. 4F depicts a restriction map of CMVcoint.

An Insert Donor plasmid, pEZC843, was constructed, comprising the chloramphenicol acetyl tansferase gene of E. coli, cloned between loxP and attB sites such that the loxP site was positioned at the 5'-end of the gene (FIG. 4B). A Vector Donor plasmid, pEZC1003, was constructed, which contained the cytomegalovirus eukaryotic promoter apposed to a loxP site (FIG. 4C). One microliter aliquots of each supercoiled plasmid (about 50 ng crude miniprep DNA) were combined in a ten microliter reaction containing equal parts of lambda integrase buffer (50 mM Tris-HCl, pH 7.8, 70 mM KCl, 5 mM spermidine, 0.5 mM EDTA, 0.25 mg/ml bovine serum albumin) and Cre recombinase buffer (50 mM Tris-HCl, pH 7.5, 33 mM NaCl, 5 mM spermidine, 0.5 mg/ml bovine serum albumin), two units of Cre recombinase, 16 ng integration host factor, and 32 ng lambda integrase. After incubation at 30° C. for 30 minutes and 75° C. for 10 minutes, one microliter was transformed into competent E. coli strain DH5α (Life Technologies, Inc.). Aliquots of transformations were spread on agar plates containing 200 μg/ml kanamycin and incubated at 37° C. overnight. An otherwise identical control reaction contained the Vector Donor plasmid only. The plate receiving 10% of the control reaction transformation gave one colony; the plate receiving 10% of the recombinational cloning reaction gave 144 colonies. These numbers suggested that greater than 99% of the recombinational cloning colonies contained the desired product plasmid. Miniprep DNA made from six recombinational cloning colonies gave the predicted size plasmid (5026 base pairs), CMVProd. Restriction digestion with NcoI gave the fragments predicted for the chloramphenicol acetyl transferase cloned downstream of the CMV promoter for all six plasmids.

Example 3
Subcloned DNA Segments Flanked by attB Sites without Stop Codons
Part I: Background The above examples are suitable for transcriptional fusions, in which transcription crosses recombination sites. However, both attR and loxP sites contain multiple stop codons on both strands, so translational fusions can be difficult, where the coding sequence must cross the recombination sites, (only one reading frame is available on each strand of loxP sites) or impossible (in attR or attL).

A principal reason for subcloning is to fuse protein domains. For example, fusion of the glutathione S-transferase (GST) domain to a protein of interest allows the fusion protein to be purified by affinity chromatography on glutathione agarose (Pharmacia, Inc., 1995 catalog). If the protein of interest is fused to runs of consecutive histidines (for example His6), the fusion protein can be purified by affinity chromatography on chelating resins containing metal ions (Qiagen, Inc.). It is often desirable to compare amino terminal and carboxy terminal fusions for activity, solubility, stability, and the like.

The attB sites of the bacteriophage λ integration system were examined as an alternative to loxP sites, because they are small (25 bp) and have some sequence flexibility (Nash, H. A. et al., Proc. Natl. Acad. Sci. USA 84:4049–4053 (1987). It was not previously suggested that multiple mutations to remove all stop codes would result in useful recombination sites for recombinational subcloning.

Using standard nomenclature for site specific recombination in lambda bacteriophage (Weisber, in Lambda III, Hendrix, et al., eds., Cold Spring Harbor Laboratory, Cold Spring Harbor, N.Y. (1989)), the nucleotide regions that participate in the recombination reaction in an E. coli host cell are represented as follows:

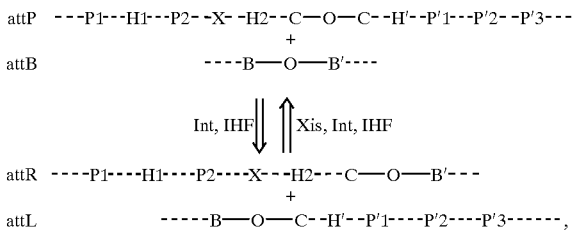

where: O represents the 15 bp core DNA sequence found in both the phage and *E. coli* genomes; B and B' represent approximately 5 bases adjacent to the core in the *E. coli* genome; and P1, H1, P2, X, H2, C, C', H', P'1, P'2, and P'3 represent known DNA sequences encoding protein binding domains in the bacteriophage λ genome.

The reaction is reversible in the presence of the protein Xis (excisionase); recombination between attL and attR precisely excise the λ genome from its integrated state, regenerating the circular λ genome containing attP and the linear *E. coli* genome containing attB.

Part II: Construction and Testing of Plasmids Containing Mutant att Sites

Mutant attL and attR sites were constructed. Importantly, Landy et al. (*Ann. Rev. Biochem.* 58:913 (1989)) observed that deletion of the P1 and H1 domains of attP facilitated the excision reaction and eliminated the integration reaction, thereby making the excision reaction irreversible. Therefore, as mutations were introduced in attR, the P1 and H1 domains were also deleted. attR sites in the present example lack the P1 and H1 regions and have the NdeI site removed (base 27630 changed from C to G), and contain sequences corresponding to bacteriophage λ coordinates 27619–27738 (GenBank release 92.0, bg:LAMCG, "Complete Sequence of Bacteriophage Lambda").

The sequence of attB produced by recombination of wild type attL and attR sites is:

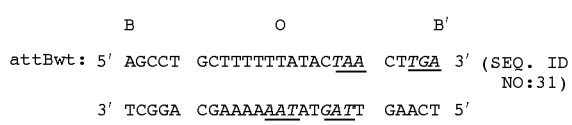

The stop codons are italicized and underlined. Note that sequences of attL, attR, and attP can be derived from the attB sequence and the boundaries of bacteriophage λ contained within attL and attR (coordinates 27619 to 27818).

When mutant attR1 and attL 1 sites were recombined the sequence attB1 was produced (mutations in bold, large font):

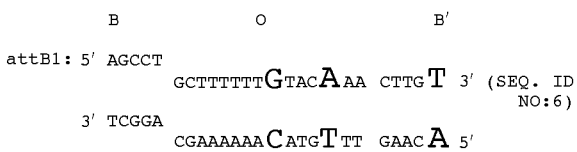

Note that the four stop codons are gone.

When an additional mutation was introduced in the attR1 and attL1 sequences (bold), attR2 and attL2 sites resulted. Recombination of attR2 and attL2 produced the attB2 site:

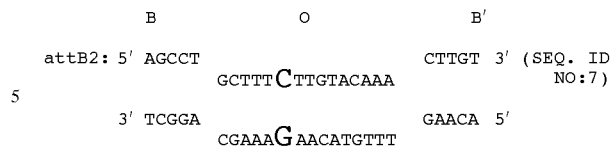

The recombination activities of the above attL and attR sites were assayed as follows. The attB site of plasmid pEZC705 (FIG. 2B) was replaced with attLwt, attL1, or attL2. The attP site of plasmid pEZC726 (FIG. 2C) was replaced with attRwt (lacking regions P1 and H1 ), attR1, or attR2. Thus, the resulting plasmids could recombine via their loxP sites, mediated by Cre, and via their attR and attL sites, mediated by Int, Xis, and IHF. Pairs of plasmids were mixed and reacted with Cre, Int, Xis, and IHF, transformed into *E. coli* competent cells, and plated on agar containing kanamycin. The results are presented in Table 3:

TABLE 3

| Vector donor att site | Gene donor att site | # of kanamycin resistant colonies* |
|---|---|---|
| attRwt (pEZC1301) | None | 1 (background) |
| attRwt (pEZC1301) | attLwt (pEZC1313) | 147 |
| attRwt (pEZC1301) | attL1 (pEZC1317) | 47 |
| attRwt (pEZC1301) | attL2 (pEZC1321) | 0 |
| attR1 (pEZC1305) | None | 1 (background) |
| attR1 (pEZC1305) | attLwt (pEZC1313) | 4 |
| attR1 (pEZC1305) | attL1 (pEZC1317) | 128 |
| attR1 (pEZC1305) | attL2 (pEZC1321) | 0 |
| attR2 (pEZC1309) | None | 9 (background) |
| attR2 (pEZC1309) | attLwt (pEZC1313) | 0 |
| attR2 (pEZC1309) | attL2 (PEZC1317) | 0 |
| attR2 (pEZC1309) | attL2 (pEZC1321) | 209 |

(*1% of each transformation was spread on a kanamycin plate.)

The above data show that whereas the wild type att and att1sites recombine to a small extent, the att1 and att2 sites do not recombine detectably with each other.

Part III. Recombination was demonstrated when the core region of both attB sites flanking the DNA segment of interest did not contain stop codons. The physical state of the participating plasmids was discovered to influence recombination efficiency.

Figure 5A:
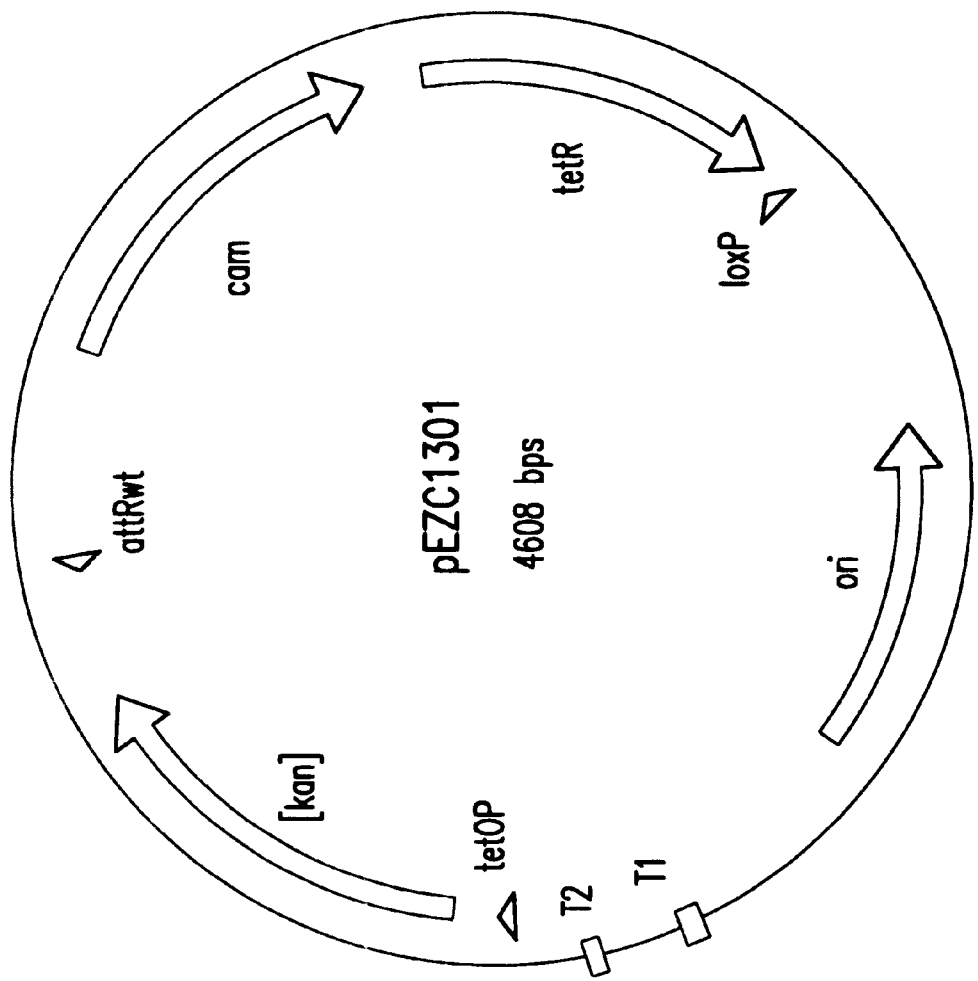
FIG. 5A depicts a vector diagram of pEZC1301.
Figure 5B:
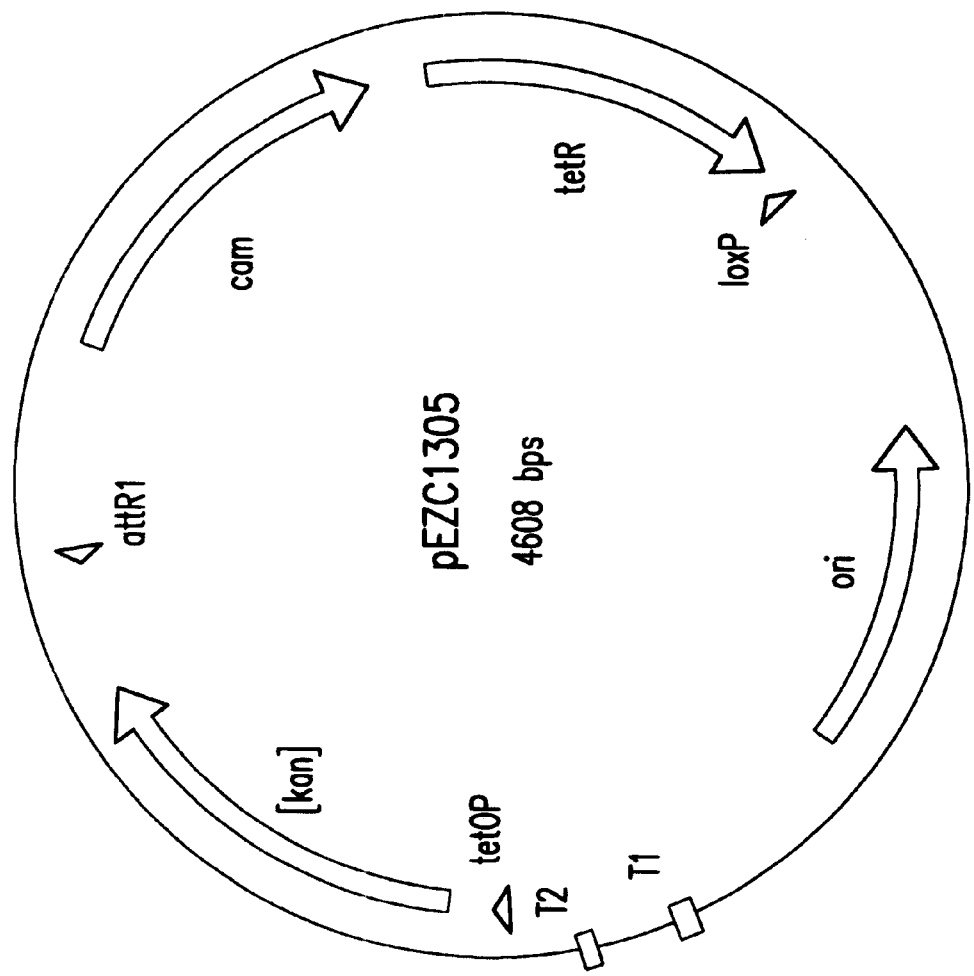
FIG. 5B depicts a vector diagram of pEZC1305.
Figure 5C:
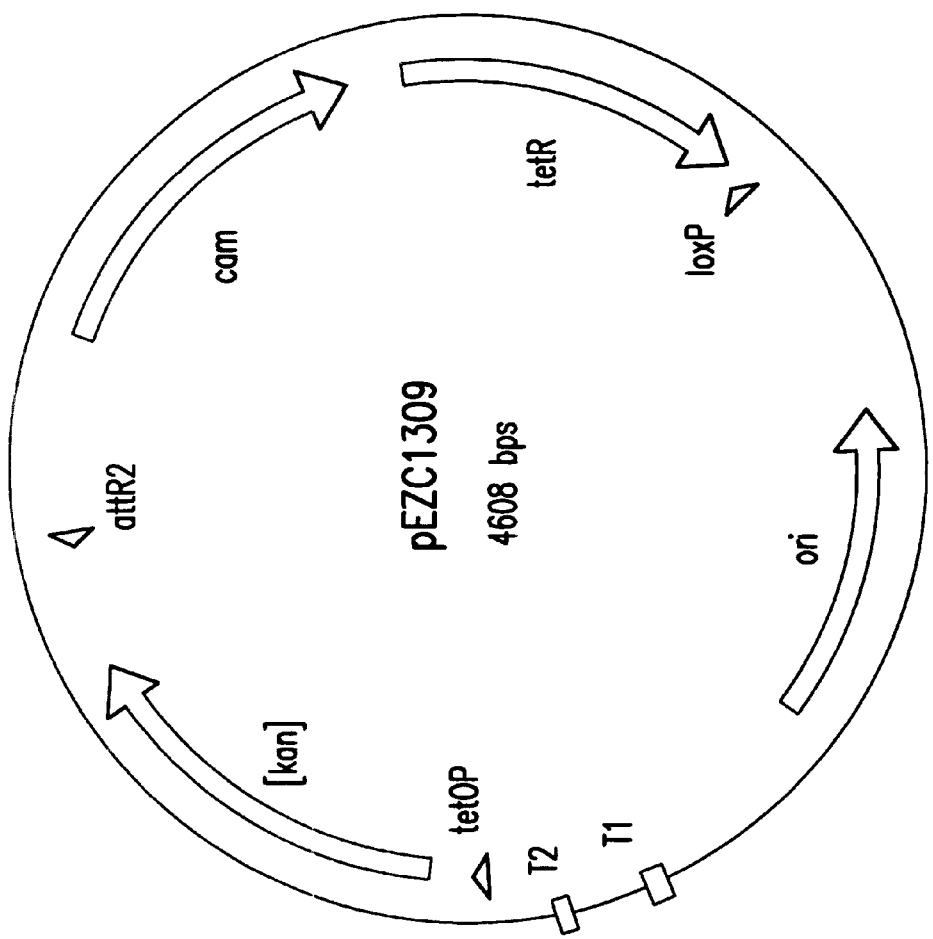
FIG. 5C depicts a vector diagram of pEZC1309.
Figure 5D:
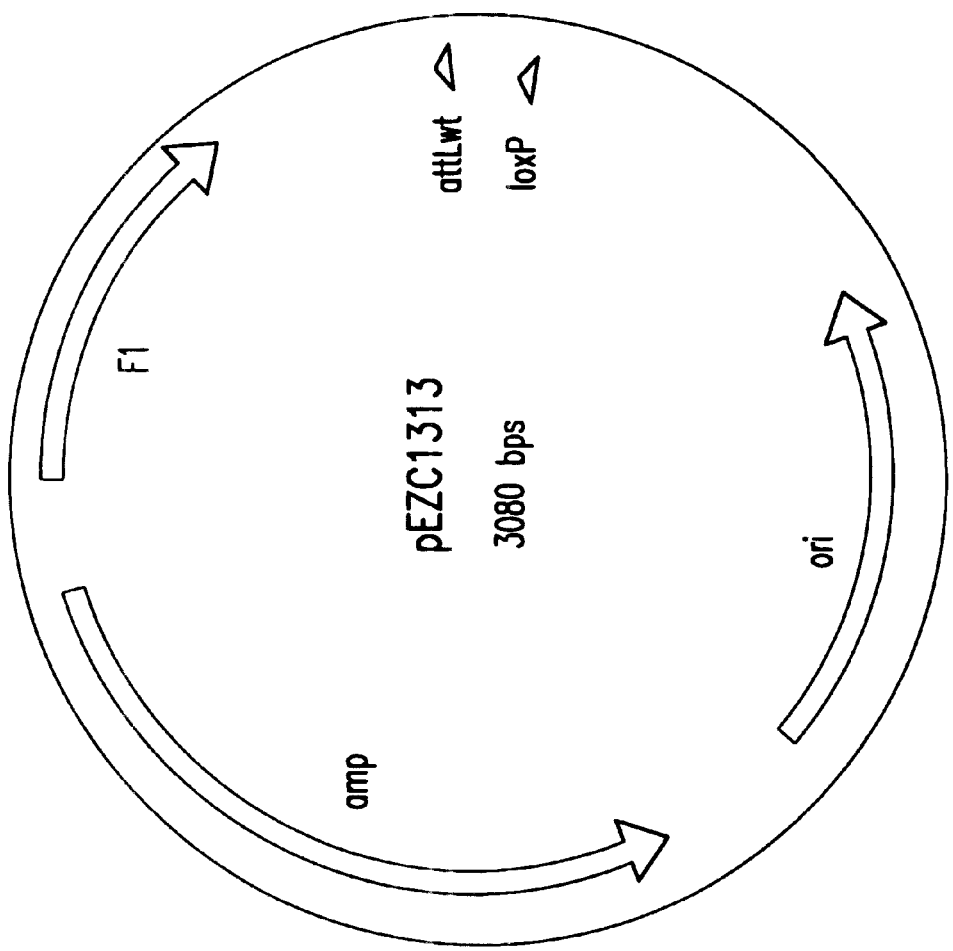
FIG. 5D depicts a vector diagram of pEZC1313.
Figure 5E:
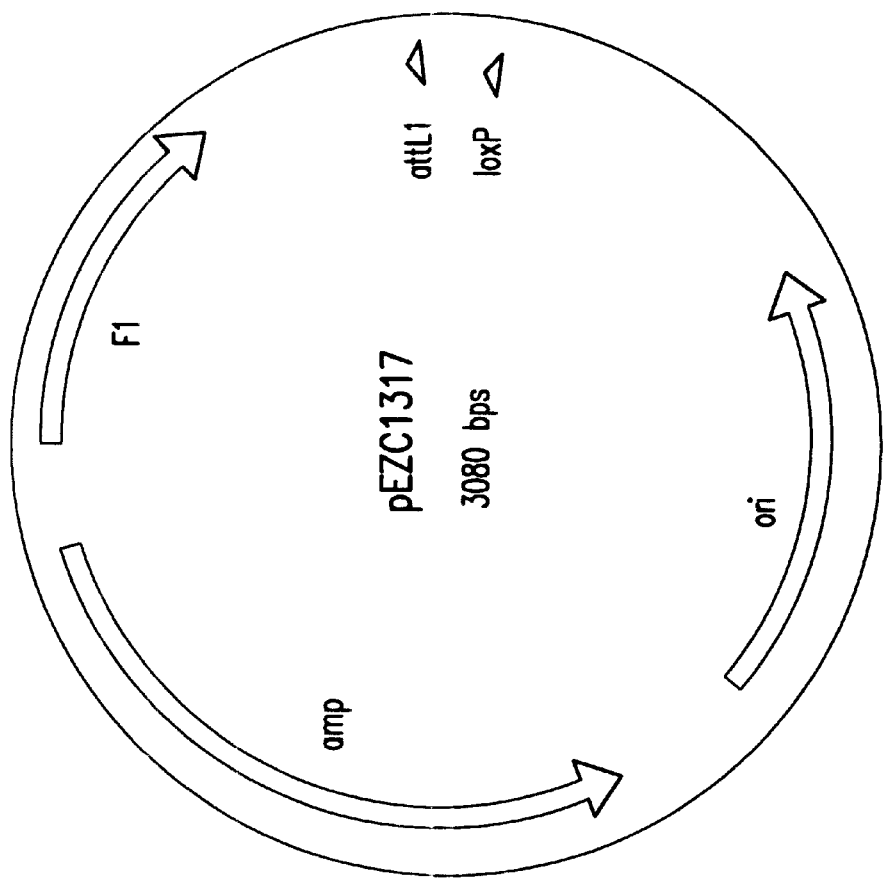
FIG. 5E depicts a vector diagram of pEZC1317.
Figure 5F:
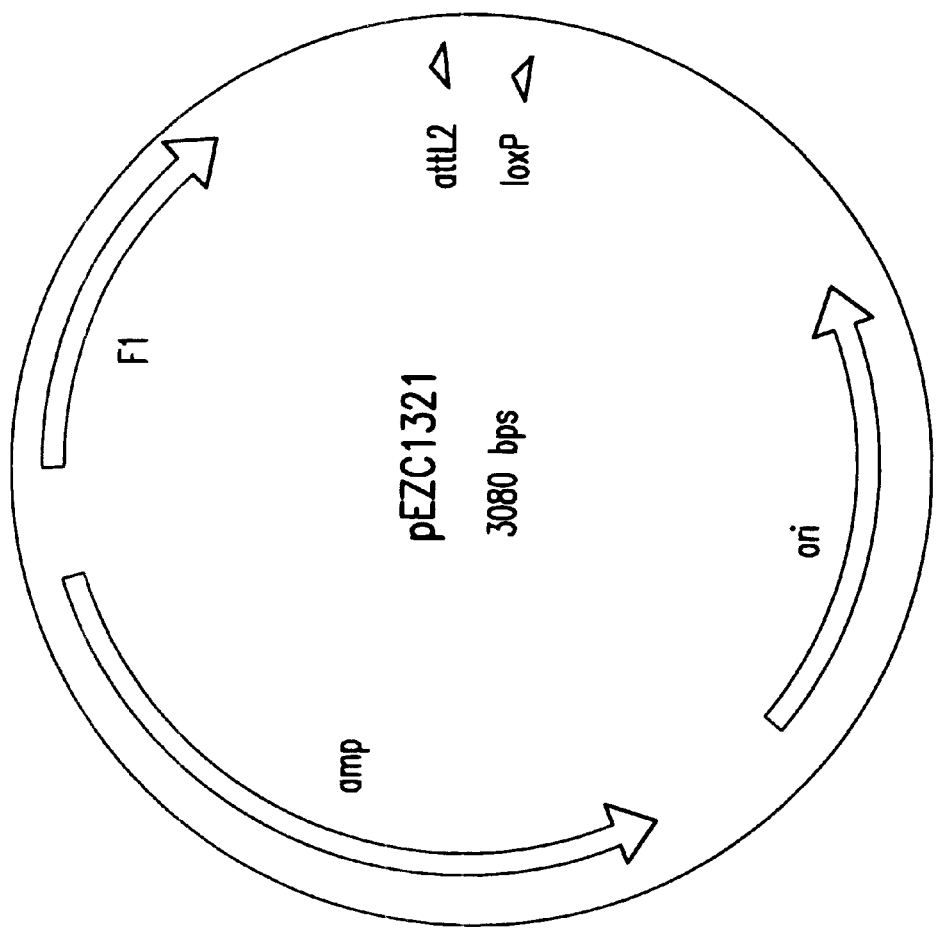
FIG. 5F depicts a vector diagram of pEZC1321.
Figure 5G:
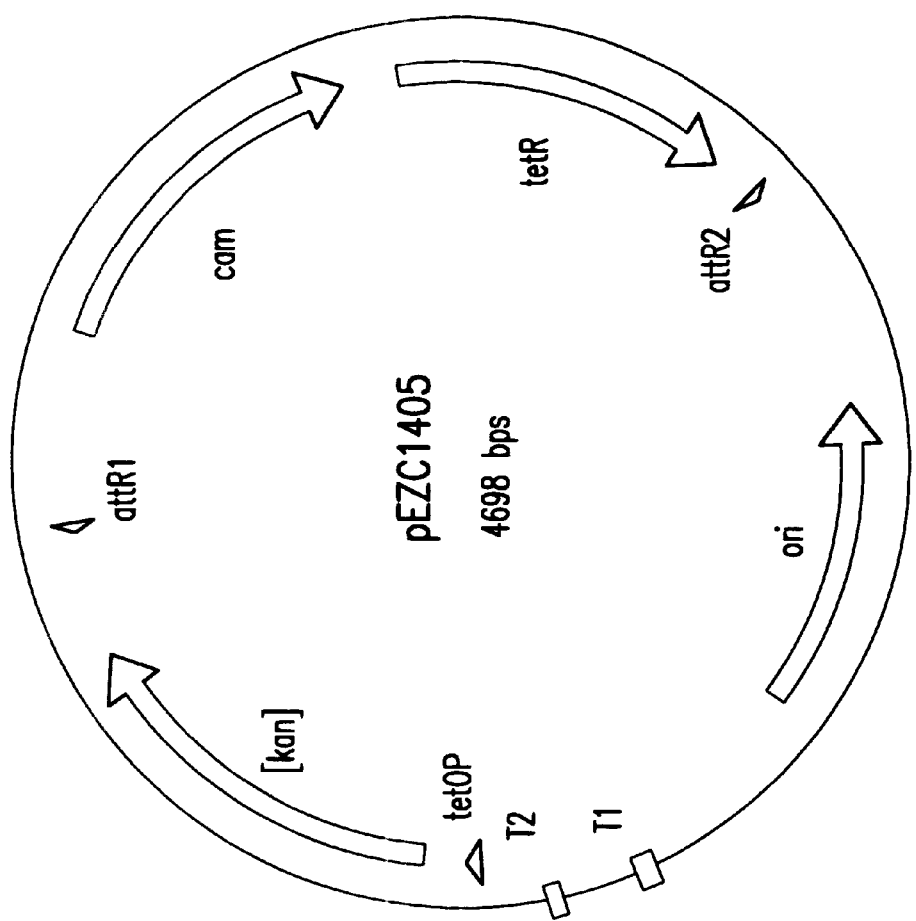
FIG. 5G depicts a vector diagram of pEZC1405.

The appropriate att sites were moved into pEZC705 and pEZC726 to make the plasmids pEZC1405 (FIG. 5G) (attR1 and attR2) and pEZC1502 (FIG. 5H) (attL1 and attL2). The desired DNA segment in this experiment was a copy of the chloramphenicol resistance gene cloned between the two attL sites of pEZC1502. Pairs of plasmids were recombined in vitro using Int, Xis, and IHF (no Cre because no loxP sites were present). The yield of desired kanamycin resistant colonies was determined when both parental plasmids were circular, or when one plasmid was circular and the other linear as presented in Table 4:

TABLE 4

| Vector donor[1] | Gene donor[1] | Kanamycin resistant colonies[2] |
|---|---|---|
| Circular pEZC1405 | None | 30 |
| Circular pEZC1405 | Circular pEZC1502 | 2680 |
| Linear pEZC1405 | None | 90 |

TABLE 4-continued

| Vector donor[1] | Gene donor[1] | Kanamycin resistant colonies[2] |
|---|---|---|
| Linear pEZC1405 | Circular pEZC1502 | 172000 |
| Circular pEZC1405 | Linear pEZC1502 | 73000 |

[1]DNAs were purified with Qiagen columns, concentrations determined by A260, and linearized with Xba I (pEZC1405) or A1wN I (pEZC1502). Each reaction contained 100 ng of the indicated DNA. All reactions (10 µl total) contained 3 µl of enzyme mix (Xis, Int, and IHF). After incubation (45 minutes at 25°, 10 minutes at 65°), one µl was used to transform E. coli DH5α cells.
[2]Number of colonies expected if the entire transformation reaction (1 ml) had been plated. Either 100 µl or 1 µl of the transformations were actually plated.

Analysis: Recombinational cloning using mutant attR and attL sites was confirmed. The desired DNA segment is subcloned between attB sites that do not contain any stop codons in either strand. The enhanced yield of Product DNA (when one parent was linear) was unexpected because of earlier observations that the excision reaction was more efficient when both participating molecules were supercoiled and proteins were limiting (Nunes-Duby et al., Cell 50:779–788 (1987)).

Example 4
Demonstration of Recombinational Cloning without Inverted Repeats
Part I: Rationale The above Example 3 showed that plasmids containing inverted repeats of the appropriate recombination sites (for example, attL1 and attL2 in plasmid pEZC1502) (FIG. 5H) could recombine to give the desired DNA segment flanked by attB sites without stop codons, also in inverted orientation. A concern was the in vivo and in vitro influence of the inverted repeats. For example, transcription of a desired DNA segment flanked by attB sites in inverted orientation could yield a single stranded RNA molecule that might form a hairpin structure, thereby inhibiting translation.

Inverted orientation of similar recombination sites can be avoided by placing the sites in direct repeat arrangement att sites. If parental plasmids each have a wild type attL and wild type attR site, in direct repeat the Int, Xis, and IHF proteins will simply remove the DNA segment flanked by those sites in an intramolecular reaction. However, the mutant sites described in the above Example 3 suggested that it might be possible to inhibit the intramolecular reaction while allowing the intermolecular recombination to proceed as desired.

Figure 5H:
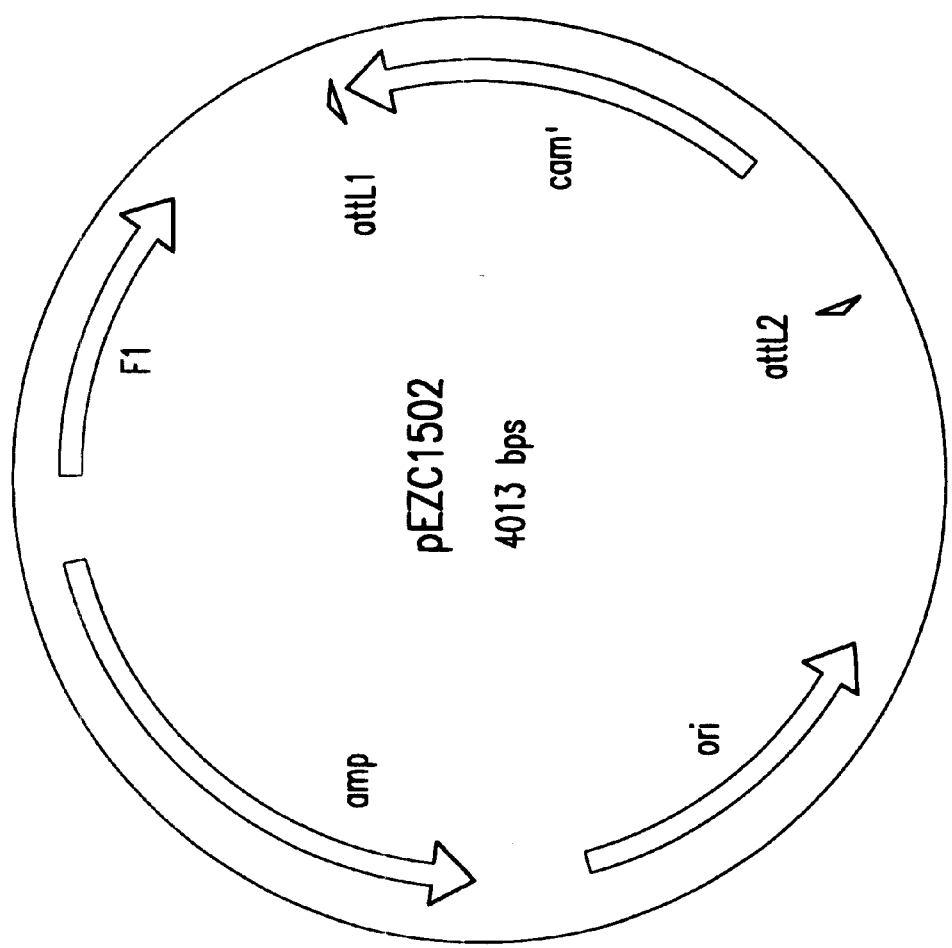
FIG. 5H depicts a vector diagram of pEZC1502.
Figure 6A:
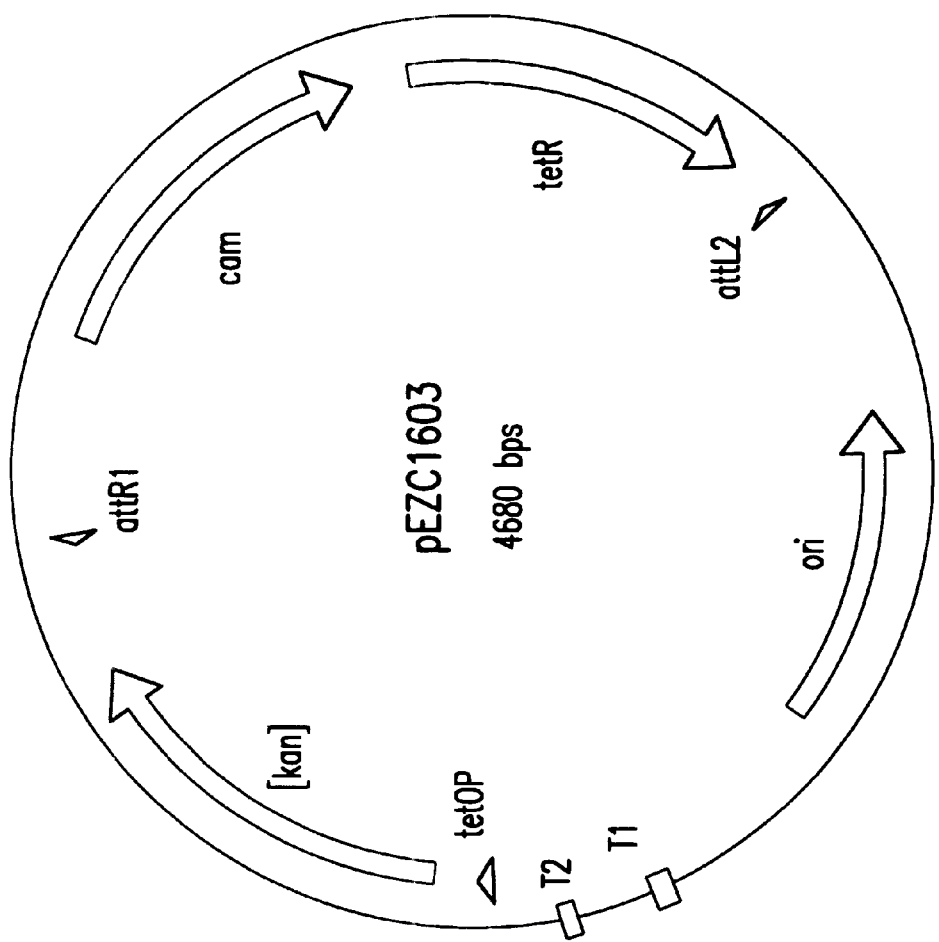
FIG. 6A depicts a vector diagram of pEZC1603.
Figure 6B:
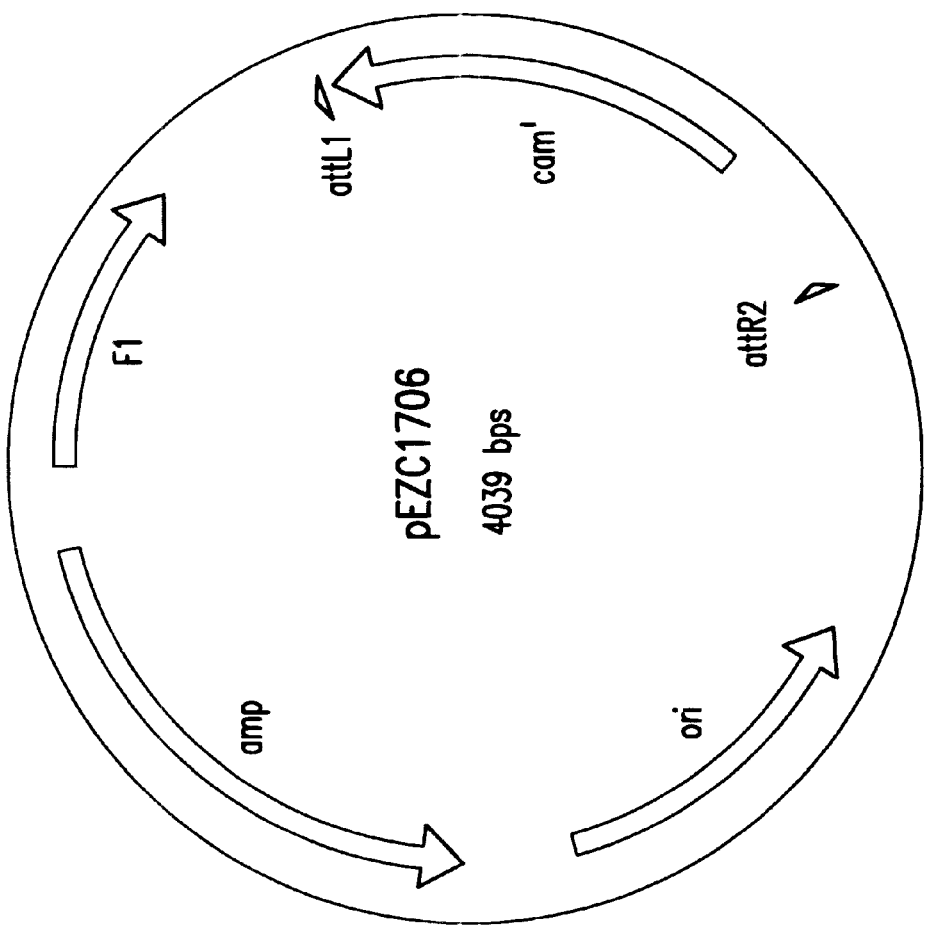
FIG. 6B depicts a vector diagram of pEZC1706.

Part II: Structure of Plasmids without Inverted Repeats for Recombinational Cloning The attR2 sequence in plasmid pEZC1405 (FIG. 5G) was replaced with attL2, in the opposite orientation, to make pEZC1603 (FIG. 6A). The attL2 sequence of pEZC1502 (FIG. 5H) was replaced with attR2, in the opposite orientation, to make pEZC1706 (FIG. 6B). Each of these plasmids contained mutations in the core region that make intramolecular reactions between att1 and att2 cores very inefficient (see Example 3, above).

Plasmids pEZC1405, pEZC1502, pEZC1603 and pEZC1706 were purified on Qiagen columns (Qiagen, Inc.). Aliquots of plasmids pEZC1405 and pEZC1603 were linearized with Xba I. Aliquots of plasmids pEZC1502 and pEZC1706 were linearized with AlwN I. One hundred ng of plasmids were mixed in buffer (equal volumes of 50 mM Tris HCl pH 7.5, 25 mM Tris HCl pH 8.0, 70 mM KCl 5 mM spermidine, 0.5 mM EDTA, 250 µg/ml BSA, 10% glycerol) containing Int (43.5 ng), Xis (4.3 ng) and IHF (8.1 ng) in a final volume of 10 µl. Reactions were incubated for 45 minutes at 25° C., 10 minutes at 65° C., and 1 µl was transformed into E. coli DH5α. After expression, aliquots were spread on agar plates containing 200 µg/ml kanamycin and incubated at 37° C.

Results, expressed as the number of colonies per 1 µl of recombination reaction are presented in Table 5:

TABLE 5

| Vector Donor | Gene Donor | Colonies | Predicted % product |
|---|---|---|---|
| Circular 1405 | — | 100 | — |
| Circular 1405 | Circular 1502 | 3740 | 3640/3740 = 97% |
| Linear 1405 | — | 90 | — |
| Linear 1405 | Circular 1502 | 172,000 | 171,910/172,000 = 99.9% |
| Circular 1405 | Linear 1502 | 73,000 | 72,900/73,000 = 99.9% |
| Circular 1603 | — | 80 | — |
| Circular 1603 | Circular 1706 | 410 | 330/410 = 80% |
| Linear 1603 | — | 270 | — |
| Linear 1603 | Circular 1706 | 7000 | 6730/7000 = 96% |
| Circular 1603 | Linear 1706 | 10,800 | 10,530/10,800 = 97% |

Analysis. In all configurations, i.e., circular or linear, the pEZC1405×pEZC1502 pair (with att sites in inverted repeat configuration) was more efficient than pEZC1603× pEZC1706 pair (with att sites mutated to avoid hairpin formation). The pEZC1603×pEZC1706 pair gave higher backgrounds and lower efficiencies than the pEZC1405× pEZC1502 pair. While less efficient, 80% or more of the colonies from the pEZC1603×pEZC1706 reactions were expected to contain the desired plasmid product. Making one partner linear stimulated the reactions in all cases.
Part III: Confirmation of Product Plasmids' Structure Six colonies each from the linear pEZC1405 (FIG. 5G)× circular pEZC1502 (FIG. 5H), circular pEZC1405×linear pEZC1502, linear pEZC1603 (FIG. 6A)×circular pEZC1706 (FIG. 6B), and circular pEZC1603×linear pEZC1706 reactions were picked into rich medium and miniprep DNAs were prepared. Diagnostic cuts with Ssp I gave the predicted restriction fragments for all 24 colonies.

Analysis. Recombination reactions between plasmids with mutant attL and attR sites on the same molecules gave the desired plasmid products with a high degree of specificity.

Example 5
Recombinational Cloning with a Toxic Gene
Part I: Background

Restriction enzyme Dpn I recognizes the sequence GATC and cuts that sequence only if the A is methylated by the dam methylase. Most commonly used E. coli strains are dam+. Expression of Dpn I in dam+ strains of E. coli is lethal because the chromosome of the cell is chopped into many pieces. However, in dam− cells expression of Dpn I is innocuous because the chromosome is immune to Dpn I cutting.

In the general recombinational cloning scheme, in which the vector donor contains two segments C and D separated by recombination sites, selection for the desired product depends upon selection for the presence of segment D, and the absence of segment C. In the original Example segment D contained a drug resistance gene (Km) that was negatively controlled by a repressor gene found on segment C. When C was present, cells containing D were not resistant to kanamycin because the resistance gene was turned off.

The Dpn I gene is an example of a toxic gene that can replace the repressor gene of the above embodiment. If segment C expresses the Dpn I gene product, transforming plasmid CD into a dam⁺ host kills the cell. If segment D is transferred to a new plasmid, for example by recombinational cloning, then selecting for the drug marker will be successful because the toxic gene is no longer present.

Part II: Construction of a Vector Donor Using Dpn I as a Toxic Gene

The gene encoding Dpn I endonuclease was amplified by PCR using primers 5'CCA CCA CAA ACG CGT CCA TGG AAT TAC ACT TTA ATT TAG3' (SEQ. ID NO: 17) and 5'CCA CCA CAA GTC GAC GCA TGC CGA CAG CCT TCC AAA TGT3' (SEQ. ID NO: 18) and a plasmid containing the Dpn I gene (derived from plasmids obtained from Sanford A. Lacks, Brookhaven National Laboratory, Upton, N.Y.; also available from American Type Culture Collection as ATCC 67494) as the template.

Additional mutations were introduced into the B and B' regions of attL and attR, respectively, by amplifing existing attL and attR domains with primers containing the desired base changes. Recombination of the mutant attL3 (made with oligo Xis115) and attR3 (made with oligo Xis112) yielded attB3 with the following sequence (differences from attB1 in bold):

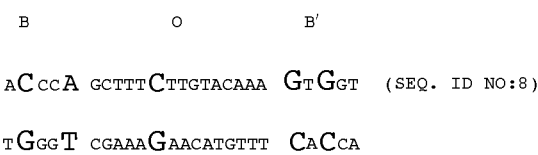

Figure 7A:
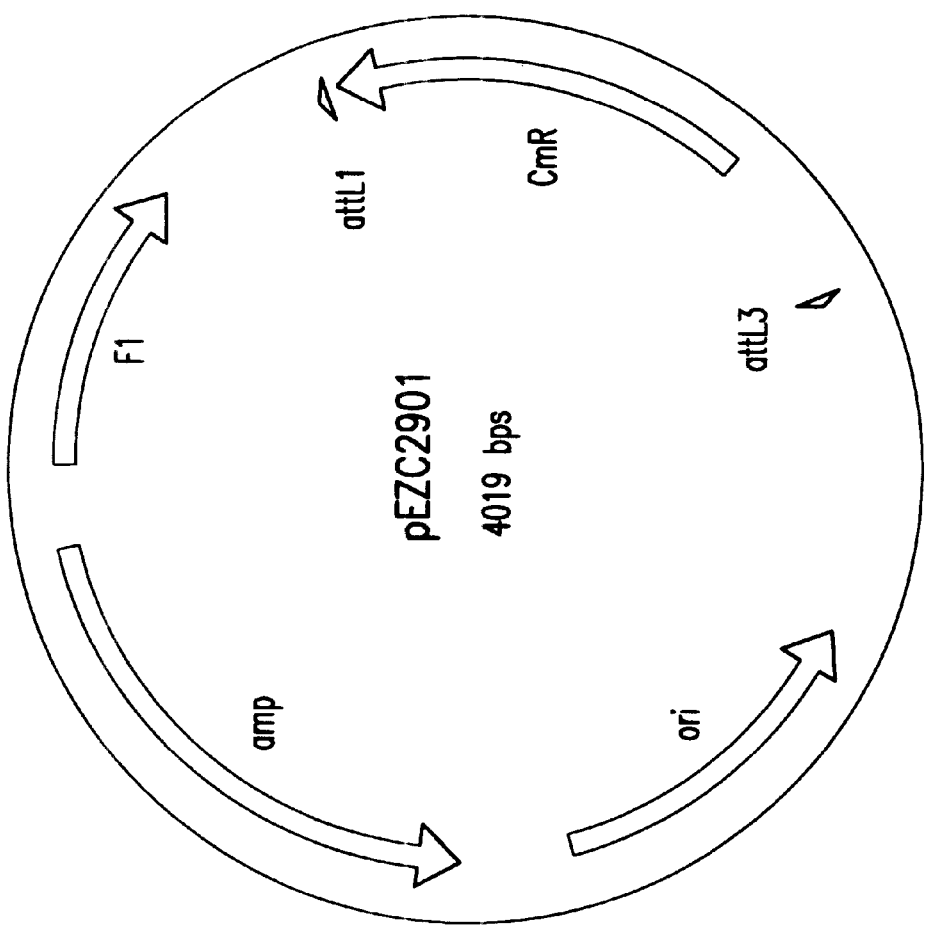
FIG. 7A depicts a vector diagram of pEZC2901.
Figure 7B:
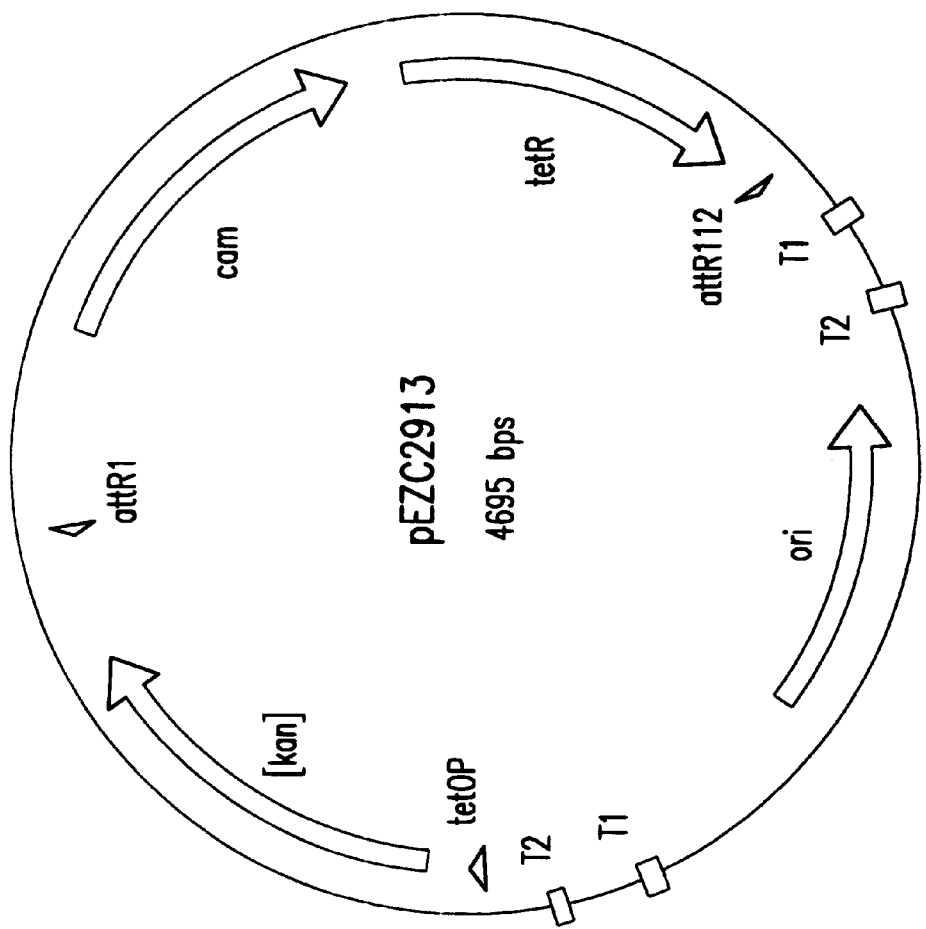
FIG. 7B depicts a vector diagram of pEZC2913
Figure 7C:
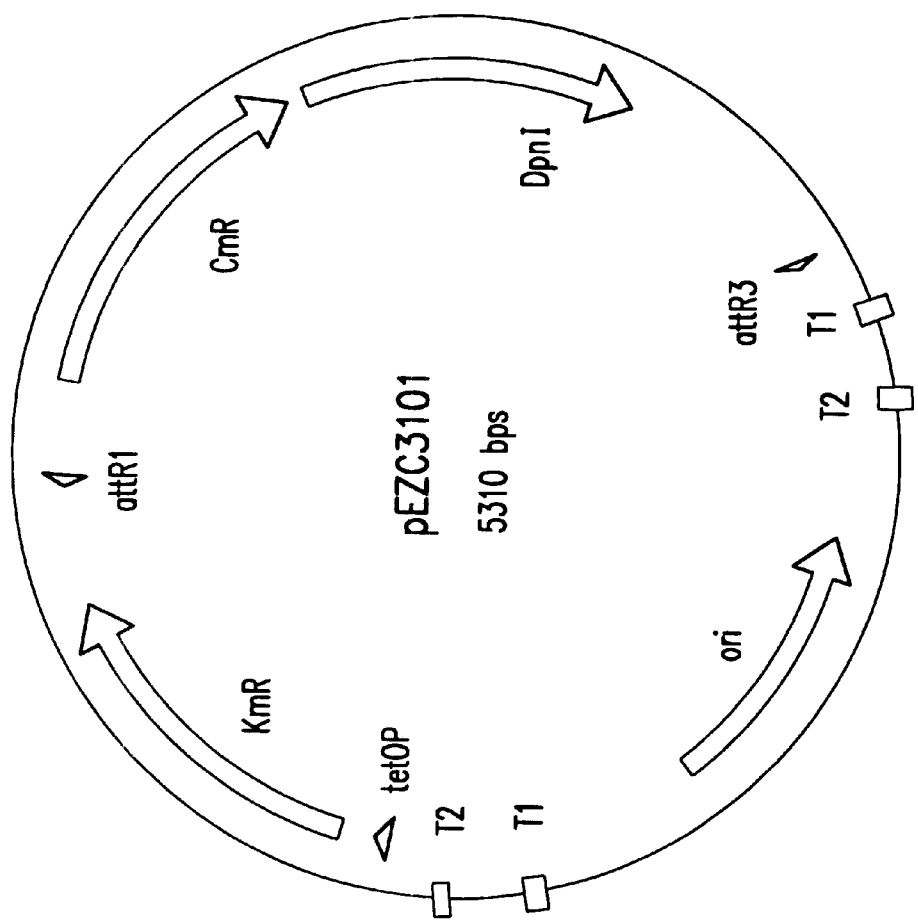
FIG. 7C depicts a vector diagram of pEZC3101.

The attL3 sequence was cloned in place of attL2 of an existing Gene Donor plasmid to give the plasmid pEZC2901 (FIG. 7A). The attR3 sequence was cloned in place of attR2 in an existing Vector Donor plasmid to give plasmid pEZC2913 (FIG. 7B) Dpn I gene was cloned into plasmid pEZC2913 to replace the tet repressor gene. The resulting Vector Donor plasmid was named pEZC3101 (FIG. 7C). When pEZC3101 was transformed into the dam⁻ strain SCS110 (Stratagene), hundreds of colonies resulted. When the same plasmid was transformed into the dam⁺ strain DH5α, only one colony was produced, even though the DH5α cells were about 20 fold more competent than the SCS110 cells. When a related plasmid that did not contain the Dpn I gene was transformed into the same two cell lines, 28 colonies were produced from the SCS110 cells, while 448 colonies resulted from the DH5α cells. This is evidence that the Dpn I gene is being expressed on plasmid pEZC3101 (FIG. 7C), and that it is killing the dam⁺ DH5α cells but not the dam⁻ SCS110 cells.

Part III: Demonstration of Recombinational Cloning Using Dpn I Selection

Figure 7D:
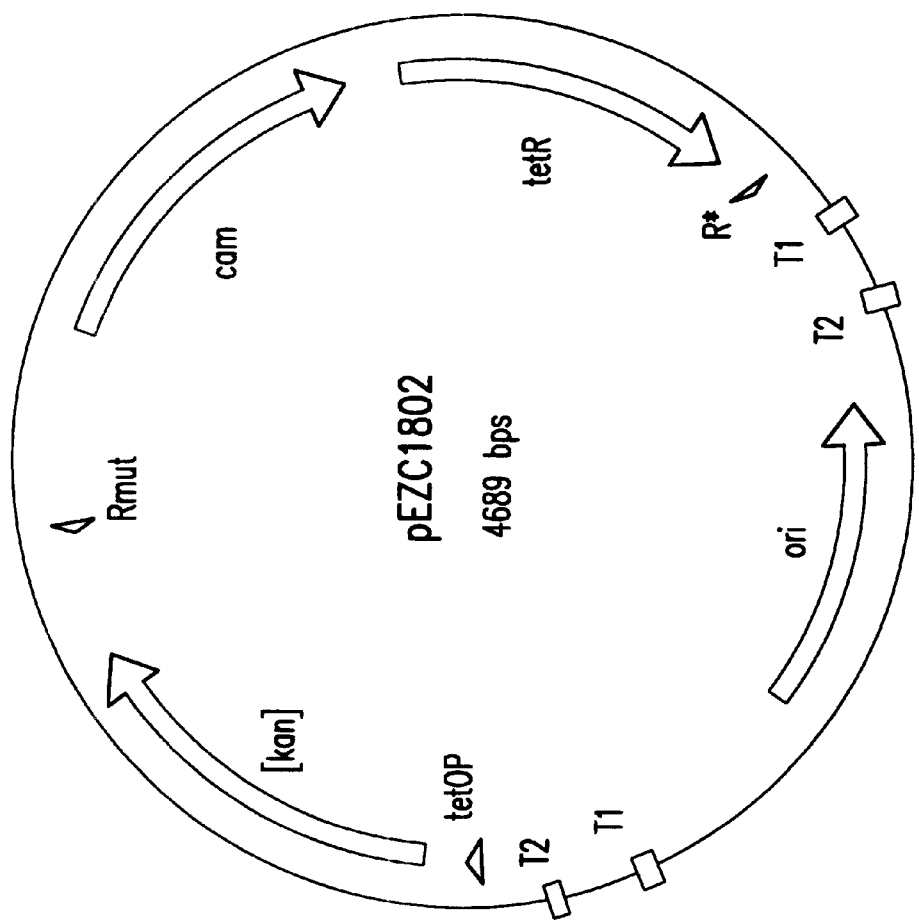
FIG. 7D depicts a vector diagram of pEZC1802.

A pair of plasmids was used to demonstrate recombinational cloning with selection for product dependent upon the toxic gene Dpn I. Plasmid pEZC3101 (FIG. 7C) was linearized with Mlu I and reacted with circular plasmid pEZC2901 (FIG. 7A). A second pair of plasmids using selection based on control of drug resistance by a repressor gene was used as a control: plasmid pEZC1802 (FIG. 7D) was linearized with Xba I and reacted with circular plasmid pEZC1502 (FIG. 5H). Eight ricroliter reactions containing the same buffer and proteins Xis, Int, and IHF as in previous examples were incubated for 45 minutes at 25° C., then 10 minutes at 75° C., and 1 μl aliquots were transformed into DH5α (i.e., dam+) competent cells, as presented in Table 6.

TABLE 6

| Reaction # | Vector donor | Basis of selection | Gene donor | Colonies |
|---|---|---|---|---|
| 1 | pEZC3101/Mlu | Dpn I toxicity | — | 3 |
| 2 | pEZC3101/Mlu | Dpn I toxcity | Circular pEZC2901 | 4000 |
| 3 | pEZC1802/Xba | Tet repressor | — | 0 |
| 4 | pEZC1802/Xba | Tet repressor | Circular pEZC1502 | 12100 |

Miniprep DNAs were prepared from four colonies from reaction #2, and cut with restriction enzyme Ssp I. All gave the predicted fragments.

Analysis: Subcloning using selection with a toxic gene was demonstrated. Plasmids of the predicted structure were produced.

Example 6

Cloning of Genes with Uracil DNA Glycosylase and Subcloning of the Genes with Recombinational Cloning to Make Fusion Proteins Part I: Converting an Existing Expression Vector to a Vector Donor for Recombinational Cloning A cassette useful for converting existing vectors into functional Vector Donors was made as follows. Plasmid pEZC3101 (FIG. 7C) was digested with Apa I and Kpn I, treated with T4 DNA polymerase and dNTPs to render the ends blunt, further digested with Sma I, Hpa I, and AlwN I to render the undesirable DNA fragments small, and the 2.6 kb cassette containing the attR1—Cm^R—Dpn I—attR—3 domains was gel purified. The concentration of the purified cassette was estimated to be about 75 ng DNA/μl.

Figure 8A:
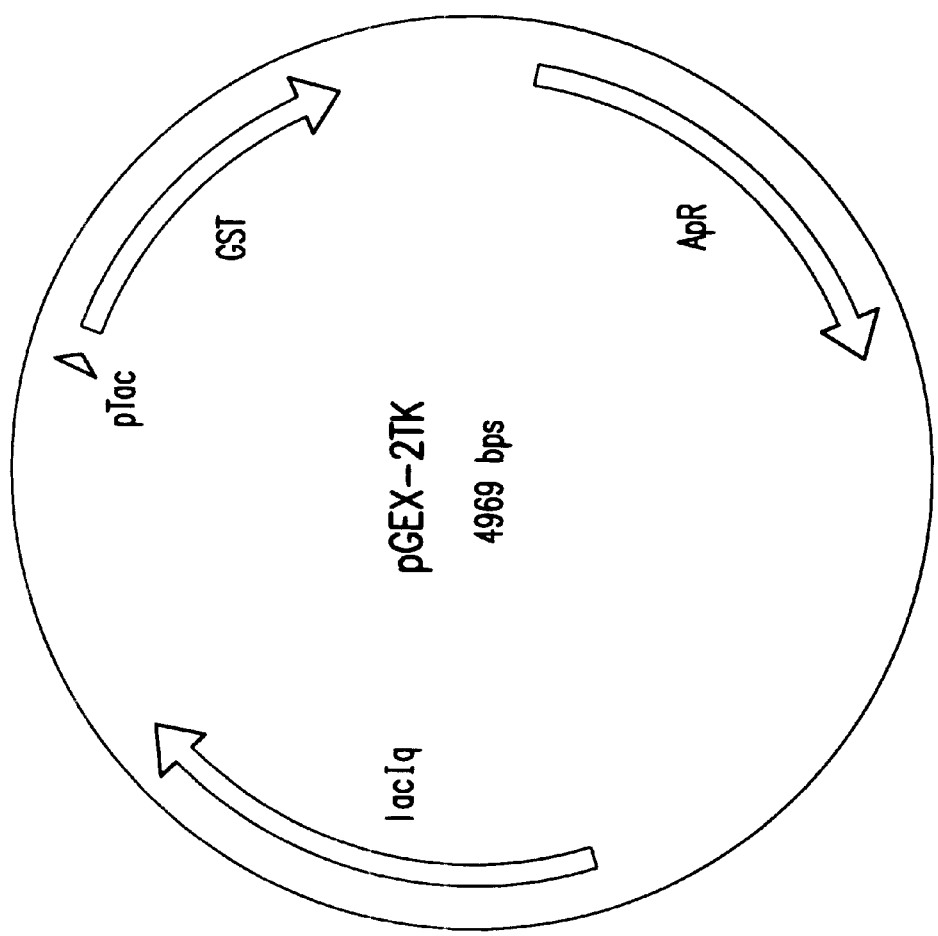
FIG. 8A depicts a vector diagram of pGEX-2TK.
Figure 8B:
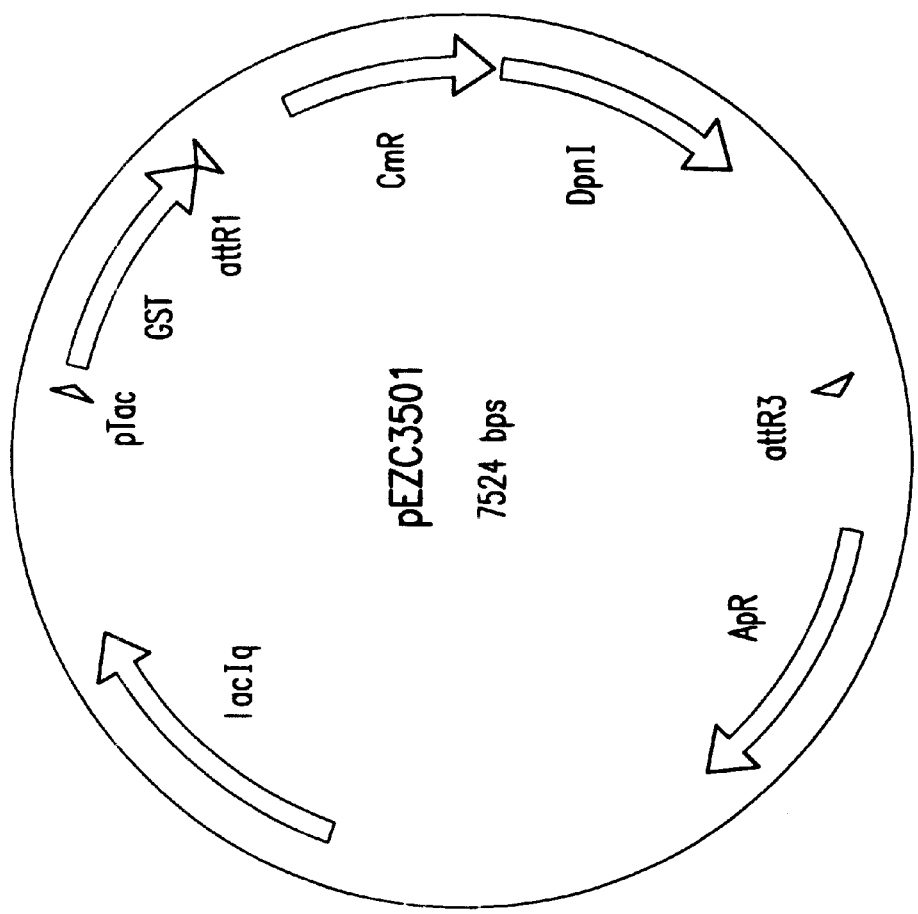
FIG. 8B depicts a vector diagram of pEZC3501.

Plasmid pGEX-2TK (FIG. 8A) (Pharmacia) allows fusions between the protein glutathione S transferase and any second coding sequence that can be inserted in its multiple cloning site. pGEX-2TK DNA was digested with Sma I and treated with alkaline phosphatase. About 75 ng of the above purified DNA cassette was ligated with about 100 ng of the pGEX-2TK vector for 2.5 hours in a 5 μl ligation, then 1 μl was transformed into competent BRL 3056 cells (a dam⁻ derivative of DH10B; dam⁻ strains commercially available include DM1 from Life Technologies, Inc., and SCS 110 from Stratagene). Aliquots of the transformation mixture were plated on LB agar containing 100 μg/ml ampicillin (resistance gene present on pGEX-2TK) and 30 μg/ml chloramphenicol (resistance gene present on the DNA cassette). Colonies were picked and miniprep DNAs were made. The orientation of the cassette in pGEX-2TK was determined by diagnostic cuts with EcoR I. A plasmid with the desired orientation was named pEZC3501 (FIG. 8B).

Part II: Cloning Reporter Genes Into an Recombinational Cloning Gene Donor Plasmid in Three Reading Frames Uracil DNA glycosylase (UDG) cloning is a method for cloning PCR amplification products into cloning vectors (U.S. Pat. No. 5,334,515, entirely incorporated herein by reference). Briefly, PCR amplification of the desired DNA segment is performed with primers that contain uracil bases in place of thymidine bases in their 5' ends. When such PCR products are incubated with the enzyme UDG, the uracil bases are specifically removed. The loss of these bases weakens base pairing in the ends of the PCR product DNA, and when incubated at a suitable temperature (e.g., 37° C.), the ends of such products are largely single stranded. If such incubations are done in the presence of linear cloning vectors containing protruding 3' tails that are complementary to the 3' ends of the PCR products, base pairing efficiently anneals the PCR products to the cloning vector.

When the annealed product is introduced into *E. coli* cells by transformation, in vivo processes efficiently convert it into a recombinant plasmid.

Figure 8C:
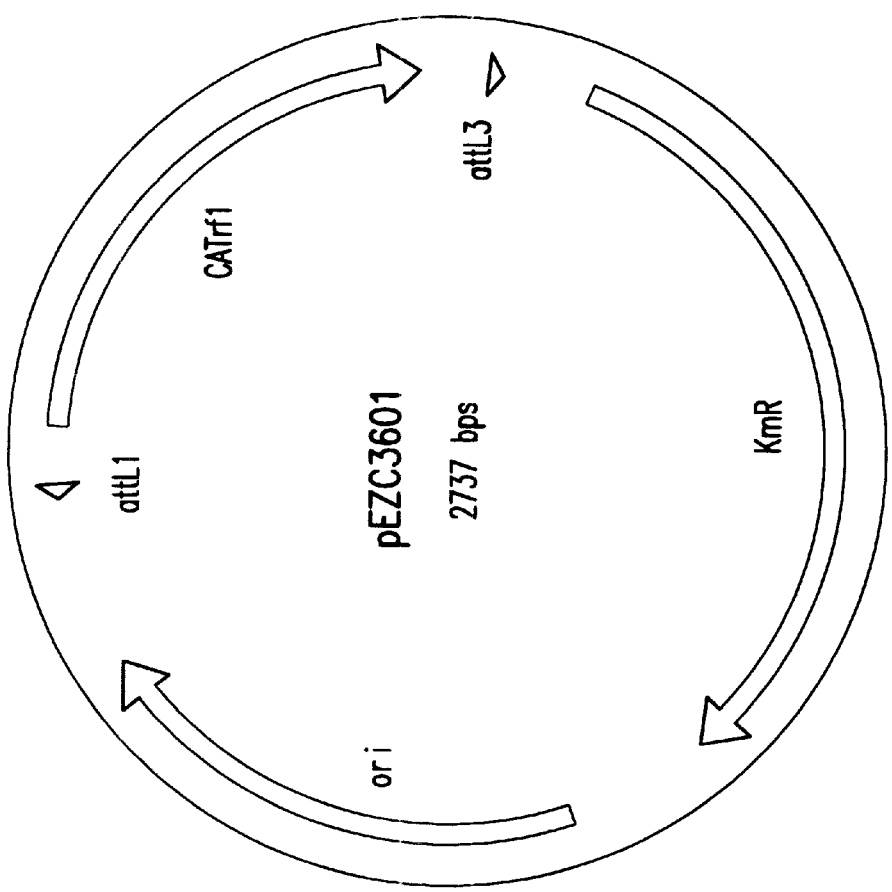
FIG. 8C depicts a vector diagram of pEZC3601.
Figure 8D:
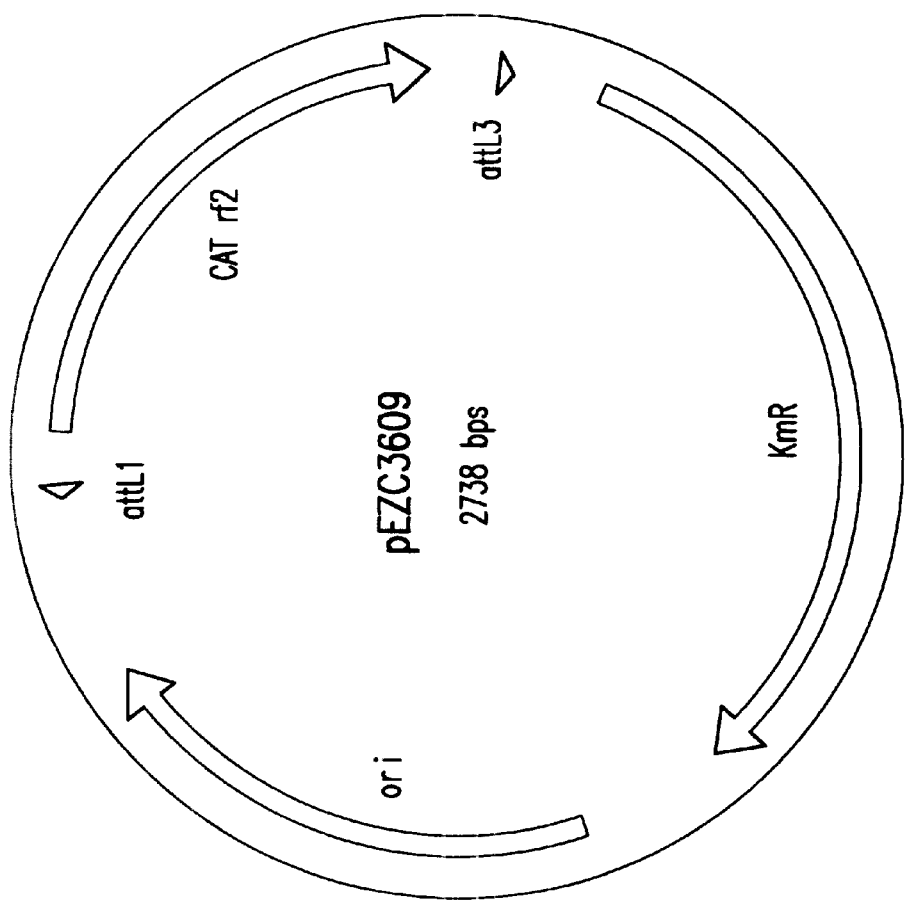
FIG. 8D depicts a vector diagram of pEZC3609.
Figure 8E:
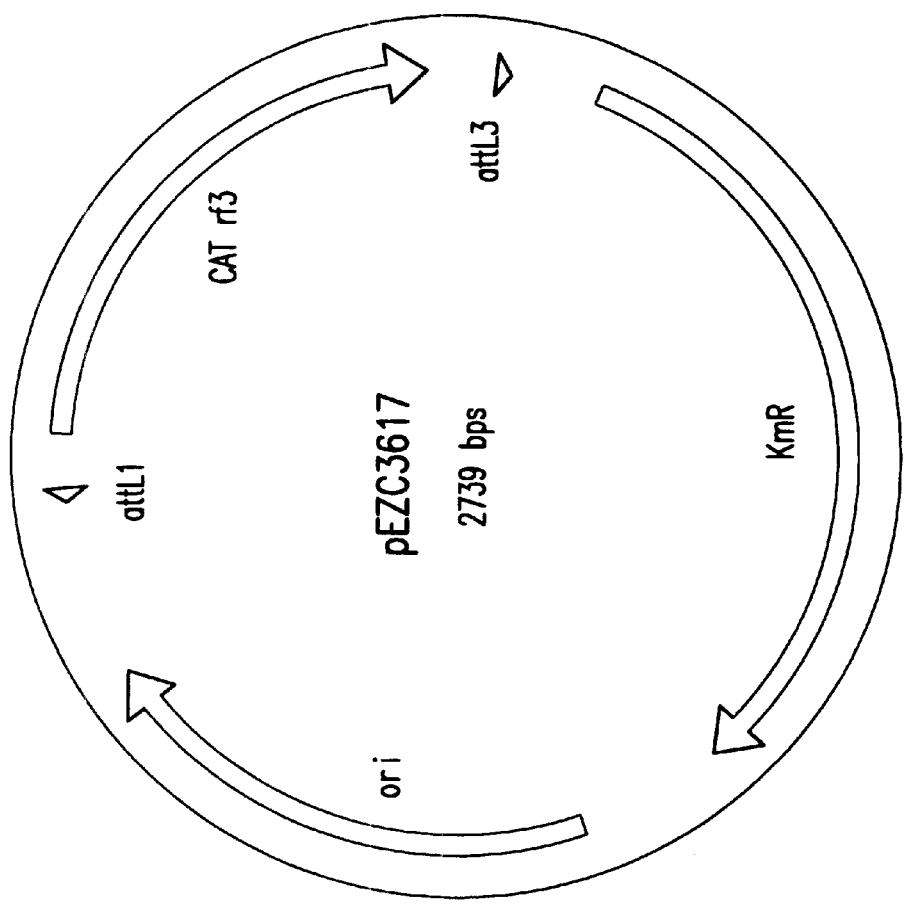
FIG. 8E depicts a vector diagram of pEZC3617.
Figure 8F:
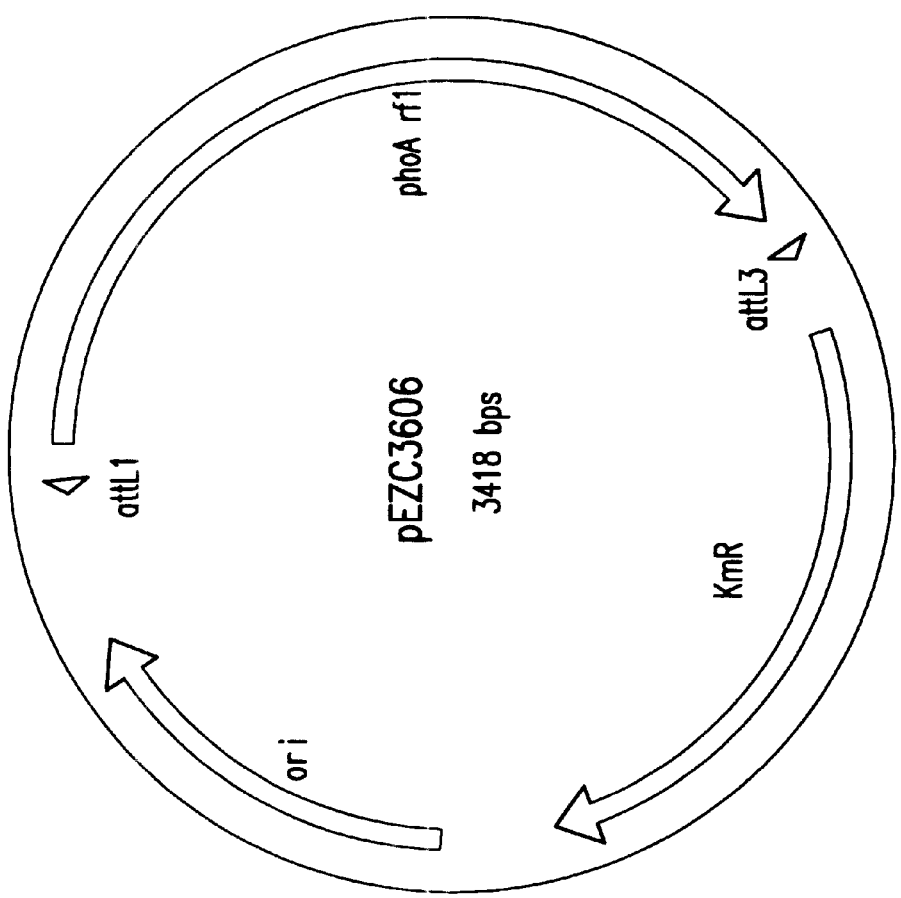
FIG. 8F depicts a vector diagram of pEZC3606.
Figure 8G:
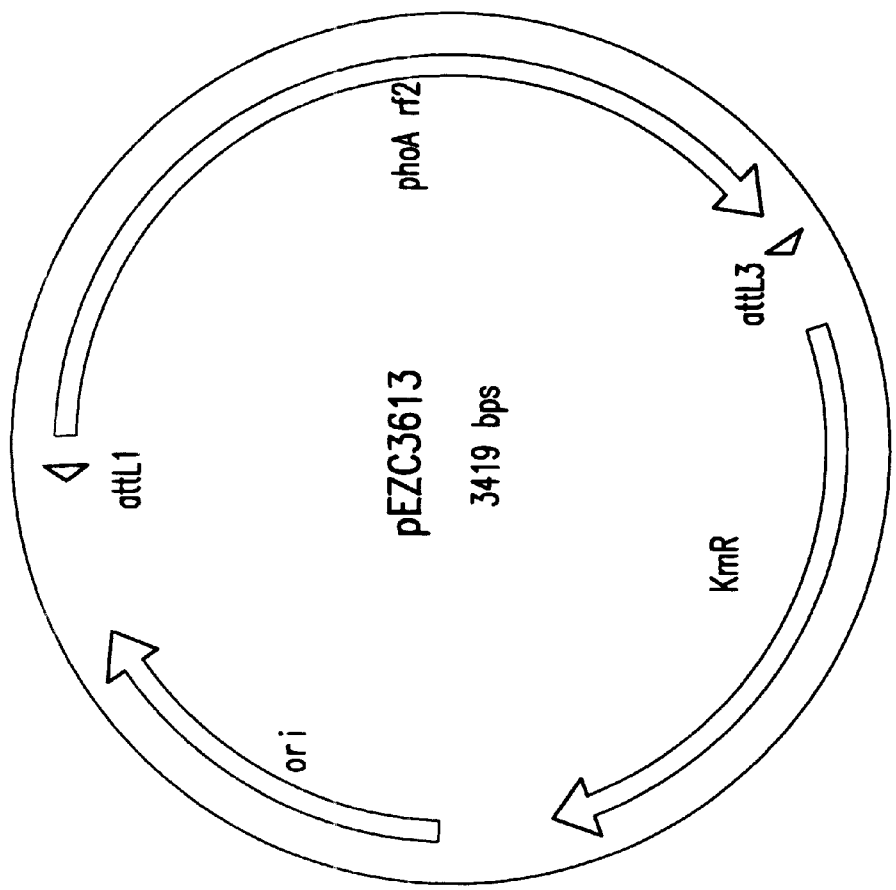
FIG. 8G depicts a vector diagram of pEZC3613.

UDG cloning vectors that enable cloning of any PCR product in all three reading frames were prepared from pEZC3201 (FIG. 8K) as follows. Eight oligonucleotides were obtained from Life Technologies, Inc. (all written 5'→3': rf1 top (GGCC GAT TAC GAT ATC CCA ACG ACC GAA AAC CTG.TAT TTT CAG GGT) (SEQ. ID NO:19), rf1 bottom (CAG OTT TTC GGT CGT TGG GAT ATC GTA ATC)(SEQ. ID NO:20), rf2 top (GGCCA GAT TAC GAT ATC CCA ACG ACC GAA AAC CTG TAT TTT CAG GGT)(SEQ. ID NO:21), rf2 bottom (CAG GTT TTC GGT CGT TGG GAT ATC GTA ATC T)(SEQ. ID NO:22), rf3 top (GGCCAA GAT TAC GAT ATC CCA ACG ACC GAA AAC CTG TAT TTT CAG GGT)(SEQ. ID NO:23), rf3 bottom (CAG GTT TTC GGT CGT TTG GAT ATC GTA ATC TT)(SEQ. ID NO:24), carboxy top (ACC GTT TAC GTG GAC)(SEQ. ID NO:25) and carboxy bottom (TCGA GTC CAC GTA AAC GGT TCC CAC TTA TTA)(SEQ. ID NO:26). The rf1, 2, and 3 top strands and the carboxy bottom strand were phosphorylated on their 5' ends with T4 polynucleotide kinase, and then the complementary strands of each pair were hybridized. Plasmid pEZC3201 (FIG. 8K) was cut with Not I and Sal I, and aliquots of cut plasmid were mixed with the carboxy-oligo duplex (Sal I end) and either the rf1, rf2, or rf3 duplexes (Not I ends) (10 µg cut plasmid (about 5 pmol) mixed with 250 pmol carboxy oligo duplex, split into three 20 µl volumes, added 5 µl (250 pmol) of rf1, rf2, or rf3 duplex and 2 µl=2 units T4 DNA ligase to each reaction). After 90 minutes of ligation at room temperature, each reaction was applied to a preparative agarose gel and the 2.1 kb vector bands were eluted and dissolved in 50 µl of TE.

Part III: PCR of CAT and phoA Genes

Primers were obtained from Life Technologies, Inc., to amplify the chloramphenicol acetyl transferase (CAT) gene from plasmid pACYC184, and phoA, the alkaline phosphatase gene from *E. coli* . The primers had 12-base 5' extensions containing uracil bases, so that treatment of PCR products with uracil DNA glycosylase (UDG) would weaken base pairing at each end of the DNAs and allow the 3' strands to anneal with the protruding 3' ends of the rf1, 2, and 3 vectors described above. The sequences of the primers (all written 5'→3') were: CAT left, UAU UUU CAG GGU ATG GAG AAA AAA ATC ACT GGA TAT ACC (SEQ. ID NO:27); CAT right, UCC CAC UUA UUA CGC CCC GCC CTG CCA CTC ATC (SEQ. ID NO:28); phoA left, UAU UUU CAG GGU ATG CCT GTT CTG GAA AAC CGG (SEQ. ID NO:29); and phoA right, UCC CAC UUA UUA TTT CAG CCC CAG GGC GGC TTT C (SEQ. ID NO:30). The primers were then used for PCR reactions using known method steps (see, e.g., U.S. Pat. No. 5,334,515, entirely incorporated herein by reference), and the polymerase chain reaction amplification products obtained with these primers comprised the CAT or phoA genes with the initiating ATGs but without any transcriptional signals. In addition, the uracil-containing sequences on the amino termini encoded the cleavage site for TEV protease (Life Technologies, Inc.) and those on the carboxy terminal encoded consecutive TAA nonsense codons.

Figure 8H:
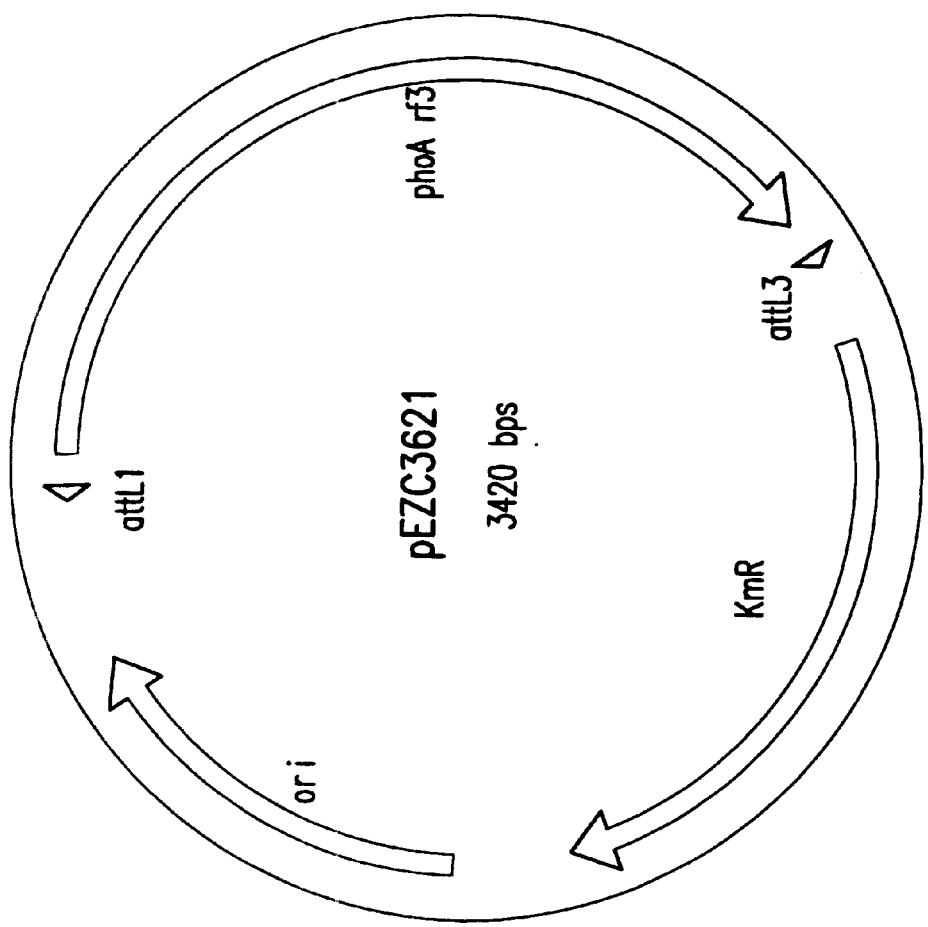
FIG. 8H depicts a vector diagram of pEZC3621.
Figure 8I:
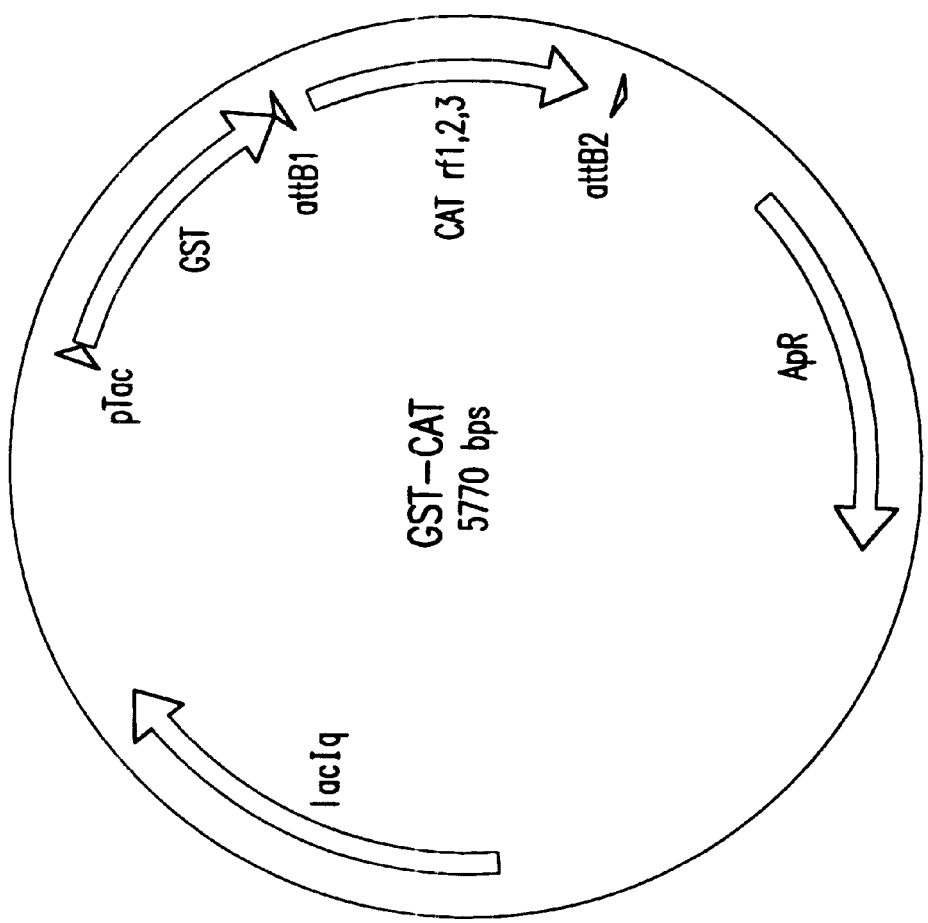
FIG. 8I depicts a vector diagram of GST-CAT.
Figure 8K:
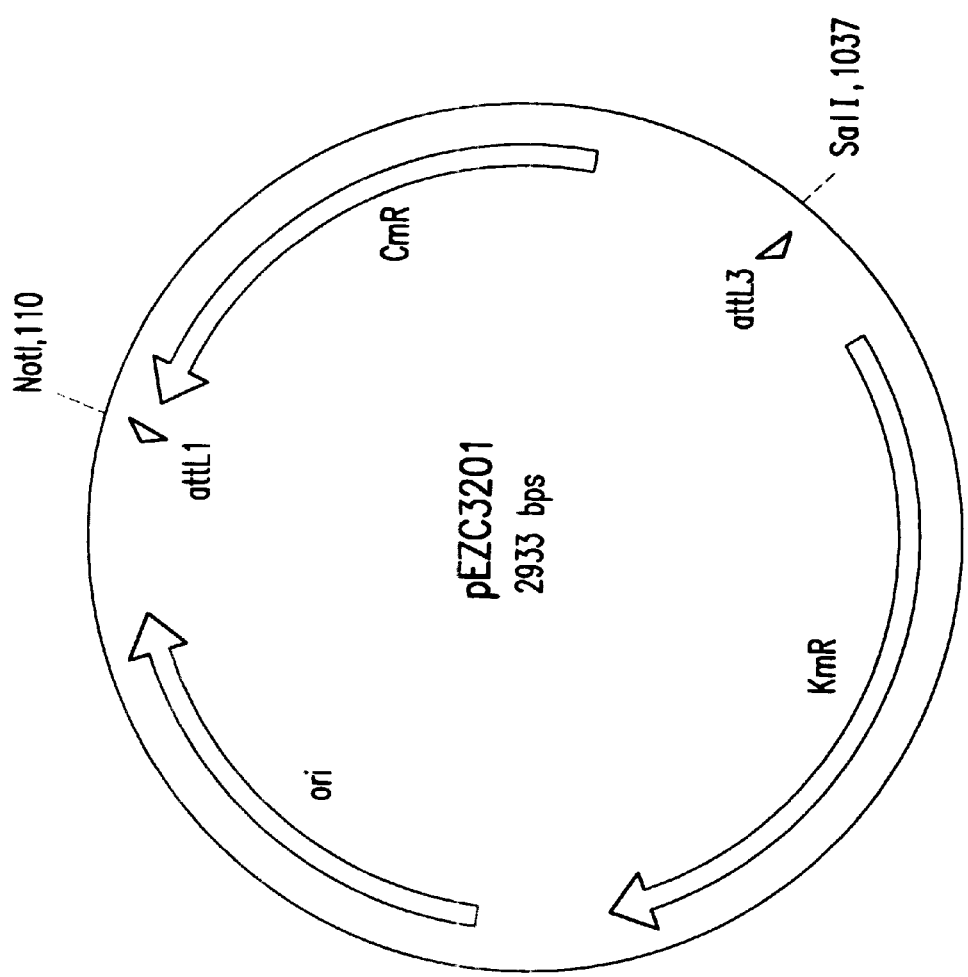
FIG. 8K depicts a vector diagram of pEZC3201.

Unpurified PCR products (about 30 ng) were mixed with the gel purified, linear rf1, rf2, or rf3 cloning vectors (about 50 ng) in a 10 µl reaction containing 1X REact 4 buffer (LTI) and 1 unit UDG (LTI). After 30 minutes at 37° C., 1 µl aliquots of each reaction were transformed into competent *E. coli* DH5α cells (LTI) and plated on agar containing 50 µg/ml kanamycin. Colonies were picked and analysis of miniprep DNA showed that the CAT gene had been cloned in reading frame 1 (pEZC3601)(FIG. 8C), reading frame 2 (pEZC3609)(FIG. 8D) and reading frame 3 (pEZC3617) (FIG. 8E), and that the phoA gene had been cloned in reading frame 1 (pEZC3606)(FIG. 8F), reading frame 2 (pEZC3613)(FIG. 8G) and reading frame 3 (pEZC3621) (FIG. 8H).

Part IV: Subcloning of CAT or phoA from UDG Cloning Vectors into a GST Fusion Vector Plasmids encoding fusions between GST and either CAT or phoA in all three reading frames were constructed by recombinational cloning as follows. Miniprep DNA of GST vector donor pEZC3501(FIG. 8B) (derived from Pharmacia plasmid pGEX-2TK as described above) was linearized with Cla I. About 5 ng of vector donor were mixed with about 10 ng each of the appropriate circular gene donor vectors containing CAT or phoA in 8 µl reactions containing buffer and recombination proteins Int, Xis, and IHF (above). After incubation, 1 µl of each reaction was transformed into *E. coli* strain DH5α and plated on ampicillin, as presented in Table 7.

TABLE 7

| DNA | Colonies (10% of each transformation) |
| --- | --- |
| Linear vector donor (pEZC3501/Cla) | 0 |
| Vector donor + CAT rf1 | 110 |
| Vector donor + CAT rf2 | 71 |
| Vector donor + CAT rf3 | 148 |
| Vector donor + phoA rf1 | 121 |
| Vector donor + phoA rf2 | 128 |
| Vector donor + phoA rf3 | 31 |

Part V: Expression of Fusion Proteins

Two colonies from each transformation were picked into 2 ml of rich medium (CIRCLEGROW® brand culture medium Bio101 Inc.) in 17×100 mm plastic tubes FALCON® brand plasticware, Cat. No. 2059, Becton Dickinson) containing 100 µg/ml ampicillin and shaken vigorously for about 4 hours at 37° C., at which time the cultures were visibly turbid. One ml of each culture was transferred to a new tube containing 10 µl of 10% (w/v) IPTG to induce expression of GST. After 2 hours additional incubation, all cultures had about the same turbidity; the A600 of one culture was 1.5. Cells from 0.35 ml each culture were harvested and treated with sample buffer (containing SDS and β-mercaptoethanol) and aliquots equivalent to about 0.15 A600 units of cells were applied to a Novex 4–20% gradient polyacrylamide gel. Following electrophoresis the gel was stained with Coomassie blue.

Results: Enhanced expression of single protein bands was seen for all 12 cultures. The observed sizes of these proteins correlated well with the sizes predicted for GST being fused (through attB recombination sites without stop codons) to CAT or phoA in three reading frames: CAT rf1=269 amino acids; CAT rf2=303 amino acids; CAT rf3=478 amino acids; phoA rf1=282 amino acids; phoA rf2=280 amino acids; and phoA rf3=705 amino acids.

Analysis: Both CAT and phoA genes were subcloned into a GST fusion vector in all three reading frames, and expression of the six fusion proteins was demonstrated.

While the foregoing invention has been described in some detail for purposes of clarity and understanding, it will be appreciated by one skilled in the art from a reading of this disclosure that various changes in form and detail can be made without departing from the true scope of the invention and appended claims. All patents and publications cited herein are entirely incorporated herein by reference.

What is claimed is:

1. An in vitro method for apposing an expression signal and a gene or partial gene comprising:
   (a) mixing in vitro a first nucleic acid molecule comprising said expression signal and at least a first recombination site, and a second nucleic acid molecule comprising said gene or partial gene and at least a second recombination site; and
   (b) incubating said mixture in vitro in the presence of at least one recombination protein under conditions sufficient to cause recombination of at least said first and second recombination sites thereby apposing said expression signal and said gene or partial gene such that expression of said gene or partial gene can be controlled by said expression signal.

2. The method of claim 1, wherein said at least one recombination protein is encoded by a bacteriophage selected from the group consisting of bacteriophage lambda, phi80, P22, P2, 186, P4 and P1.

3. The method of claim 1 wherein said at least one recombination protein is encoded by bacteriophage lambda.

4. The method of claim 1, wherein said at least one recombination protein is selected from the group consisting of Int, IHF, Xis, and Cre.

5. The method of claim 1, wherein said at least one recombination protein is selected from the group consisting of Int, IHF, and Xis.

6. The method of claim 1, wherein said at least one recombination protein is selected from the group consisting of αγ, Tn3 resolvase, Hin, Gin, Cin, and Flp.

7. The method of claim 1, wherein said at least one recombination protein is Cre.

8. The method of claim 1, wherein said first or second recombination sites are selected from the group consisting of att sites and lox sites.

9. The method of claim 1, wherein said first or second recombination site is an att site.

10. The method of claim 1, wherein said first or second recombination site is a lox site.

11. The method of claim 1, wherein said first nucleic acid molecule is a vector.

12. The method of claim 1, wherein said second nucleic acid molecule is a vector.

13. The method of claim 1, wherein said first and second nucleic acid molecules are vectors.

14. The method of claim 1, wherein at least one of said recombination sites comprises at least one nucleic acid sequence selected from the group consisting of SEQ ID NOs: 1–16, or a nucleic acid sequence complementary thereto.

15. The method of claim 1, wherein at least one of said recombination sites comprises a mutation which enhances recombination specificity.

16. The method of claim 1, wherein at least one of said recombination sites comprises a mutation which removes one or more stop codons from said recombination site.

17. The method of claim 1, wherein at least one of said recombination sites comprises a mutation which avoids hairpin formation.

18. The method of claim 1, wherein said expression signal is a promoter.

19. The method of claim 18, wherein said promoter is selected from the group consisting of a repressible promoter, an inducible promoter and a constitutive promoter.

20. The method of claim 18, wherein said promoter is selected from the group consisting of a CMV promoter and a tac promoter.

21. The method of claim 1, wherein said gene or partial gene comprises a nucleic acid sequence encoding a tag sequence.

22. The method of claim 21, wherein said tag sequence is selected from the group consisting of a GST tag and a His tag.

23. The method of claim 1 wherein said first nucleic acid molecule further comprises at least one additional nucleic acid sequence selected from the group consisting of a Selectable marker, a cloning site, a restriction site, an operon, and an origin of replication.

24. The method of claim 23, wherein said Selectable marker is selected from the group consisting of an antibiotic resistance gene and a toxic gene.

25. The method of claim 1, wherein said second nucleic acid molecule further comprises at least one additional nucleic acid sequence selected from the group consisting of a Selectable marker, a cloning site, a restriction site, an operon, and an origin of replication.

26. The method of claim 25, wherein said Selectable marker is selected from the group consisting of an antibiotic resistance gene and a toxic gene.

27. The method of claim 1, further comprising expressing said gene or partial gene to produce a protein.

28. The method of claim 27, wherein said protein is a fusion protein.

29. The method of claim 28, wherein said fusion protein comprises a tag sequence.

30. The method of claim 29, wherein said tag sequence is selected from the group consisting of a GST tag and a His tag.

31. The method of claim 28, wherein said fusion protein comprises an amino terminal tag sequence.

32. The method of claim 31, wherein said tag sequence is selected from the group consisting of a GST tag and a His tag.

33. The method of claim 28, wherein said fusion protein comprises a carboxy terminal tag sequence.

34. The method of claim 33, wherein said tag sequence is selected from the group consisting of a GST tag and a His tag.

35. The method of claim 1, wherein said recombination produces a third nucleic acid molecule in which said expression signal and said gene or partial gene are apposed, and further comprising introducing said third nucleic acid molecule into a cell.

36. The method of claim 35, wherein said first nucleic acid molecule is a vector.

37. The method of claim 35, wherein said second nucleic acid molecule is a vector.

38. The method of claim 35, wherein said first and second nucleic acid molecules are vectors.

39. The method of claim 35, wherein at least one of said recombination sites comprises at least one nucleic acid sequence selected from the group consisting of SEQ ID NOs: 1–16, or a complementary DNA sequence.

40. The method of claim 35, wherein at least one of said recombination sites comprises a mutation which enhances recombination specificity.

41. The method of claim 35, wherein at least one of said recombination sites comprises a mutation which removes one or more stop codons from said recombination site.

42. The method of claim 35, wherein at least one of said recombination sites comprises a mutation which avoids hairpin formation.

43. The method of claim 35, wherein said expression signal is a promoter.

44. The method of claim 43, wherein said promoter is selected from the group consisting of a repressible promoter, an inducible promoter and a constitutive promoter.

45. The method of claim 43, wherein said promoter is selected from the group consisting of a CMV promoter and a tac promoter.

46. The method of claim 35, wherein said gene or partial gene comprises a nucleic acid sequence encoding a tag sequence.

47. The method of claim 46, wherein said tag sequence is selected from the group consisting of a GST tag and a His tag.

48. The method of claim 35, wherein said first nucleic acid molecule further comprises at least one additional nucleic acid sequence selected from the group consisting of a Selectable maker, a cloning site, a restriction site, an operon, and an origin of replication.

49. The method of claim 48, wherein said Selectable marker is selected from the group consisting of an antibiotic resistance gene and a toxic gene.

50. The method of claim 35, wherein said second nucleic acid molecule further comprises at least one additional nucleic acid sequence selected from the group consisting of a Selectable maker, a cloning site, a restriction site, an operon, and an origin of replication.

51. The method of claim 50, wherein said Selectable marker is selected from the group consisting of an antibiotic resistance gene and a toxic gene.

52. The method of claim 35, further comprising expressing said gene or partial gene to produce a protein.

53. The method of claim 52, wherein said protein is a fusion protein.

54. The method of claim 53, wherein said fusion protein comprises a tag sequence.

55. The method of claim 54, wherein said tag sequence is selected from the group consisting of a GST tag and a His tag.

56. The method of claim 53, wherein said fusion protein comprises an amino terminal tag sequence.

57. The method of claim 56, wherein said tag sequence is selected from the group consisting of a GST tag and a His tag.

58. The method of claim 53, wherein said fusion protein comprises a carboxy terminal tag sequence.

59. The method of claim 58, wherein said tag sequence is selected from the group consisting of a GST tag and a His tag.

60. A method for apposing an expression signal and a gene or partial gene comprising:
(a) mixing a first nucleic acid molecule comprising said expression signal and at least a first recombination site, and a second nucleic acid molecule comprising said gene or partial gene and at least a second recombination site; and
(b) contacting said mixture with at least one recombination protein under conditions sufficient to cause recombination of at least said first and second recombination sites thereby apposing said expression signal and said gene or partial gene,
wherein at least one of said recombination sites comprises at least one nucleic acid sequence selected from the group consisting of SEQ ID NOs: 1–16, or a nucleic acid sequence complementary thereto.

61. A method for apposing an expression signal and a gene or partial gene comprising:
(a) mixing a first nucleic acid molecule comprising said expression signal and at least a first recombination site, and a second nucleic acid molecule comprising said gene or partial gene and at least a second recombination site; and
(b) contacting said mixture with at least one recombination protein under conditions sufficient to cause recombination of at least said first and second recombination sites thereby apposing said expression signal and said gene or partial gene,
wherein at least one of said recombination sites comprises a mutation which removes one or more stop codons from said recombination site.

62. A method for apposing an expression signal and a gene or partial gene comprising:
(a) mixing a first nucleic acid molecule comprising said expression signal and at least a first recombination site, and a second nucleic acid molecule comprising said gene or partial gene and at least a second recombination site; and
(b) contacting said mixture with at least one recombination protein under conditions sufficient to cause recombination of at least said first and second recombination sites thereby apposing said expression signal and said gene or partial gene,
wherein at least one of said recombination sites comprises a mutation which avoids hairpin formation.

63. An in vitro method for apposing an expression signal and a gene or partial gene comprising:
(a) mixing in vitro
(i) a first nucleic acid molecule comprising said expression signal, and a first recombination site and a second recombination site, wherein said first and second recombination sites do not recombine with each other; and
(ii) a second nucleic acid molecule comprising said gene or partial gene, and a third recombination site and a fourth recombination site, wherein said third and fourth recombination sites do not recombine with each other; and
(b) contacting said mixture in vitro with at least one recombination protein under conditions sufficient to cause recombination of said first and third recombination sites and/or said second and fourth recombination sites, thereby apposing said expression signal and said gene or partial gene such that expression of said gene or partial gene can be controlled by said expression signal and such that a single protein is expressed upon expression of said gene or partial gene.

64. An in vitro method for apposing an expression signal and a gene or partial gene comprising:
(a) mixing in vitro
(i) a first nucleic acid molecule comprising said expression signal, and a first recombination site and a second recombination site, wherein said first and second recombination sites do not recombine with each other; and
(ii) a second nucleic acid molecule comprising said gene or partial gene, and a third recombination site and a fourth recombination site, wherein said third and fourth recombination sites do not recombine with each other; and
(b) contacting said mixture in vitro with at least one recombination protein under conditions sufficient to cause recombination of said first and third recombination sites and/or said second and fourth recombination sites, thereby apposing said expression signal and said gene or partial gene.

65. The method of any one of claims 60–62, wherein said recombination occurs in vivo.

66. The method of any one of claims 60–62, wherein said recombination occurs in vitro.

67. The method of any one of claims 60–63 and 64, wherein said recombination produces a third nucleic acid molecule in which said expression signal and said gene or partial gene are apposed, and further comprising introducing said third nucleic acid molecule into a cell.

68. The method of any one of claims 1, 60–63 and 64, wherein said first nucleic acid molecule and/or said second nucleic acid molecule further comprises at least one Selectable marker.

69. The method of claim 68, wherein said at least one Selectable marker is a toxic gene.

70. The method of any one of claims 60–63 and 64, wherein said expression signal is a promoter.

71. The method of claim 70, wherein said promoter is selected from the group consisting of a repressible promoter, an inducible promoter and a constitutive promoter.

72. The method of claim 70, wherein said promoter is selected from the group consisting of a CMV promoter and a tac promoter.

73. The method of any one of claims 60–63 and 64, wherein said gene or partial gene comprises a nucleic acid sequence encoding a tag sequence.

74. The method of claim 73, wherein said tag sequence is selected from the group consisting of a GST tag and a His tag.

75. The method of any one of claims 60–63 and 64, wherein said first nucleic acid molecule and/or said second nucleic acid molecule further comprises at least one additional nucleic acid sequence selected from the group consisting of a cloning site, a restriction site, an operon, and an origin of replication.

76. The method of any one of claims 60–63 and 64, further comprising expressing said gene or partial gene to produce a protein.

77. The method of claim 76, wherein said protein is a fusion protein.

78. The method of claim 77, wherein said fusion protein comprises a tag sequence.

79. The method of claim 78, wherein said tag sequence is selected from the group consisting of a GST tag and a His tag.

80. The method of claim 77, wherein said fusion protein comprises an amino terminal tag sequence.

81. The method of claim 77, wherein said fusion protein comprises a carboxy terminal tag sequence.

82. The method of any one of claims 61–63 and 64, wherein said at least one recombination protein is encoded by a bacteriophage selected from the group consisting of bacteriophage lambda, phi80, P22, P2, 186, P4 and P1.

83. The method of any one of claims 61–63 and 64, wherein said at least one recombination protein is encoded by bacteriophage lambda.

84. The method of any one of claims 61–63 and 64, wherein said at least one recombination protein is selected from the group consisting of Int, IHF, Xis, and Cre.

85. The method of any one of claims 60–63 and 64, wherein said at least one recombination protein is selected from the group consisting of Int, IHF, and Xis.

86. The method of any one of claims 61–63 and 64, wherein said at least one recombination protein is selected from the group consisting of αγ, Tn3 resolvase, Hin, Gin, Cin, and Flp.

87. The method of any one of claims 61–63 and 64, wherein said at least one recombination protein is Cre.

88. The method of any one of claims 61–63 and 64, wherein at least one of said recombination sites is selected from the group consisting of att sites and lox sites.

89. The method of any one of claims 60–63 and 64, wherein at least one of said recombination sites is an att site.

90. The method of any one of claims 61–63 and 64, wherein at least one of said recombination sites is a lox site.

91. The method of any one of claims 60–63 and 64, wherein said first nucleic acid molecule is a vector.

92. The method of any one of claims 60–63 and 64, wherein said second nucleic acid molecule is a vector.

93. The method of any one of claims 60–63 and 64, wherein said first and second nucleic acid molecules are vectors.

94. The method of claim 64, further comprising:
(c) contacting one or more hosts with said mixture; and
(d) selecting for a host comprising a nucleic acid molecule in which said expression signal and said gene or partial gene have been apposed, and selecting against a host comprising said first nucleic acid molecule and against a host comprising said second nucleic acid molecule.

95. The method of claim 94, wherein said host is *E. coli*.

96. The method of claim 94, further comprising expressing said gene or partial gene to produce a protein.

97. The method of claim 94, wherein said selection is accomplished using at least one Selectable marker.

98. The method of claim 94, wherein said Selectable marker is selected from the group consisting of an antibiotic resistance gene and a toxic gene.

99. The method of claim 1, further comprising:
(c) contacting one or more hosts with said mixture; and
(d) selecting for a host comprising a nucleic acid molecule in which said expression signal and said gene or partial gene have been apposed, and selecting against a host comprising said first nucleic acid molecule and against a host comprising said second nucleic acid molecule.

100. The method of claim 99, wherein said host is *E. coli*.

101. The method of claim 99, further comprising expressing said gene or partial gene to produce a protein.

102. The method of claim 99, wherein said selection is accomplished using at least one Selectable marker.

103. The method of claim 99, wherein said Selectable marker is selected from the group consisting of an antibiotic resistance gene and a toxic gene.

104. An in vitro method for apposing an expression signal and a gene or partial gene, comprising:
(a) inserting, by direct ligation cloning, a DNA segment comprising said gene or partial gene into a first nucleic acid molecule comprising at least a first recombination site, thereby producing a second nucleic acid molecule comprising said gene or partial gene and at least said first recombination site;
(b) mixing in vitro said second nucleic acid molecule with a third nucleic acid molecule comprising said expression signal and at least a second recombination site; and
(c) incubating said mixture in vitro in the presence of at least one recombination protein under conditions sufficient to cause recombination of at least said first and said second recombination sites, thereby producing a fourth nucleic acid molecule wherein said expression signal and said gene or partial gene have been apposed such that expression of said gene or partial gene can be controlled by said expression signal.

105. The method of claim 104, wherein said at least one recombination protein is selected from the group consisting of Int, IHF, Xis, and Cre.

106. The method of claim 104, wherein said at least one recombination protein is Cre.

107. The method of claim 104, wherein said first or second recombination sites are selected from the group consisting of att sites and lox sites.

108. The method of claim 104, wherein said first or second recombination site is a lox site.

109. The method of claim 104, wherein said second nucleic acid molecule is a vector.

110. The method of claim 104, wherein said third nucleic acid molecule is a vector.

111. The method of claim 104, wherein said second and third nucleic acid molecules are vectors.

112. The method of claim 104, wherein said expression signal is a promoter.

113. The method of claim 104, wherein said second nucleic acid molecule further comprises at least one additional nucleic acid sequence selected from the group consisting of a Selectable marker, a cloning site, a restriction site, an operon, and an origin of replication.

114. The method of claim 104, wherein said third nucleic acid molecule further comprises at least one additional nucleic acid sequence selected from the group consisting of a Selectable marker, a cloning site, a restriction site, an operon, and an origin of replication.

115. The method of claim 104, wherein at least one of said recombination sites comprises a mutation which removes one or more stop codons from said recombination site.

116. The method of claim 104, wherein at least one of said recombination sites comprises a mutation which avoids hairpin formation.

117. The method of claim 104, further comprising introducing said fourth nucleic acid molecule into a cell.

118. The method of claim 117, wherein at least one of said recombination sites comprises a mutation which removes one or more stop codons from said recombination site.

119. The method of claim 117, wherein at least one of said recombination sites comprises a mutation which avoids hairpin formation.

120. The method of claim 104, further comprising expressing said gene or partial gene to produce a protein.

121. The method of claim 120, wherein said protein is a fusion protein.

122. The method of claim 121, wherein said fusion protein comprises a tag sequence.

123. The method of claim 122, wherein said tag sequence is selected from the group consisting of a GST tag and a His tag.

124. The method of claim 117, further comprising expressing said gene or partial gene to produce a protein.

125. The method of claim 124, wherein said protein is a fusion protein.

126. The method of claim 125, wherein said fusion protein comprises a tag sequence.

127. The method of claim 126, wherein said tag sequence is selected from the group consisting of a GST tag and a His tag.

128. The method of claim 104, further comprising:
(c) contacting one or more hosts with said mixture; and
(d) selecting for a host comprising a nucleic acid molecule in which said expression signal and said gene or partial gene have been apposed, and selecting against a host comprising said first nucleic acid molecule and against a host comprising said second nucleic acid molecule.

129. The method of claim 128, wherein said selection is accomplished using at least one Selectable marker.

130. The method of claim 129, wherein said Selectable marker is selected from the group consisting of an antibiotic resistance gene and a toxic gene.

* * * * *